United States Patent [19]

Pasteris et al.

[11] Patent Number: 4,746,355

[45] Date of Patent: May 24, 1988

[54] BENZYLSULFONYLUREAS AND ARYLSULFAMOYLUREAS

[75] Inventors: Robert J. Pasteris; Mark E. Thompson, both of Wilmington, Del.

[73] Assignee: E. I. Du Pont De Nemours and Company, Wilmington, Del.

[21] Appl. No.: 886,151

[22] Filed: Jul. 16, 1986

Related U.S. Application Data

[60] Division of Ser. No. 686,796, Dec. 26, 1984, Pat. No. 4,609,395, which is a continuation-in-part of Ser. No. 585,170, Mar. 1, 1984, abandoned.

[51] Int. Cl.$^4$ ............... C07D 251/16; C07D 401/12; C07D 417/12; A01N 43/66
[52] U.S. Cl. ........................................ 71/93; 71/90; 71/91; 71/92; 544/49; 544/209; 544/207; 544/212; 544/211; 544/206; 544/208
[58] Field of Search ............. 71/93, 90, 91; 544/212, 544/207, 209, 49, 211, 206, 208

[56] References Cited

U.S. PATENT DOCUMENTS

| | | | |
|---|---|---|---|
| 4,169,719 | 10/1979 | Levitt | 544/320 |
| 4,221,585 | 9/1980 | Levitt | 71/92 |
| 4,302,241 | 11/1981 | Levitt | 71/92 |
| 4,348,220 | 9/1982 | Schwing | 71/92 |
| 4,420,325 | 12/1983 | Sauers | 71/92 |
| 4,634,465 | 1/1987 | Ehrenfreund et al. | 71/93 |

FOREIGN PATENT DOCUMENTS

| | | |
|---|---|---|
| 71441 | 2/1983 | European Pat. Off. |
| 79683 | 5/1983 | European Pat. Off. |

Primary Examiner—John M. Ford
Attorney, Agent, or Firm—James A. Costello

[57] ABSTRACT

Benzylsulfonylureas and arylsulfamoylureas are useful as pre-emergent and post-emergent herbicides and as plant growth regulants.

22 Claims, No Drawings

BENZYLSULFONYLUREAS AND ARYLSULFAMOYLUREAS

CROSS-REFERENCE TO RELATED APPLICATIONS

This application is a division of application Ser. No. 686,796, filed on Dec. 26, 1984, now U.S. Pat. No. 4,609,395, which is a continuation-in-part of application Ser. No. 585,170 filed on Mar. 1, 1984, and now abandoned.

BACKGROUND OF THE INVENTION

European patent application No. 51,466, published May 12, 1982, discloses compounds of the formula

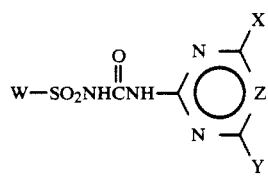

where W is a substituted benzyl; Z is CH or N; X is $CH_3$, $OCH_3$, or Cl; and Y is $CH_3$, $C_2H_5$, $OCH_3$, $OC_2H_5$, $CH_2OCH_3$, $NH_2$, $NHCH_3$, or $N(CH_3)_2$. The compounds are disclosed to have pre- and post-emergent herbicidal activity and to be useful as plant growth regulators.

European patent application No. 71,441, published Feb. 9, 1983, discloses compounds of the formula

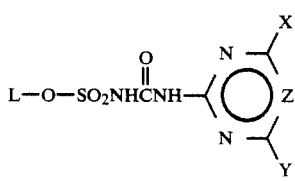

where
Z is CH or N; X is $CH_3$ or $OCH_3$; Y is Cl, $CH_3$, $OCH_3$, $OC_2H_5$, $CH_2OCH_3$, $NH_2$, $NHCH_3$, $N(CH_3)_2$, $CH(OCH_3)_2$, or

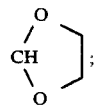

and
L is

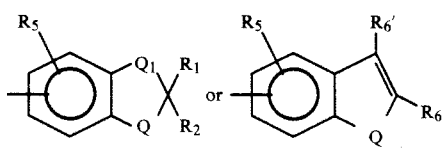

where
$R_1$ is H or $C_1$-$C_3$ alkyl; $R_2$ is H or $CH_3$, $R_5$ is H, $CH_3$, $OCH_3$, Cl, Br, $NO_2$, $CO_2R_7$, $SO_2R_8$, $OSO_2R_9$, $SO_2NR_{10}R_{11}$; $R_6$ is H or $C_1$-$C_3$ alkyl; $R_6'$ is H or $CH_3$; Q is O, S, or $SO_2$; and $Q_1$ is $CR_3R_4$ or O.

Utility as a pre- or post-emergent herbicide and as a plant growth regulant is disclosed.

European patent application No. 79,683, published May 25, 1983, discloses compounds, useful as herbicides or plant growth regulants, of the formula

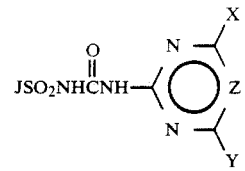

where
Z is CH or N; X and Y are as in European application No. 51,466 (described above) and J is

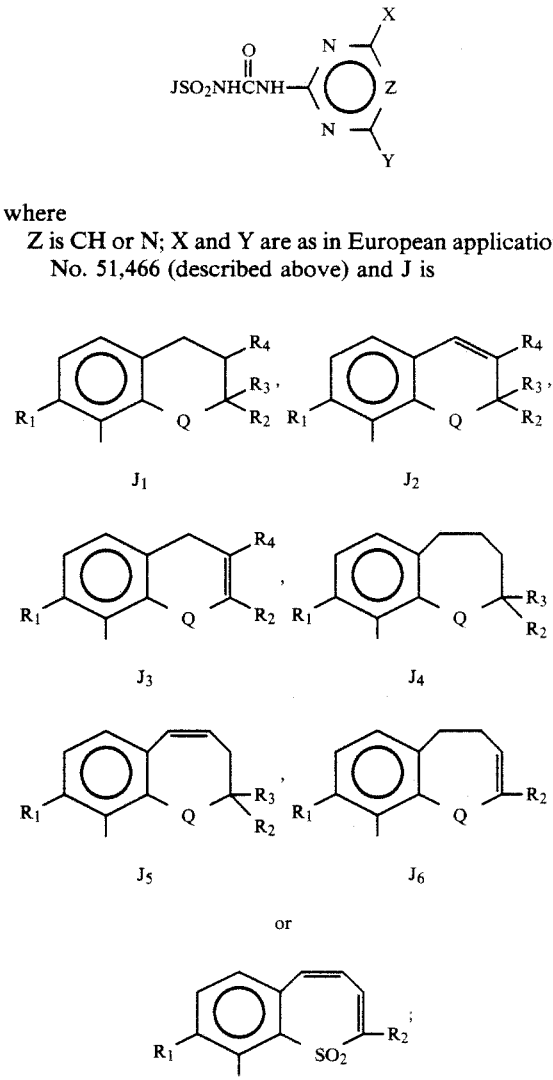

Q is O, S or $SO_2$;
R is H or $CH_3$;
$R_1$ is H, $CH_3$, $OCH_3$, Cl, Br, $CO_2R_5$, $SO_2R_6$, $OSO_2R_7$ or $SO_2NR_8R_9$;
$R_2$ and $R_3$ are independently H or $C_1$-$C_3$ alkyl;
$R_4$ is H or $CH_3$;
$R_5$ $C_1$-$C_3$ alkyl, $CH_2CH=CH_2$, $CH_2CH_2OCH_3$ or $CH_2CH_2Cl$;
$R_6$ is $C_1$-$C_3$ alkyl;
$R_7$ is $C_1$-$C_3$ alkyl or $CF_3$; and
$R_8$ and $R_9$ are independently $C_1$-$C_2$ alkyl.

SUMMARY OF THE INVENTION

The present invention relates to novel compounds of Formula I, agriculturally suitable compositions containing them, and their method-of-use as pre-emergent or post-emergent herbicides or plant growth regulants.

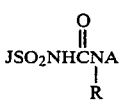

wherein J is

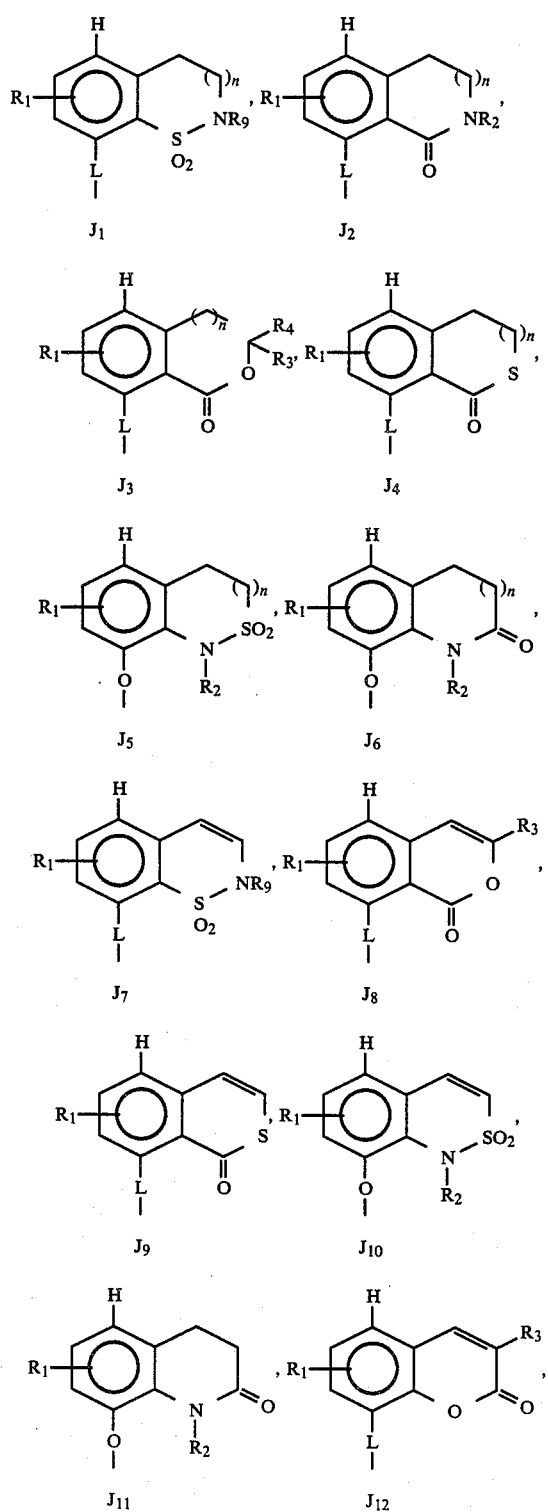

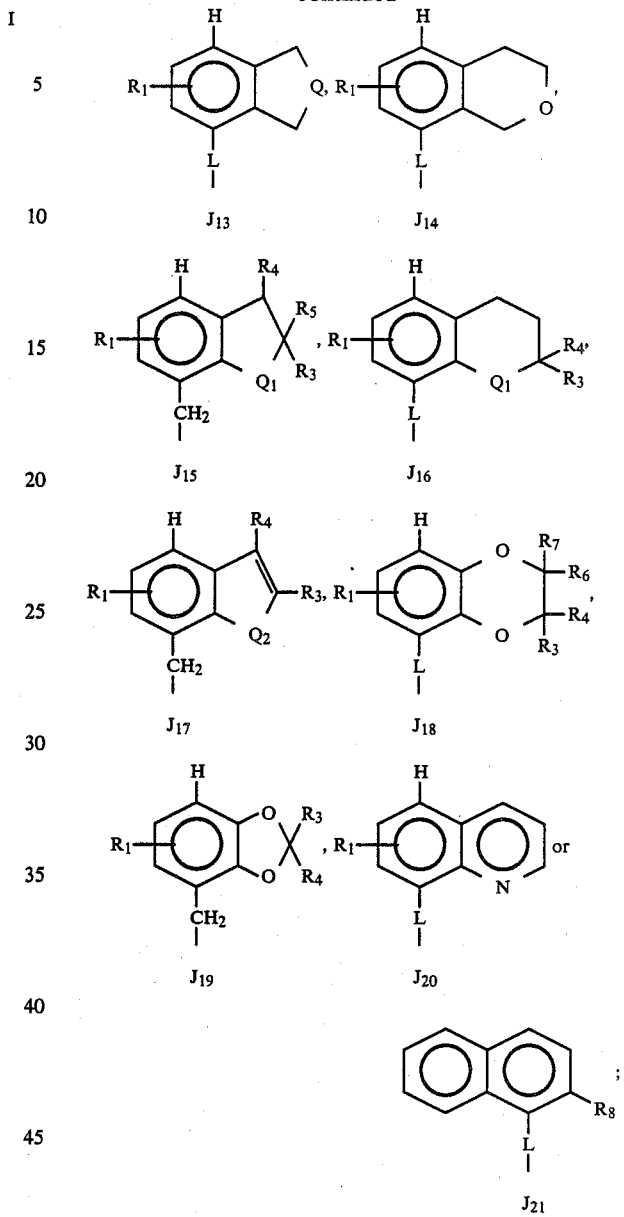

n is 0 or 1;
L is $CH_2$ or O;
Q is $CH_2$ or O;
$Q_1$ is O, S or $SO_2$;
$Q_2$ is O or S;
R is H or $CH_3$;
$R_1$ is H, F, Cl, Br, $CH_3$ or $OCH_3$;
$R_2$ is H or $C_1$-$C_3$ alkyl;
$R_3$ is H or $CH_3$;
$R_4$ is H or $CH_3$;
$R_5$ is H, $CH_3$ or $C_2H_5$;
$R_6$ is H or $CH_3$;
$R_7$ is H or $CH_3$;
$R_8$ is F, Cl, Br, $OCH_3$, $SCH_3$, $SO_2CH_3$, $CO_2CH_3$, $SO_2N(CH_3)_2$ or $OSO_2CH_3$;
$R_9$ is H, OH, $C_1$-$C_6$ alkyl, $C_1$-$C_6$ haloalkyl, $C_1$-$C_6$ alkoxyalkyl, $C_3$-$C_6$ alkenyl, $C_3$-$C_6$ alkynyl, $C_1$-$C_6$ alkoxy, phenyl, $C_3$-$C_6$ cycloalkyl, $C_4$-$C_7$ cycloalkylalkyl, $C_1$-$C_6$ alkylcarbonyl, $C_1$-$C_6$ alkoxycarbonyl, benzyl, $C_3$–$C_4$ haloalkenyl, $C_3$–$C_6$ haloalkynyl, $C_3$–$C_6$ alkylcarbonylalkyl, $C_3$–$C_6$ alkoxycarbonylalkyl or $C_1$–$C_4$ cyanoalkyl;

A is

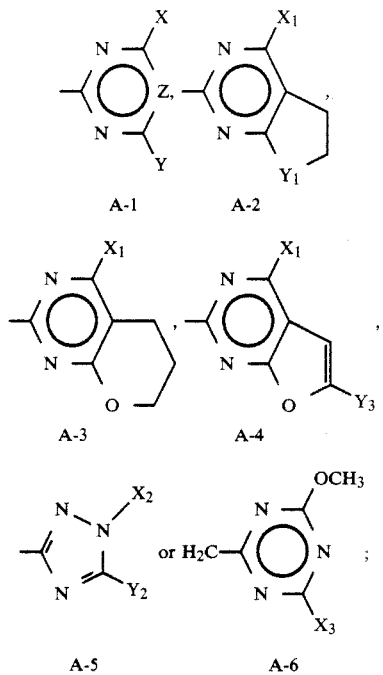

X is $CH_3$, $OCH_3$, Cl, Br, $OCH_2CF_3$ or $OCF_2H$;
Y is $C_1$–$C_3$ alkyl, $CH_2F$, cyclopropyl, $C\equiv CH$, $OCH_3$, $OC_2H_5$, $CH_2OCH_3$, $NH_2$, $NHCH_3$, $N(CH_3)_2$, $OCH_2CH_2F$, $CF_3$, $SCH_3$, $OCH_2CH=CH_2$, $OCH_2C\equiv CH$, $OCH_2CH_2OCH_3$, $CR(OCH_3)_2$,

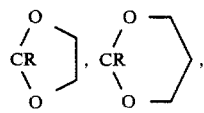

$CR(OCH_2CH_3)_2$ or $OCF_2H$;
Z is CH or N;
$X_1$ is $CH_3$, $OCH_3$, $OC_2H_5$ or $OCF_2H$;
$Y_1$ is O or $CH_2$;
$X_2$ is $CH_3$, $C_2H_5$ or $CH_2CF_3$;
$Y_2$ is $OCH_3$, $OC_2H_5$, $SCH_3$, $SC_2H_5$, $OCF_2H$, $SCF_2H$, $CH_3$ or $CH_2CH_3$;
$X_3$ is $CH_3$ or $OCH_3$; and
$Y_3$ is H or $CH_3$;
provided that
(1) when X is Cl or Br, then Z is CH and Y is $OCH_3$, $OC_2H_5$, $NHCH_3$, $N(CH_3)_2$ or $OCF_2H$; and
(2) when X or Y is $OCF_2H$, then Z is CH.

Compounds of formula I that are preferred for reasons of their higher herbicidal activity, greater plant growth regulant activity or more favorable ease of synthesis are:

(1) Compounds in which A is A-1.
(2) Compounds of the scope of (1) where Y is $CH_3$, $C_2H_5$, $OCH_3$, $OC_2H_5$, $CH_2OCH_3$, $CH_2F$ or $CF_3$; and L is $CH_2$.
(3) Compounds of the scope of (2) where J is $J_1$, $J_3$, $J_7$, $J_8$, $J_{15}$ or $J_{16}$.

(4) Compounds of the scope of (3) where R is H; $R_1$ is H; and X is $CH_3$ or $OCH_3$.

Compounds that are specifically preferred are
1,3-dihydro-N-[(4,6-dimethoxypyrimidin-2-yl)aminocarbonyl]-1-oxo-benzo[c]furan-7-methanesulfonamide;
1,3-dihydro-N-[(4-methoxy-6-methyl-1,3,5-triazin-2-yl)aminocarbonyl]-1-oxo-benzo[c]furan-7-methanesulfonamide;
N-[(4,6-dimethoxypyrimidin-2-yl)aminocarbonyl]-2,3-dihydro-2-methyl-benzo[B]thiophene-7-methanesulfonamide-1,1-dioxide; and
N-[(4-methoxy-6-methyl-1,3,5-triazin-2-yl)aminocarbonyl]-2-methyl-benzo[B]thiophene-7-methanesulfonamide-1,1-dioxide.

DETAILED DESCRIPTION OF THE INVENTION

Synthesis

The compounds of Formula I can be prepared as indicated by one or more of the methods shown below in Equations 1, 2, 3, and 4.

Equation 1 depicts the reaction of sulfonyl isocyanates of Formula II, where J is other than $J_{19}$, with the appropriate heterocyclic amines, III, to give the desired products of Formula Ia.

Equation 1

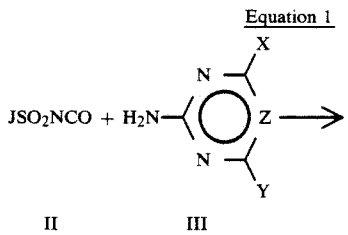

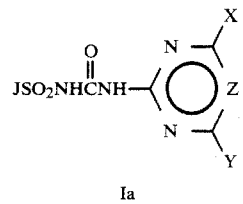

wherein
J, X, Y and Z are as previously defined, $R_2$ is $C_1$–$C_3$ alkyl and $R_9$ is other than H or OH.

The reaction of Equation 1 is best carried out in an inert aprotic solvent such as methylene chloride, tetrahydrofuran, or acetonitrile at a temperature between 20° and 80° C. A catalytic amount of 1,4-diazabicyclo[2,2,2]octane (DABCO) may be used to accelerate the reaction. In cases in which the products are insoluble in the reaction solvent, they may be isolated by simple filtration. When the products are soluble, they may be isolated by evaporation of the solvent and trituration of the residue with solvents such as 1-chlorobutane, diethyl ether, or methanol, and filtration.

Compounds of Formula Ib, where J is other than $J_3$, $J_4$, $J_5$, $J_6$, $J_8$, $J_9$, and $J_{12}$, and where L is —$CH_2$—, can be prepared as shown in Equation 2 by treating sulfonamides of Formula IV with the methyl ester of a pyrimidine or triazinecarbamic acid of Formula V in the presence of an equimolar quantity of trimethylaluminum.

Equation 2

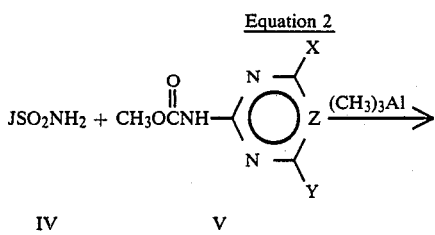

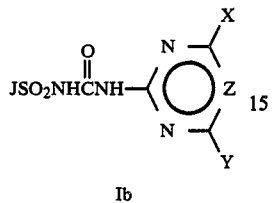

wherein

X, Y and Z are as previously defined and J is as defined above.

The reaction of Equation 2 is best carried out at temperatures between 25° and 83° C. in a solvent such as methylene chloride or 1,2-dichloroethane for 12 to 96 hours under an inert atmosphere, as taught in European Pat. No. 84,244 (issued July 27, 1983). The methyl carbamates, V, can be conveniently synthesized by treatment of the corresponding heterocyclic amines of Formula III with dimethyl carbonate or methyl chloroformate in the presence of a base such as sodium hydride or pyridine.

Alternatively, compounds of Formula Ic, where J is other than $J_5$, $J_6$, $J_{10}$, and $J_{11}$, and where L is —$CH_2$—, can be prepared as shown below in Equation 3 by the reaction of sulfonamides of Formula IV with the phenyl ester of the appropriate carbamic acid, VI, in the presence of an equimolar quantity of a tertiary amine base such as 1,5-diazabicyclo[5.4.0]undec-5-ene (DBU).

Equation 3

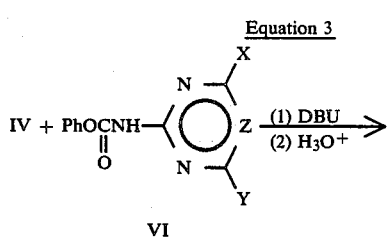

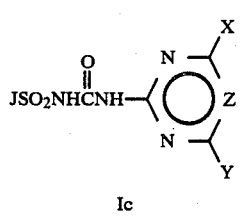

wherein

J, X, Y and Z are as previously defined.

The reaction shown in Equation 3 is carried out at about 23° C. in a suitable solvent such as dioxane or acetonitrile. Aqueous acid work-up affords the desired products as described in European patent application No. 70,804 (published Jan. 26, 1983). The phenyl carbamates, VI, can be synthesized by treating the corresponding heterocyclic amines of Formula III with di- phenyl carbonate or phenyl chloroformate in the presence of a base such as sodium hydride or pyridine.

Compounds of Formula Id, where J is other than $J_{15}$, $J_{17}$, and $J_{19}$, and where L is O, can be prepared as shown below in Equation 4. The intermediate chlorosulfonylurea of Formula VII is formed by treatment of the corresponding heterocyclic amine, III, with commercially available chlorosulfonyl isocyanate and is then allowed to react with an appropriate phenol of Formula VIII.

Equation 4

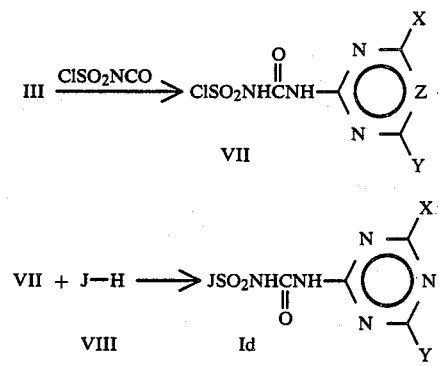

wherein

J, X, Y and Z are as previously defined.

The reaction shown in Equation 4 is best carried out according to the methods taught in U.S. Pat. No. 4,391,976.

Sulfonyl isocyanates of Formula IIa, where J is other than $J_{19}$, and $R_2$ is $C_1$-$C_3$ alkyl, $R_9$ is other than hydrogen and hydroxy, and where L is —$CH_2$—, can be prepared as shown in Equation 5 by the reaction of the corresponding sulfonamides of general structure IV with phosgene in the presence of n-butyl isocyanate and a catalytic amount of 1,4-diazabicyclo[2.2.2]octane (DABCO). Alternatively, the sulfonyl isocyanates, IIa, may be prepared via phosgenation of the appropriate n-butylureas of Formula IX as represented in Equation 6.

Equation 5

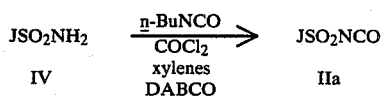

wherein

J is as previously defined.

The reaction shown in Equation 5 is best carried out according to the procedure described in U.S. Pat. No. 4,238,621.

Equation 6

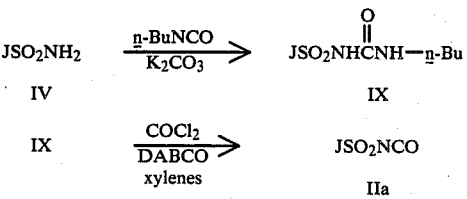

wherein

J is as previously defined.

The compounds of Formula IX are conveniently prepared by stirring a mixture of the appropriate sulfonamides, IV, anhydrous potassium carbonate, and n-butyl isocyanate in acetone or methyl ethyl ketone at 25° to 80° C. until all of the isocyanate has reacted. The products are isolated by quenching in dilute mineral acid and recrystallizing the solid product. The compounds IX are treated with phosgene and a catalytic amount of DABCO in refluxing xylene or chlorobenzene in a manner analogous to that described in Equation 5.

Another method for the preparation of sulfonyl isocyanates IIa is shown in Equation 7. Treatment of sulfonamides of Formula IV with thionyl chloride gives intermediate N-sulfinylsulfonamides, X, which afford sulfonyl isocyanates of Formula IIa upon exposure to phosgene in the presence of a catalytic amount of pyridine.

Equation 7

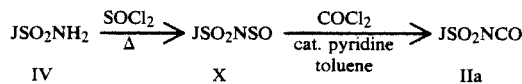

wherein

J is as previously defined.

The reaction of Equation 7 can best be performed according to the procedure of H. Ulrich, B. Tucker, and A. Sayigh, *J. Org. Chem.*, 34, 3200 (1969).

Sulfonyl isocyanates of Formula IIb, where J is other than $J_{15}$, $J_{17}$ or $J_{19}$, $R_2$ is $C_1$–$C_3$ alkyl, $R_9$ is other than hydrogen and hydroxy, and L is O, can be most easily prepared as shown below in Equation 8 by the reaction of appropriately substituted phenols of Formula VIII with chlorosulfonyl isocyanate. This procedure is taught in U.S. Pat. Nos. 4,191,553 and 4,394,153, and by Lohaus in *Chem. Ber.*, 105, 2791 (1972).

Equation 8

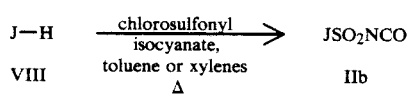

wherein

J is as previously defined.

The requisite sulfonamides of Formula IVa can be synthesized from the appropriately substituted benzyl chlorides or benzyl bromides, XI, by the three-step sequence of reactions outlined below in Equation 9.

Equation 9

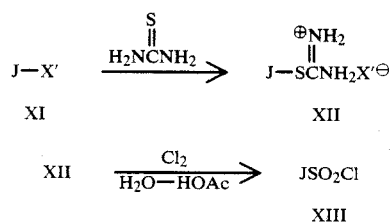

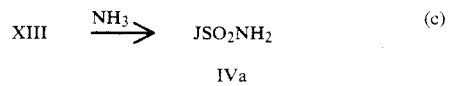

wherein

X' is chlorine or bromine;

J is $J_1$, $J_2$, $J_3$, $J_{13}$, $J_{14}$, $J_{15}$, $J_{16}$, $J_{20}$, or $J_{21}$;

L is —CH$_2$—; and when J is $J_{15}$ or $J_{16}$, $Q_1$ is $SO_2$.

Equation 9(a)

The conversion of alkyl halides to isothiouronium salts is well precedented in the literature. For relevant examples, see T. B. Johnson and J. M. Sprague, *J. Am. Chem. Soc.*, 58, 1348 (1936); 59, 1837 and 2439 (1937); 61, 176 (1939). In a typical procedure, a benzyl halide of Formula XI is treated with thiourea in a suitable solvent such as ethanol or tetrahydrofuran. Temperatures of 40°–80° C. over onehalf to 4 hours are typically required to complete the reaction. The product salts, XII, are isolated by cooling and filtration or by concentration to remove the solvent. The salts, XII, are generally sufficiently pure to be carried on directly to step (9b) without further purification.

Equation 9(b)

The oxidative chlorination of isothiouronium salts to afford sulfonyl chlorides is most conveniently effected according to the procedure of Johnson as described in *J. Am. Chem. Soc.*, 61, 2548 (1939). Thus, the appropriate isothiouronium salts, XII, are suspended in aqueous acetic acid and treated with at least three equivalents of chlorine at temperatures between 0° and 20° C. The product sulfonyl chlorides of Formula XIII are isolated by filtration or extraction into methylene chloride followed by drying and evaporation of the solvent. No further purification of the sulfonyl chlorides is necessary.

Equation 9(c)

In Equation (9c), the sulfonyl chlorides of Formula XIII are suspended in an aprotic solvent such as diethyl ether, 1-chlorobutane, methylene chloride, or tetrahydrofuran and contacted with an excess of anhydrous ammonia at a temperature of 0° to 25° C. The product sulfonamides of Formula IVa are isolated by filtration and washing with water to remove the byproduct ammonium chloride, and concentrating the organic solution. Frequently, the crude sulfonamides may be used directly to prepare the sulfonyl isocyanates of Formula II. However, they may also be purified first by recrystallization from a suitable organic solvent such as ethanol, acetonitrile or chloroform.

Sulfonamides of Formula IVb can be prepared starting from the appropriate benzyl halides of Formula XI by the three-step sequence of reactions shown below in Equation 10.

Equation 10

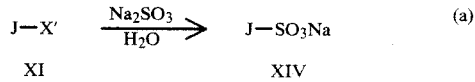

-continued
Equation 10

$$XIV \xrightarrow[\Delta]{PCl_5 \text{ or } POCl_3} JSO_2Cl \quad (b)$$
$$\qquad\qquad\qquad\qquad XIII$$

$$XIII \xrightarrow{NH_3} JSO_2NH_2 \quad (c)$$
$$\qquad\qquad\qquad IVb$$

wherein
  X' is chlorine or bromine;
  J is other than $J_2$, $J_5$, $J_6$, $J_{10}$ or $J_{11}$; and
  L is $-CH_2-$.

Equation 10(a)

The displacement reaction of Equation 10(a) is best carried out by treating the benzyl halides XI with sodium sulfite at reflux temperature for 3 to 12 hours in water or aqueous methanol. The solution is cooled and the solvent removed in vacuo to give a residue which is washed with methanol or ethyl acetate and filtered. Evaporation of the filtrate affords the sodium sulfonate salt which is typically carried directly on to the next step. For examples of this reaction, see Reed and Tarter, *J. Am. Chem. Soc.*, 57, 571 (1935); and Latimer and Bost, *J. Org. Chem.*, 5, 24 (1940).

Equation 10(b)

The reaction shown in Equation 10(b) can be effected by warming a mixture of the dried salts of Formula XIV with phosphorous pentachloride or phosphorous oxychloride according to the procedure of S. Hazlet, *J. Am. Chem. Soc.*, 59, 287 (1937) or O. Billeter, *Ber. Deut. Chem. Ges.*, 38, 2018 (1935). The product sulfonyl chlorides, XIII, are isolated either by distillation from the crude reaction mixture or by extraction into a suitable solvent such as methylene chloride or 1-chlorobutane.

Equation 10(c)

The amination reaction of Equation 10(c) is carried out as described above for Equation 9(c).

Benzyl halides of Formulas XIa and XIb (X'=Br or Cl) may be prepared as shown below in Equation 11 by treatment of the appropriately substituted toluene derivatives, XV, with either N-bromosuccinimide (NBS) or N-chlorosuccinimide (NCS).

Equation 11

$$J-H \xrightarrow[\text{catalyst}]{NBS} J-X' \quad (X' = Br)$$
$$XV \qquad\qquad XIa$$

$$J-H \xrightarrow[\text{catalyst}]{NCS} J-X' \quad (X' = Cl)$$
$$XV \qquad\qquad XIb$$

wherein
  X' is chlorine or bromine;
  J is $J_7$, $J_8$, $J_9$, $J_{12}$, $J_{17}$, $J_{18}$, $J_{19}$, $J_{20}$ and $J_{21}$;
  L is $-CH_2-$;
  $R_1$ is H, F, Cl, Br or $OCH_3$; and
  when J is $J_8$ or $J_{12}$, $R_3$ is H, and
  when J is $J_{17}$, $R_3$ and $R_4$ are H.

The reaction of Equation 11 can be most conveniently carried out by heating a solution of the toluene derivatives, XV, and either N-bromosuccinimide or N-chlorosuccinimide in a suitable solvent such as carbon tetrachloride at reflux temperature. A free radical catalyst such as azoisobutyronitrile or benzoyl peroxide is usually employed to initiate the reaction. When the reaction is complete, the cooled solution is filtered to remove the by-product succinimide and the filtrate concentrated in vacuo. The benzyl halides of Formulas XIa and XIb are often obtained in a sufficiently pure state for further transformation.

An alternate method for the preparation of benzyl chlorides of Formula XIb starting from the appropriate benzyl alcohols of Formula XVI is outlined below in Equation 12.

Equation 12

$$J-OH \xrightarrow{SOCl_2} J-X'$$
$$XVI \qquad\qquad XIb$$

wherein
  X' is chlorine;
  J is other than $J_5$, $J_6$, $J_{10}$ or $J_{11}$; and
  L is $-CH_2-$.

There exists a wide variety of well known methods for converting alkyl alcohols to the corresponding chlorides. One of the most common procedures involves treatment of the alcohols with thionyl chloride either alone or in the presence of a suitable base such as pyridine. For relevant examples, see the following references: H. Gilman and J. E. Kirby, *J. Am. Chem. Soc.*, 51, 3475 (1929); H. Gilman and A. P. Hewlett, *Rec. Trav. Chim.*, 51, 93 (1932); or M. S. Newman, *J. Am. Chem. Soc.*, 62, 2295 (1940).

The requisite benzyl alcohols of Formula XVI (shown below in Equation 13 for the specific example of $J=J_{16}$) can be synthesized by reduction of the appropriately substituted benzoic acid derivatives of Formula XVII with diborane in a solvent such as tetrahydrofuran.

Equation 13

[Structure XVII: benzene ring with H, $R_1$, $CO_2H$ substituents and side chain with $Q_1$, $R_3$, $R_4$] $\xrightarrow[\text{THF}]{BH_3}$ [Structure XVI: benzene ring with H, $R_1$, $CO_2OH$ substituents and side chain with $Q_1$, $R_3$, $R_4$]

wherein
  $R_1$, $R_3$, $R_4$ and $Q_1$ are as previously defined.

Although the reaction of Equation 13 is shown specifically for $J=J_{16}$, this reduction is applicable to ring systems $J_1$, $J_2$, $J_3$, $J_4$, $J_{13}$, $J_{14}$, $J_{15}$, $J_{18}$, $J_{19}$, $J_{20}$ and $J_{21}$ where L is —CH$_2$—. For a description of the use of diborane for reduction of benzoic acid derivatives, see H. C. Brown, *J. Org. Chem.*, 38, 2786 (1973).

Alternatively, benzyl alcohols of Formula XVI (shown below in Equation 14 for the specific example of J=J$_{16}$) can be synthesized by reduction of the appropriately substituted benzaldehyde derivatives of Formula XVIII with sodium borohydride in a solvent such as ethanol.

Equation 14

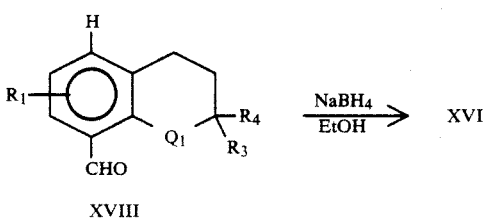

XVIII wherein
R$_1$, R$_3$, R$_4$ and Q$_1$ are as previously defined.

Although the reaction of Equation 14 is shown specifically for J=J$_{16}$, this reduction is applicable to ring systems J$_1$, J$_2$, J$_3$, J$_4$, J$_7$, J$_8$, J$_9$, J$_{12}$, J$_{13}$, J$_{14}$, J$_{15}$, J$_{17}$, J$_{18}$, J$_{19}$, J$_{20}$ and J$_{21}$ where L is —CH$_2$—. For a description of the use of sodium borohydride for the selective reduction of aldehydes, see S. Chaikin and W. Brown, *J. Am. Chem. Soc.*, 71, 122 (1949).

The aldehydes of Formula XVIII can be prepared by the procedure shown in Equation 15 starting with the appropriate nitriles of Formula XIX (shown for the specific example of J=J$_{16}$).

Equation 15 wherein
R$_1$, R$_3$, R$_4$ and Q$_1$ are as previously defined.

Although the reaction of Equation 15 is shown specifically for J=J$_{16}$, this transformation is equally applicable to all of the ring systems (L=—CH$_2$—) except J$_5$, J$_6$, J$_{10}$, and J$_{11}$. The reaction shown in Equation 15 can be carried out according to the procedures of H. C. Brown, C. J. Shoaf, and C. P. Garg, *Tetrahedron Lett.*, 9 (1959), and J. A. Marshall, N. H. Andersen, and J. W. Schlicher, *J. Org. Chem.*, 35, 858 (1970).

Benzoic acid derivatives of Formula XVII (shown below in Equation 16 for the specific example of J=J$_{16}$) can be prepared by hydrolysis of the appropriate nitriles of Formula XIX which are, in turn, prepared by a Sandmeyer reaction on the corresponding aniline derivatives XX.

Equation 16

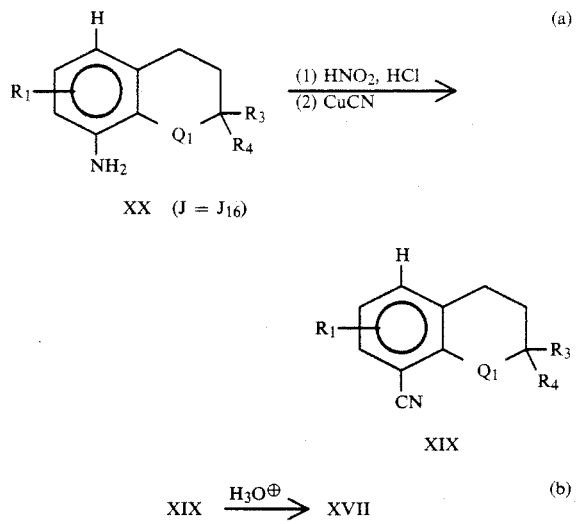

wherein
R$_1$, R$_3$, R$_4$ and Q$_1$ are as previously defined.

As before, while the reactions of Equation 16 are shown specifically for J=J$_{16}$, these steps are applicable to all ring systems where J is other than J$_5$, J$_6$, J$_{10}$ and J$_{11}$, and L is —CH$_2$—.

Equation 16(a)

The diazotization and cuprous cyanide coupling reaction of Equation 16(a) is best carried out according to the procedure described in *Organic Syntheses* Coll. Vol. I, p. 514.

Equation 16(b)

Nitriles of Formula XIX are most easily hydrolyzed to the desired carboxylic acids XVII by heating at reflux temperature in concentrated solutions of sulfuric acid or by treatment with 100% phosphoric acid and subsequent exposure to nitrous acid. The products are typically isolated by extraction into aqueous base solution followed by washing with a suitable organic solvent such as ether and acidification of the water layer. For a compilation of references dealing with this process, see R. Wagner and H. Zook, "Synthetic Organic Chemistry," John Wiley & Sons, Inc., New York, 1953, p. 412.

A method similar to that described in Equation 16 above can be applied to the synthesis of phenols of Formula VIII as shown below in Equation 17 (shown for the specific example of J=J$_{16}$).

Equation 17

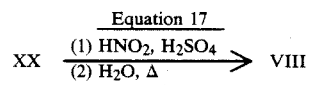

wherein
R$_1$, R$_3$, R$_4$ and Q$_1$ are as previously defined.

The reaction of Equation 17 is applicable to ring systems J$_1$, J$_2$, J$_3$, J$_4$, J$_5$, J$_6$, J$_7$, J$_8$, J$_9$, J$_{10}$, J$_{11}$, J$_{12}$, J$_{13}$, J$_{14}$, J$_{16}$, J$_{18}$, J$_{20}$ and J$_{21}$ where L is 0. The diazotization and hydrolysis reactions shown in Equation 17 can be carried out according to the following procedures: Stevens and Beutel, *J. Am. Chem. Soc.*, 63, 311 (1941); Grillot and Gormley, *J. Am. Chem. Soc.*, 67, 1968 (1945); and Mosettig and Stuart, *J. Am. Chem. Soc.*, 61, 1 (1939).

The requisite aniline derivatives of Formula XX can be prepared in a straightforward manner by reduction of the corresponding nitro compounds of Formula XXI as shown in Equation 18 (for the example where $J=J_{16}$).

Equation 18

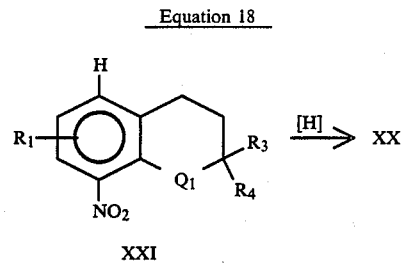

wherein
$R_1$, $R_3$, $R_4$, and Q are as previously defined.

Although the reaction of Equation 18 is shown specifically for $J=J_{16}$, this reduction is applicable to all ring systems $J_1-J_{21}$. There exists a wide variety of methods for effecting the reduction of aromatic nitro groups to the corresponding aniline derivatives. One of the more common procedures involves treating the nitro compounds of Formula XXI with a slight excess of stannous chloride dihydrate in concentrated hydrochloric acid solution at temperatures between 25° and 80° C. Alternatively, reduction may be accomplished with iron powder in glacial acetic acid solution as described by Hazlet and Dornfeld, *J. Am. Chem. Soc.*, 66, 1781 (1944), and by West in *J. Chem. Soc.*, 127, 494 (1925). For a general review, see Groggins, "Unit Processes In Organic Synthesis," McGraw-Hill Book Co., New York, 1947, pp. 73-128.

Many of the substituted aromatic nitro compounds of Formula XXI (where it is understood that all ring systems defined in the Summary of Invention are represented) can be synthesized by methods taught in U.S. patent application No. 499,443, filed on May 31, 1983, or by any of several possible synthetic routes known to one skilled in the art.

The intermediate functionalized toluene derivatives of Formula XV ($L=-CH_2-$) may also be prepared by straightforward synthetic routes known to one skilled in the art.

The synthesis of heterocyclic amines such as these depicted by Formula III has been reviewed in "The Chemistry of Heterocyclic Compounds," a series published by Interscience Publ., New York and London. Aminopyrimidines are described by D. J. Brown in "The Pyrimidines," Vol. XVI of the series mentioned above. The 2-amino-1,3,5-triazines can be prepared according to the method described by E. M. Smolin and L. Rapaport in "s-Triazines and Derivatives," Vol. XIII.

Agriculturally suitable salts of compounds of Formula I are also useful herbicides and can be prepared in a number of ways known to the art. For example, metal salts can be made by treating compounds of Formula I with a solution of an alkali or alkaline earth metal salt having a sufficiently basic anion (e.g., hydroxide, alkoxide, carbonate or hydride). Quaternary amine salts can be made by similar techniques. Detailed examples of such techniques are given in U.S. Pat. No. 4,127,405.

The compounds of this invention and their preparation are further illustrated by the following examples wherein temperatures are given in degrees centigrade and all parts are by weight unless otherwise designated.

EXAMPLE 1

2,6-Dimethylbenzoic acid, methyl ester

A solution of 10 g of 2,6-dimethylbenzoic acid in 22 g thionyl chloride was stirred at reflux temperature for 2 hours. Removal of the excess thionyl chloride afforded the crude acid chloride as a yellow oil. This intermediate was added to a stirred solution of 4 mL of methanol in 10.8 mL pyridine at 65°-70° C. After completion of the addition, the resulting mixture was stirred at room temperature for 2 hours and then poured into 75 mL ice-water. The aqueous layer was extracted with four 50-mL portions of ether and the combined organic extracts were backwashed with saturated sodium bicarbonate solution, 5% aqueous hydrochloric acid, and water. Drying and evaporation of the solvent gave a pale yellow oil which was purified by bulb-to-bulb distillation (40°-50° C., 0.5 mm Hg) to afford 9.5 g of pure 2,6-dimethylbenzoic acid, methyl ester as a colorless liquid; IR (film) 1725 cm$^{-1}$; NMR(CDCl$_3$) δ 2.3 (s, 6H), 3.9 (s, 3H), 7.0-7.4 (m, 3H).

EXAMPLE 2

2,6-Bis(α,α'-bromomethyl)benzoic acid, methyl ester

A mixture of 5.0 g of the product from Example 1, 11.1 g of N-bromosuccinimide and 0.1 g of azoisobutyronitrile in 76 mL carbon tetrachloride was heated at reflux temperature for one hour. The solution was cooled to room temperature, filtered, and the filtrate concentrated in vacuo to give a light orange oil. Treatment with ether-hexane (1:1, v/v) afforded 3.0 g of pure 2,6-bis(α,α'-bromomethyl)benzoic acid, methyl ester as a white solid, m.p. 67°-70° C.; IR(nujol) 1720 cm$^{-1}$; NMR(CDCl$_3$) δ 4.0 (s, 3H), 4.65 (s, 4H), 7.5 (s, 3H).

EXAMPLE 3

7-Bromomethylphthalide

The product from Example 2 (2.0 g) was added to 8 mL of concentrated sulfuric acid and the suspension was warmed to about 60° C. for 3 hours. The solution was allowed to cool and was poured into ice-water. The resulting white precipitate was collected by filtration, washed well with water and dried. Recrystallization from acetone gave 1.0 g of pure 7-bromomethylphthalide as a white powder, m.p. 127.5°-131° C.; IR(KBr) 1755 cm$^{-1}$; NMR(CDCl$_3$) δ 5.0 (s, 2H), 5.29 (s, 2H), 7.4 (br d, 1H), 7.5 (br d, 1H), 7.6 (dd, 1H).

EXAMPLE 4

7-[[(Amino)(imino)methyl]thiomethyl]phthalide

A solution of 1.0 g of the product from Example 3 in 10 mL tetrahydrofuran was treated with 0.33 g of thiourea and the suspension was warmed to reflux temperature for 15 minutes as a thick, white precipitate formed. The reaction mixture was allowed to cool and was filtered. The collected solid was washed with 1-chlorobutane and dried. The yield of the pure title compound was 1.2 g as a white powder, m.p. 206°-211° C. (dec.); NMR(DMSO-d$_6$) δ 4.8 (s, 2H), 5.4 (s, 2H), 7.61 (br t, 2H), 7.73 (br t, 1H), 9.1 (brs, 1H), 9.23 (br s, 2H).

EXAMPLE 5

1,3-Dihydro-1-oxo-benzo[c]furan-7-methanesulfonyl chloride

A solution of 9.4 g of the product from Example 4 in 77 mL of 50% aqueous acetic acid was cooled to 0° C. and treated with 8 mL of liquid chlorine. Following the addition, the mixture was stirred at 0°–10° C. for 2 hours, filtered, and the solid was washed well with water. The yield of 1,3-dihydro-1-oxo-benzo[c]furan-7-methanesulfonyl chloride was 5.6 g as an off-white solid, m.p. 103°–105.5° C. (dec); IR(KBr) 1740, 1355, 1200 cm$^{-1}$.

EXAMPLE 6

1,3-Dihydro-1-oxo-benzo[c]furan-7-methanesulfonamide

A solution of 5.6 g of the product from Example 5 in 50 mL tetrahydrofuran was cooled to 0° C. under an atmosphere of nitrogen and was treated with 1.5 mL of anhydrous ammonia. The resulting suspension was stirred at room temperature for 3 hours. The insoluble solids were collected by filtration and were washed with water and dried. The yield of the title compound was 3.8 g as a white powder, m.p. 192°–195° C.; IR(KBr) 3340, 3240, 1740, 1130 cm$^{-1}$; NMR(DMSO-d$_6$/CDCl$_3$) δ 4.9 (s, 2H), 5.4 (s, 2H), 6.7 (br s, 2H) 7.5–7.8 (m, 3H).

EXAMPLE 7

1,3-Dihydro-1-oxo-benzo[c]furan-7-methanesulfonyl isocyanate

A solution of 2.0 g of the product from Example 6 in 25 mL thionyl chloride was heated at reflux temperature for 18 hours. The reaction solution was allowed to cool to room temperature and excess thionyl chloride was removed in vacuo. The resulting residue was treated with 16 g of 10% phosgene in toluene and 5 drops of pyridine. This mixture was stirred at reflux temperature for 3 hours. The solution was allowed to cool, filtered under a stream of nitrogen, and the filtrate was concentrated to give 1,3-dihydro-1-oxobenzo[c]furan-7-methanesulfonyl isocyanate as an orange oil. The infrared spectrum of this compound displayed a characteristic isocyanate stretching absorption at 2240 cm$^{-1}$ as well as a carbonyl stretching signal at 1750 cm$^{-1}$.

EXAMPLE 8

1,3-Dihydro-N-[(4,6-dimethoxyprimidine-2-yl)aminocarbonyl]-1-oxo-benzo[c]furan-7-methanesulfonamide A solution of 8 mmole of the product from Example 7 in 16 mL dry acetonitrile was treated with 1.2 g of 2-amino-4,6-dimethoxypyrimidine and the mixture was heated to 45°–50° C. under an atmosphere of nitrogen for 2 hours. After being stirred at room temperature for an additional 12 hours, the suspension was filtered and the collected solid was washed well with warm acetonitrile. The yield of the title compound was 1.0 g as a yellow powder, m.p. 181°–184° C. (dec.); IR(KBr) 1765, 1710, 1620, 1355 cm$^{-1}$; NMR(CDCl$_3$) δ 3.83 (s, 6H), 5.27 (s, 2H), 5.41 (s, 2H), 5.76 (s, 1H), 7.35 (br s, 1H), 7.5 (m, 1H), 7.7 (m, 2H), 12.4 (br s, 1H).

General Formulas for Tables 1–7

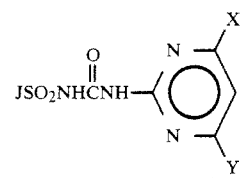

General Formula 1

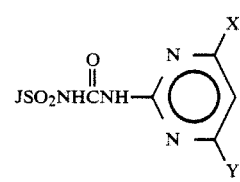

General Formula 1a

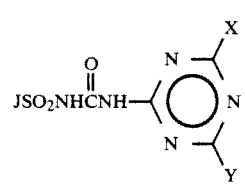

General Formula 2

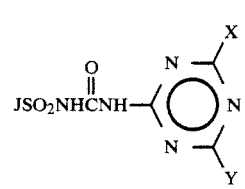

General Formula 2a

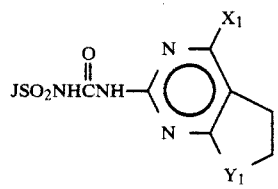

General Formula 3

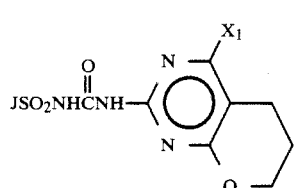

General Formula 4

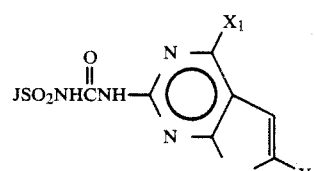

General Formula 5

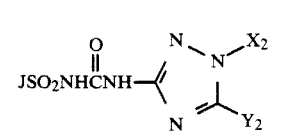

General Formula 6

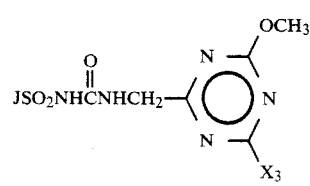

General Formula 7

By applying the procedures of Examples 1 through 8, the compounds shown in Tables 1 and 2, following, can be prepared.

TABLE 1

General Formula 1

| J | n | L | $R_1$ | $R_9$ | X | Y | m.p. (°C.) |
|---|---|---|---|---|---|---|---|
| $J_1$ | 0 | $CH_2$ | H | $CH_3$ | $CH_3$ | $OCH_3$ | |
| $J_1$ | 0 | $CH_2$ | H | $CH_3$ | $OCH_3$ | $OCH_3$ | |
| $J_1$ | 0 | $CH_2$ | H | $CH_3$ | $CH_3$ | $CH_3$ | |
| $J_1$ | 0 | $CH_2$ | H | $CH_3$ | $OCH_3$ | $C_2H_5$ | |
| $J_1$ | 0 | $CH_2$ | H | $CH_3$ | $CH_3$ | $OC_2H_5$ | |
| $J_1$ | 0 | $CH_2$ | H | $CH_3$ | $OCH_3$ | $CH_2OCH_3$ | |
| $J_1$ | 0 | $CH_2$ | H | $CH_3$ | Cl | $OCH_3$ | |
| $J_1$ | 0 | $CH_2$ | H | $CH_3$ | Br | $OCH_3$ | |
| $J_1$ | 0 | $CH_2$ | H | $CH_3$ | $OCH_3$ | $CH_2F$ | |
| $J_1$ | 0 | $CH_2$ | H | $CH_3$ | $OCH_3$ | $CF_3$ | |
| $J_1$ | 1 | $CH_2$ | H | $CH_3$ | $OCH_3$ | $OCH_3$ | |
| $J_1$ | 0 | $CH_2$ | H | $C_2H_5$ | $OCH_3$ | $OCH_3$ | |
| $J_1$ | 0 | $CH_2$ | H | n-$C_3H_7$ | $OCH_3$ | $OCH_3$ | |
| $J_1$ | 0 | $CH_2$ | H | $CH(CH_3)_2$ | $OCH_3$ | $OCH_3$ | |
| $J_1$ | 0 | $CH_2$ | H | H | $CH_3$ | $CH_3$ | |
| $J_1$ | 0 | $CH_2$ | H | H | $OCH_3$ | $OCH_3$ | |
| $J_1$ | 0 | $CH_2$ | H | H | $CH_3$ | $OCH_3$ | |
| $J_1$ | 0 | $CH_2$ | H | H | $OCH_3$ | Cl | |
| $J_1$ | 0 | O | H | H | $CH_3$ | $CH_3$ | |
| $J_1$ | 0 | O | H | H | $CH_3$ | $OCH_3$ | |
| $J_1$ | 0 | O | H | H | $OCH_3$ | $OCH_3$ | |
| $J_1$ | 0 | O | H | H | $OCH_3$ | Cl | |
| $J_1$ | 0 | O | H | $CH_3$ | $OCH_3$ | $OCH_3$ | |
| $J_1$ | 0 | O | H | $CH_3$ | $CH_3$ | $OCH_3$ | |
| $J_1$ | 0 | O | H | $CH_3$ | $CH_3$ | $CH_3$ | |
| $J_1$ | 0 | O | H | $CH_3$ | Cl | $OCH_3$ | |
| $J_1$ | 0 | O | H | $CH_3$ | Br | $OCH_3$ | |
| $J_1$ | 0 | O | H | $C_2H_5$ | $OCH_3$ | $OCH_3$ | |
| $J_1$ | 0 | O | H | n-$C_3H_7$ | $OCH_3$ | $OCH_3$ | |
| $J_1$ | 0 | O | H | $CH(CH_3)_2$ | $OCH_3$ | $OCH_3$ | |
| $J_1$ | 0 | O | H | $CH_3$ | $OCH_3$ | $OCH_3$ | |
| $J_1$ | 0 | $CH_2$ | 5-F | $CH_3$ | $OCH_3$ | $OCH_3$ | |
| $J_1$ | 0 | $CH_2$ | 6-Cl | $CH_3$ | $OCH_3$ | $OCH_3$ | |
| $J_1$ | 0 | $CH_2$ | 6-Br | $CH_3$ | $OCH_3$ | $OCH_3$ | |
| $J_1$ | 0 | $CH_2$ | 6-$CH_3$ | $CH_3$ | $OCH_3$ | $OCH_3$ | |
| $J_1$ | 0 | $CH_2$ | 6-$OCH_3$ | $CH_3$ | $OCH_3$ | $OCH_3$ | |
| $J_1$ | 0 | O | H | $CH_3$ | $OCH_2CF_3$ | $CH_3$ | |
| $J_1$ | 0 | O | H | $CH_3$ | $OCHF_2$ | $OCH_3$ | |
| $J_1$ | 0 | O | H | $CH_3$ | $OCH_3$ | $CH(CH_3)_2$ | |
| $J_1$ | 0 | O | H | $CH_3$ | $OCH_3$ | cyclopropyl | |
| $J_1$ | 0 | O | H | $CH_3$ | $OCH_3$ | C≡CH | |
| $J_1$ | 0 | O | H | $CH_3$ | $OCH_3$ | $NH_2$ | |
| $J_1$ | 0 | O | H | $CH_3$ | $OCH_3$ | $N(CH_3)_2$ | |
| $J_1$ | 0 | O | H | $CH_3$ | $OCH_3$ | $OCH_2CH_2F$ | |
| $J_1$ | 0 | O | H | $CH_3$ | $OCH_3$ | $SCH_3$ | |
| $J_1$ | 0 | O | H | $CH_3$ | $OCH_3$ | $OCH_2CH=CH_2$ | |
| $J_1$ | 0 | O | H | $CH_3$ | $OCH_3$ | $OCH_2CH_2OCH_3$ | |
| $J_1$ | 0 | O | H | $CH_3$ | $OCH_3$ | $OCH_2C≡CH$ | |
| $J_1$ | 0 | O | H | $CH_3$ | $OCH_3$ | $CH(OCH_3)_2$ | |
| $J_1$ | 0 | O | H | $CH_3$ | $OCH_3$ | $C(CH_3)(OCH_3)_2$ | |
| $J_1$ | 0 | O | H | $CH_3$ | $OCH_3$ | 1,3-dioxolan-2-yl | |
| $J_1$ | 0 | O | H | $CH_3$ | $OCH_3$ | 2-methyl-1,3-dioxolan-2-yl | |
| $J_1$ | 0 | O | H | $CH_3$ | $OCH_3$ | $CH(OC_2H_5)_2$ | |
| $J_1$ | 0 | O | H | $CH_3$ | $OCH_3$ | $C(CH_3)(OC_2H_5)_2$ | |
| $J_1$ | 0 | O | H | $CH_3$ | $OCH_3$ | $NHCH_3$ | |
| $J_1$ | 0 | O | H | $CH_3$ | Cl | $NHCH_3$ | |
| $J_1$ | 0 | O | H | —$CH_2CN$ | $OCH_3$ | $OCH_3$ | |
| $J_1$ | 0 | O | H | —$(CH_2)_3CN$ | $CH_3$ | $OCH_3$ | |
| $J_1$ | 0 | $CH_2$ | H | OH | $CH_3$ | $OCH_3$ | |
| $J_1$ | 0 | $CH_2$ | H | —$(CH_2)_3CH(CH_3)_2$ | Cl | $OCH_3$ | |
| $J_1$ | 0 | $CH_2$ | H | —$CF_2H$ | $OCH_3$ | $OCH_3$ | |
| $J_1$ | 0 | $CH_2$ | H | —$CH_2CH_2Cl$ | Cl | $OCH_3$ | |
| $J_1$ | 0 | $CH_2$ | H | —$(CH_2)_5Cl$ | $CH_3$ | $OCH_3$ | |
| $J_1$ | 0 | $CH_2$ | H | —$CH_2OCH_3$ | Cl | $OCH_3$ | |
| $J_1$ | 0 | $CH_2$ | H | —$(CH_2)_4OCH_3$ | $CH_3$ | $OCH_3$ | |
| $J_1$ | 0 | $CH_2$ | H | —$CH_2CH=CH_2$ | $OCH_3$ | $OCH_3$ | |
| $J_1$ | 0 | $CH_2$ | H | —$CH_2CH=CHCH_3$ | $CH_3$ | $OCH_3$ | |
| $J_1$ | 0 | $CH_2$ | H | —$CH_2C≡CH$ | $OCH_3$ | $OCH_3$ | |
| $J_1$ | 0 | $CH_2$ | H | —$CH_2C≡C—CH_3$ | Cl | $OCH_3$ | |
| $J_1$ | 0 | $CH_2$ | H | —$(CH_2)_4C≡CH$ | $CH_3$ | $OCH_3$ | |
| $J_1$ | 0 | $CH_2$ | H | —$OCH_3$ | $CH_3$ | $OCH_3$ | |
| $J_1$ | 0 | $CH_2$ | H | —$O(CH_2)_4CH_3$ | Cl | $OCH_3$ | |
| $J_1$ | 0 | $CH_2$ | H | —$C_6H_5$ | $CH_3$ | $OCH_3$ | |

TABLE 1-continued

General Formula 1

| J | n | L | $R_1$ | $R_9$ | X | Y | m.p. (°C.) |
|---|---|---|---|---|---|---|---|
| $J_1$ | 0 | $CH_2$ | H | cyclopropyl | $OCH_3$ | $OCH_3$ | |
| $J_1$ | 0 | $CH_2$ | H | cyclohexyl | $OCH_3$ | $OCH_3$ | |
| $J_1$ | 0 | $CH_2$ | H | cyclopropylmethyl | $OCH_3$ | $OCH_3$ | |
| $J_1$ | 0 | $CH_2$ | H | cyclohexylmethyl | Cl | $OCH_3$ | |
| $J_1$ | 0 | $CH_2$ | H | —C(O)$CH_3$ | $OCH_3$ | $OCH_3$ | |
| $J_1$ | 0 | $CH_2$ | H | —C(O)($CH_2)_5$H | Cl | $OCH_3$ | |
| $J_1$ | 0 | $CH_2$ | H | —$CO_2C_2H_5$ | Br | $OCH_3$ | |
| $J_1$ | 0 | $CH_2$ | H | —$CO_2(CH_2)_4$H | Cl | $OCH_3$ | |
| $J_1$ | 0 | $CH_2$ | H | —$CH_2C_6H_5$ | $OCH_3$ | $OCH_3$ | |
| $J_1$ | 0 | $CH_2$ | H | —$CH_2$—CH=CH—$CH_2$Cl | $CH_3$ | $OCH_3$ | |
| $J_1$ | 0 | $CH_2$ | H | —$CH_2$C≡C—$CH_2$Cl | Cl | $OCH_3$ | |
| $J_1$ | 0 | $CH_2$ | H | —$CH_2$C(O)$CH_3$ | $OCH_3$ | $OCH_3$ | |
| $J_1$ | 0 | $CH_2$ | H | —CH($CH_3$)$CO_2C_2H_5$ | $OCH_3$ | $OCH_3$ | |
| $J_1$ | 0 | $CH_2$ | H | H | $CH_3$ | $OCH_3$ | |
| $J_1$ | 0 | $CH_2$ | H | H | $CH_3$ | $CH_3$ | |
| $J_1$ | 0 | $CH_2$ | H | H | Cl | $OCH_3$ | |
| $J_1$ | 0 | O | H | H | $OCH_3$ | $OCH_3$ | |
| $J_1$ | 0 | O | H | H | $CH_3$ | $OCH_3$ | |
| $J_1$ | 0 | O | H | H | $CH_3$ | $CH_3$ | |
| $J_1$ | 0 | O | H | H | Cl | $OCH_3$ | |
| $J_1$ | 0 | $CH_2$ | H | n-$C_4H_9$ | $CH_3$ | $CH_3$ | |
| $J_1$ | 0 | $CH_2$ | H | n-$C_4H_9$ | $CH_3$ | $OCH_3$ | |
| $J_1$ | 0 | $CH_2$ | H | n-$C_4H_9$ | $OCH_3$ | $OCH_3$ | |
| $J_1$ | 0 | $CH_2$ | H | n-$C_4H_9$ | Cl | $OCH_3$ | |
| $J_1$ | 0 | O | H | n-$C_4H_9$ | $CH_3$ | $CH_3$ | |
| $J_1$ | 0 | O | H | n-$C_4H_9$ | $CH_3$ | $OCH_3$ | |
| $J_1$ | 0 | O | H | n-$C_4H_9$ | $OCH_3$ | $OCH_3$ | |
| $J_1$ | 0 | O | H | n-$C_4H_9$ | Cl | $OCH_3$ | |
| $J_7$ | — | $CH_2$ | H | $CH_3$ | $OCH_3$ | $OCH_3$ | |
| $J_7$ | — | $CH_2$ | H | $CH_3$ | $OCH_3$ | $CH_3$ | |
| $J_7$ | — | $CH_2$ | H | $CH_3$ | $CH_3$ | $CH_3$ | |
| $J_7$ | — | $CH_2$ | H | $CH_3$ | Cl | $OCH_3$ | |
| $J_7$ | — | $CH_2$ | H | $CH_3$ | Br | $OCH_3$ | |
| $J_7$ | — | $CH_2$ | H | $CH_3$ | $OCH_3$ | $C_2H_5$ | |
| $J_7$ | — | $CH_2$ | H | $CH_3$ | $CH_3$ | $OC_2H_5$ | |
| $J_7$ | — | $CH_2$ | H | $CH_3$ | $OCH_3$ | $CH_2OCH_3$ | |
| $J_7$ | — | $CH_2$ | H | $CH_3$ | $OCH_3$ | $CH_2F$ | |
| $J_7$ | — | $CH_2$ | H | $CH_3$ | $OCH_3$ | $CF_3$ | |
| $J_7$ | — | $CH_2$ | H | H | $OCH_3$ | $OCH_3$ | |
| $J_7$ | — | $CH_2$ | H | $C_2H_5$ | $OCH_3$ | $OCH_3$ | |
| $J_7$ | — | $CH_2$ | H | n-$C_3H_7$ | $OCH_3$ | $OCH_3$ | |
| $J_7$ | — | $CH_2$ | H | CH($CH_3)_2$ | $OCH_3$ | $OCH_3$ | |
| $J_7$ | — | O | H | $CH_3$ | $OCH_3$ | $OCH_3$ | |
| $J_7$ | — | $CH_2$ | 7-Cl | $CH_3$ | $OCH_3$ | $OCH_3$ | |
| $J_7$ | — | O | 7-Br | $CH_3$ | $OCH_3$ | $OCH_3$ | |
| $J_7$ | — | $CH_2$ | 6-F | $CH_3$ | $OCH_3$ | $OCH_3$ | |
| $J_7$ | — | O | 7-$CH_3$ | $CH_3$ | $OCH_3$ | $OCH_3$ | |
| $J_7$ | — | O | 7-$OCH_3$ | $CH_3$ | $OCH_3$ | $OCH_3$ | |
| $J_7$ | — | $CH_2$ | H | $CH_3$ | $OCH_2CF_3$ | $OCH_3$ | |
| $J_7$ | — | $CH_2$ | H | $CH_3$ | $OCHF_2$ | $OCH_3$ | |
| $J_7$ | — | $CH_2$ | H | $CH_3$ | $OCH_3$ | cyclopropyl | |
| $J_7$ | — | $CH_2$ | H | $CH_3$ | $OCH_3$ | $NHCH_3$ | |
| $J_7$ | — | $CH_2$ | H | $CH_3$ | $OCH_3$ | $N(CH_3)_2$ | |
| $J_7$ | — | $CH_2$ | H | $CH_3$ | $OCH_3$ | $OCH_2CH=CH_2$ | |
| $J_7$ | — | $CH_2$ | H | $CH_3$ | $OCH_3$ | $CH(OCH_3)_2$ | |
| $J_7$ | — | $CH_2$ | H | $CH_3$ | $OCH_3$ | 1,3-dioxolan-2-yl | |
| $J_7$ | — | $CH_2$ | H | $CH_3$ | $OCH_3$ | $CH(OC_2H_5)_2$ | |
| $J_7$ | — | $CH_2$ | H | $CH_3$ | Cl | $NHCH_3$ | |
| $J_7$ | — | $CH_2$ | H | $CH_3$ | $OCH_3$ | —C≡CH | |
| $J_7$ | — | $CH_2$ | H | $CH_3$ | $OCH_3$ | C($CH_3$)($OCH_3)_2$ | |
| $J_7$ | — | $CH_2$ | H | OH | $OCH_3$ | $OCH_3$ | |
| $J_7$ | — | $CH_2$ | H | $(CH_2)_2$CH($CH_3)_2$ | Cl | $OCH_3$ | |
| $J_7$ | — | $CH_2$ | H | $CH_2CH_2$Cl | $OCH_3$ | $OCH_3$ | |
| $J_7$ | — | $CH_2$ | H | $(CH_2)_5$Cl | $CH_3$ | $OCH_3$ | |
| $J_7$ | — | $CH_2$ | H | $CH_2OCH_3$ | Cl | $OCH_3$ | |
| $J_7$ | — | $CH_2$ | H | $(CH_2)_2OCH_3$ | Cl | $OCH_3$ | |
| $J_7$ | — | $CH_2$ | H | $CH_2CH=CH_2$ | $OCH_3$ | $OCH_3$ | |
| $J_7$ | — | $CH_2$ | H | $CH_2CH=CHCH_2$Cl | $CH_3$ | $OCH_3$ | |
| $J_7$ | — | $CH_2$ | H | $CH_2CH=CHCH_3$ | $CH_3$ | $OCH_3$ | |
| $J_7$ | — | $CH_2$ | H | $CH_2$C≡$CCH_3$ | $OCH_3$ | $OCH_3$ | |
| $J_7$ | — | $CH_2$ | H | $OCH_3$ | Cl | $OCH_3$ | |
| $J_7$ | — | $CH_2$ | H | O($CH_2)_4CH_3$ | Cl | $OCH_3$ | |
| $J_7$ | — | $CH_2$ | H | $C_6H_5$ | $OCH_3$ | $OCH_3$ | |
| $J_7$ | — | $CH_2$ | H | cyclopropyl | Cl | $OCH_3$ | |
| $J_7$ | — | $CH_2$ | H | cyclopentyl | $OCH_3$ | $OCH_3$ | |
| $J_7$ | — | $CH_2$ | H | C(O)$CH_3$ | $OCH_3$ | $OCH_3$ | |
| $J_7$ | — | $CH_2$ | H | $CO_2CH_3$ | $OCH_3$ | $OCH_3$ | |
| $J_7$ | — | $CH_2$ | H | $CH_2C_6H_5$ | Cl | $OCH_3$ | |

TABLE 1-continued

General Formula 1

| J | n | L | $R_1$ | $R_9$ | X | Y | m.p. (°C.) |
|---|---|---|---|---|---|---|---|
| $J_7$ | — | $CH_2$ | H | $CH_2CH=CHCl$ | Cl | $OCH_3$ | |
| $J_7$ | — | $CH_2$ | H | $CH(CH_3)CO_2CH_3$ | Cl | $OCH_3$ | |

TABLE 1a

General Formula 1a

| J | n | L | Q | $Q_1$ | $Q_2$ | $R_1$ | $R_2$ | $R_3$ | $R_4$ | $R_5$ | $R_6$ | $R_7$ | $R_8$ | X | Y | m.p. (°C.) |
|---|---|---|---|---|---|---|---|---|---|---|---|---|---|---|---|---|
| $J_2$ | 0 | $CH_2$ | — | — | — | H | $CH_3$ | — | — | — | — | — | — | $OCH_3$ | $OCH_3$ | |
| $J_2$ | 0 | $CH_2$ | — | — | — | H | $CH_3$ | — | — | — | — | — | — | $OCH_3$ | $CH_3$ | |
| $J_2$ | 0 | $CH_2$ | — | — | — | H | $CH_3$ | — | — | — | — | — | — | Cl | $OCH_3$ | |
| $J_2$ | 0 | $CH_2$ | — | — | — | H | $CH_3$ | — | — | — | — | — | — | Br | $OCH_3$ | |
| $J_2$ | 0 | $CH_2$ | — | — | — | H | $CH_3$ | — | — | — | — | — | — | $OCH_3$ | $C_2H_5$ | |
| $J_2$ | 0 | $CH_2$ | — | — | — | H | $CH_3$ | — | — | — | — | — | — | $CH_3$ | $OC_2H_5$ | |
| $J_2$ | 0 | $CH_2$ | — | — | — | H | $CH_3$ | — | — | — | — | — | — | $OCH_3$ | $CH_2OCH_3$ | |
| $J_2$ | 0 | $CH_2$ | — | — | — | H | $CH_3$ | — | — | — | — | — | — | $OCH_3$ | $CH_2F$ | |
| $J_2$ | 0 | $CH_2$ | — | — | — | H | $CH_3$ | — | — | — | — | — | — | $OCH_3$ | $CF_3$ | |
| $J_2$ | 0 | $CH_2$ | — | — | — | H | H | — | — | — | — | — | — | $OCH_3$ | $OCH_3$ | |
| $J_2$ | 0 | $CH_2$ | — | — | — | H | $C_2H_5$ | — | — | — | — | — | — | $OCH_3$ | $OCH_3$ | |
| $J_2$ | 0 | $CH_2$ | — | — | — | H | n-$C_3H_7$ | — | — | — | — | — | — | $OCH_3$ | $OCH_3$ | |
| $J_2$ | 0 | $CH_2$ | — | — | — | H | $CH(CH_3)_2$ | — | — | — | — | — | — | $OCH_3$ | $OCH_3$ | |
| $J_2$ | 1 | $CH_2$ | — | — | — | H | $CH_3$ | — | — | — | — | — | — | $OCH_3$ | $OCH_3$ | |
| $J_2$ | 0 | O | — | — | — | H | $CH_3$ | — | — | — | — | — | — | $OCH_3$ | $OCH_3$ | |
| $J_2$ | 0 | O | — | — | — | H | $CH_3$ | — | — | — | — | — | — | $OCH_3$ | $CH_3$ | |
| $J_2$ | 0 | O | — | — | — | H | $CH_3$ | — | — | — | — | — | — | Cl | $OCH_3$ | |
| $J_2$ | 0 | O | — | — | — | H | $CH_3$ | — | — | — | — | — | — | Br | $OCH_3$ | |
| $J_2$ | 1 | O | — | — | — | H | $CH_3$ | — | — | — | — | — | — | $OCH_3$ | $OCH_3$ | |
| $J_2$ | 0 | O | — | — | — | H | $C_2H_5$ | — | — | — | — | — | — | $OCH_3$ | $OCH_3$ | |
| $J_2$ | 0 | $CH_2$ | — | — | — | 6-Br | $CH_3$ | — | — | — | — | — | — | $OCH_3$ | $OCH_3$ | |
| $J_2$ | 0 | $CH_2$ | — | — | — | 6-Cl | $CH_3$ | — | — | — | — | — | — | $OCH_3$ | $OCH_3$ | |
| $J_2$ | 0 | $CH_2$ | — | — | — | 5-F | $CH_3$ | — | — | — | — | — | — | $OCH_3$ | $OCH_3$ | |
| $J_2$ | 0 | O | — | — | — | 6-$CH_3$ | $CH_3$ | — | — | — | — | — | — | $OCH_3$ | $OCH_3$ | |
| $J_2$ | 0 | O | — | — | — | 6-$OCH_3$ | $CH_3$ | — | — | — | — | — | — | $OCH_3$ | $OCH_3$ | |
| $J_3$ | 0 | $CH_2$ | — | — | — | H | — | H | H | — | — | — | — | $OCH_3$ | $OCH_3$ | 181–184,d |
| $J_3$ | 0 | $CH_2$ | — | — | — | H | — | H | H | — | — | — | — | $CH_3$ | $OCH_3$ | 180–185,d |
| $J_3$ | 0 | $CH_2$ | — | — | — | H | — | H | H | — | — | — | — | $CH_3$ | $CH_3$ | |
| $J_3$ | 0 | $CH_2$ | — | — | — | H | — | H | H | — | — | — | — | Cl | $OCH_3$ | |
| $J_2$ | 0 | $CH_2$ | — | — | — | H | $CH_3$ | — | — | — | — | — | — | $OCH_3$ | $CH(CH_3)_2$ | |
| $J_2$ | 0 | $CH_2$ | — | — | — | H | $CH_3$ | — | — | — | — | — | — | Cl | $NHCH_3$ | |
| $J_2$ | 0 | $CH_2$ | — | — | — | H | $CH_3$ | — | — | — | — | — | — | Cl | $OCF_2H$ | |
| $J_2$ | 0 | $CH_2$ | — | — | — | H | $CH_3$ | — | — | — | — | — | — | $OCH_2CF_3$ | $OCH_3$ | |
| $J_2$ | 0 | $CH_2$ | — | — | — | H | $CH_3$ | — | — | — | — | — | — | $OCF_2H$ | $OCF_2H$ | |
| $J_2$ | 0 | $CH_2$ | — | — | — | H | $CH_3$ | — | — | — | — | — | — | $OCH_3$ | cyclopropyl | |
| $J_2$ | 0 | $CH_2$ | — | — | — | H | $CH_3$ | — | — | — | — | — | — | $OCH_3$ | $NHCH_3$ | |
| $J_2$ | 0 | $CH_2$ | — | — | — | H | $CH_3$ | — | — | — | — | — | — | $OCH_3$ | $N(CH_3)_2$ | |
| $J_2$ | 0 | $CH_2$ | — | — | — | H | $CH_3$ | — | — | — | — | — | — | $OCH_3$ | $OCH_2CH=CH_2$ | |
| $J_2$ | 0 | $CH_2$ | — | — | — | H | $CH_3$ | — | — | — | — | — | — | $OCH_3$ | $CH(OCH_3)_2$ | |
| $J_2$ | 0 | $CH_2$ | — | — | — | H | $CH_3$ | — | — | — | — | — | — | $OCH_3$ | 1,3-dioxolan-2-yl | |
| $J_2$ | 0 | $CH_2$ | — | — | — | H | $CH_3$ | — | — | — | — | — | — | $OCH_3$ | $CH(OC_2H_5)_2$ | |
| $J_2$ | 0 | $CH_2$ | — | — | — | H | $CH_3$ | — | — | — | — | — | — | $OCH_3$ | $C\equiv CH$ | |
| $J_2$ | 0 | $CH_2$ | — | — | — | H | $CH_3$ | — | — | — | — | — | — | $OCH_3$ | $OCH_2CH_2OCH_3$ | |
| $J_2$ | 0 | $CH_2$ | — | — | — | H | $CH_3$ | — | — | — | — | — | — | $OCH_3$ | $SCH_3$ | |
| $J_2$ | 0 | $CH_2$ | — | — | — | H | $CH_3$ | — | — | — | — | — | — | $OCF_2H$ | $OCH_3$ | |
| $J_2$ | 0 | $CH_2$ | — | — | — | H | $CH_3$ | — | — | — | — | — | — | $CH_3$ | 1,3-dioxolan-2-yl | |
| $J_3$ | 0 | $CH_2$ | — | — | — | H | — | H | H | — | — | — | — | $CH_3$ | $OCH_2C\equiv CH$ | |
| $J_3$ | 0 | $CH_2$ | — | — | — | H | — | H | H | — | — | — | — | Br | $OCH_3$ | |
| $J_3$ | 0 | $CH_2$ | — | — | — | H | — | H | H | — | — | — | — | $OCH_3$ | $C_2H_5$ | |
| $J_3$ | 0 | $CH_2$ | — | — | — | H | — | H | H | — | — | — | — | $CH_3$ | $OC_2H_5$ | |
| $J_3$ | 0 | $CH_2$ | — | — | — | H | — | H | H | — | — | — | — | $CH_3$ | $CH_2OCH_3$ | |
| $J_3$ | 0 | $CH_2$ | — | — | — | H | — | H | H | — | — | — | — | $OCH_3$ | $CH_2F$ | |
| $J_3$ | 0 | $CH_2$ | — | — | — | H | — | H | H | — | — | — | — | $OCH_3$ | $CF_3$ | |
| $J_3$ | 1 | $CH_2$ | — | — | — | H | — | H | H | — | — | — | — | $OCH_3$ | $OCH_3$ | |
| $J_3$ | 1 | $CH_2$ | — | — | — | H | — | $CH_3$ | H | — | — | — | — | $OCH_3$ | $OCH_3$ | |
| $J_3$ | 0 | O | — | — | — | H | — | H | H | — | — | — | — | $OCH_3$ | $CH_3$ | |
| $J_3$ | 1 | $CH_2$ | — | — | — | H | — | $CH_3$ | H | — | — | — | — | $CH_3$ | $CH_3$ | |
| $J_3$ | 1 | $CH_2$ | — | — | — | H | — | $CH_3$ | H | — | — | — | — | $CH_3$ | $OCH_3$ | |
| $J_3$ | 1 | $CH_2$ | — | — | — | H | — | $CH_3$ | H | — | — | — | — | $OCH_3$ | $OCH_3$ | |
| $J_3$ | 1 | $CH_2$ | — | — | — | H | — | $CH_3$ | H | — | — | — | — | Cl | $OCH_3$ | |
| $J_3$ | 1 | O | — | — | — | H | — | $CH_3$ | H | — | — | — | — | $CH_3$ | $CH_3$ | |
| $J_3$ | 1 | O | — | — | — | H | — | $CH_3$ | H | — | — | — | — | $OCH_3$ | $CH_3$ | |
| $J_3$ | 1 | O | — | — | — | H | — | $CH_3$ | H | — | — | — | — | Cl | $OCH_3$ | |
| $J_3$ | 0 | $CH_2$ | — | — | — | H | — | $CH_3$ | H | — | — | — | — | $OCH_3$ | $OCH_3$ | |

TABLE 1a-continued

General Formula 1a

| J | n | L | Q | Q₁ | Q₂ | R₁ | R₂ | R₃ | R₄ | R₅ | R₆ | R₇ | R₈ | X | Y | m.p. (°C.) |
|---|---|---|---|---|---|---|---|---|---|---|---|---|---|---|---|---|
| J₃ | 0 | O | — | — | — | H | — | H | H | — | — | — | — | OCH₃ | OCH₃ | |
| J₃ | 0 | O | — | — | — | H | — | H | H | — | — | — | — | OCH₃ | CH₃ | |
| J₃ | 0 | O | — | — | — | H | — | H | H | — | — | — | — | Cl | OCH₃ | |
| J₃ | 0 | O | — | — | — | H | — | H | H | — | — | — | — | Br | OCH₃ | |
| J₃ | 0 | O | — | — | — | H | — | H | H | — | — | — | — | CH₃ | CH₃ | |
| J₃ | 0 | CH₂ | — | — | — | H | — | H | H | — | — | — | — | CH₃ | CH₃ | |
| J₃ | 0 | CH₂ | — | — | — | H | — | H | H | — | — | — | — | OCH₃ | CH₃ | |
| J₃ | 0 | CH₂ | — | — | — | H | — | H | H | — | — | — | — | OCH₃ | OCH₃ | |
| J₃ | 0 | CH₂ | — | — | — | H | — | H | H | — | — | — | — | Cl | OCH₃ | |
| J₃ | 0 | CH₂ | — | — | — | 5-F | — | H | H | — | — | — | — | OCH₃ | OCH₃ | |
| J₃ | 0 | CH₂ | — | — | — | 6-Cl | — | H | H | — | — | — | — | OCH₃ | OCH₃ | |
| J₃ | 0 | CH₂ | — | — | — | 6-Br | — | H | H | — | — | — | — | OCH₃ | OCH₃ | |
| J₃ | 0 | O | — | — | — | 5-CH₃ | — | H | H | — | — | — | — | OCH₃ | OCH₃ | |
| J₃ | 0 | O | — | — | — | 6-OCH₃ | — | H | H | — | — | — | — | OCH₃ | OCH₃ | |
| J₃ | 1 | O | — | — | — | H | — | H | H | — | — | — | — | OCH₃ | OCH₃ | |
| J₄ | 0 | CH₂ | — | — | — | H | — | — | — | — | — | — | — | OCH₃ | OCH₃ | |
| J₄ | 1 | CH₂ | — | — | — | H | — | — | — | — | — | — | — | OCH₃ | CH₃ | |
| J₄ | 0 | O | — | — | — | H | — | — | — | — | — | — | — | OCH₃ | OCH₃ | |
| J₄ | 1 | O | — | — | — | H | — | — | — | — | — | — | — | OCH₃ | OCH₃ | |
| J₄ | 0 | CH₂ | — | — | — | H | — | — | — | — | — | — | — | Cl | OCH₃ | |
| J₄ | 0 | O | — | — | — | H | — | — | — | — | — | — | — | Cl | OCH₃ | |
| J₅ | 0 | — | — | — | — | H | CH₃ | — | — | — | — | — | — | OCH₃ | OCH₃ | |
| J₅ | 0 | — | — | — | — | H | CH₃ | — | — | — | — | — | — | CH₃ | OCH₃ | |
| J₅ | 0 | — | — | — | — | H | CH₃ | — | — | — | — | — | — | CH₃ | CH₃ | |
| J₅ | 0 | — | — | — | — | H | CH₃ | — | — | — | — | — | — | Cl | OCH₃ | |
| J₅ | 1 | — | — | — | — | H | CH₃ | — | — | — | — | — | — | OCH₃ | OCH₃ | |
| J₅ | 0 | — | — | — | — | H | H | — | — | — | — | — | — | OCH₃ | OCH₃ | |
| J₆ | 0 | — | — | — | — | H | CH₃ | — | — | — | — | — | — | OCH₃ | OCH₃ | |
| J₆ | 0 | — | — | — | — | H | CH₃ | — | — | — | — | — | — | Cl | OCH₃ | |
| J₆ | 0 | — | — | — | — | H | CH₃ | — | — | — | — | — | — | CH₃ | OCH₃ | |
| J₆ | 0 | — | — | — | — | H | H | — | — | — | — | — | — | OCH₃ | OCH₃ | |
| J₆ | 1 | — | — | — | — | H | CH₃ | — | — | — | — | — | — | OCH₃ | OCH₃ | |
| J₈ | — | CH₂ | — | — | — | H | — | H | — | — | — | — | — | OCH₃ | OCH₃ | |
| J₈ | — | CH₂ | — | — | — | H | — | H | — | — | — | — | — | OCH₃ | CH₃ | |
| J₈ | — | CH₂ | — | — | — | H | — | H | — | — | — | — | — | Cl | OCH₃ | |
| J₈ | — | CH₂ | — | — | — | H | — | H | — | — | — | — | — | Br | OCH₃ | |
| J₈ | — | CH₂ | — | — | — | H | — | H | — | — | — | — | — | OCH₃ | C₂H₅ | |
| J₈ | — | CH₂ | — | — | — | H | — | H | — | — | — | — | — | CH₃ | OC₂H₅ | |
| J₈ | — | CH₂ | — | — | — | H | — | H | — | — | — | — | — | OCH₃ | CH₂OCH₃ | |
| J₈ | — | CH₂ | — | — | — | H | — | H | — | — | — | — | — | OCH₃ | CH₂F | |
| J₈ | — | CH₂ | — | — | — | H | — | H | — | — | — | — | — | OCH₃ | CF₃ | |
| J₈ | — | O | — | — | — | H | — | H | — | — | — | — | — | OCH₃ | OCH₃ | |
| J₈ | — | O | — | — | — | H | — | H | — | — | — | — | — | Cl | OCH₃ | |
| J₈ | — | CH₂ | — | — | — | 7-Cl | — | H | — | — | — | — | — | OCH₃ | OCH₃ | |
| J₉ | — | CH₂ | — | — | — | H | — | — | — | — | — | — | — | OCH₃ | OCH₃ | |
| J₉ | — | CH₂ | — | — | — | H | — | — | — | — | — | — | — | Cl | OCH₃ | |
| J₉ | — | O | — | — | — | H | — | — | — | — | — | — | — | OCH₃ | OCH₃ | |
| J₁₀ | — | — | — | — | — | H | CH₃ | — | — | — | — | — | — | OCH₃ | OCH₃ | |
| J₁₀ | — | — | — | — | — | H | CH₃ | — | — | — | — | — | — | Cl | OCH₃ | |
| J₁₀ | — | — | — | — | — | H | C₂H₅ | — | — | — | — | — | — | OCH₃ | OCH₃ | |
| J₁₁ | — | — | — | — | — | H | CH₃ | — | — | — | — | — | — | OCH₃ | OCH₃ | |
| J₁₁ | — | — | — | — | — | H | C₂H₅ | — | — | — | — | — | — | OCH₃ | OCH₃ | |
| J₁₂ | — | CH₂ | — | — | — | H | — | H | — | — | — | — | — | OCH₃ | OCH₃ | |
| J₁₂ | — | CH₂ | — | — | — | H | — | H | — | — | — | — | — | OCH₃ | CH₃ | |
| J₁₂ | — | CH₂ | — | — | — | H | — | H | — | — | — | — | — | Cl | OCH₃ | |
| J₁₂ | — | CH₂ | — | — | — | H | — | H | — | — | — | — | — | Br | OCH₃ | |
| J₁₂ | — | CH₂ | — | — | — | H | — | CH₃ | — | — | — | — | — | OCH₃ | OCH₃ | |
| J₁₂ | — | O | — | — | — | H | — | H | — | — | — | — | — | OCH₃ | OCH₃ | |
| J₁₂ | — | O | — | — | — | H | — | H | — | — | — | — | — | Cl | OCH₃ | |
| J₁₂ | — | O | — | — | — | H | — | CH₃ | — | — | — | — | — | OCH₃ | OCH₃ | |
| J₁₃ | — | CH₂ | O | — | — | H | — | — | — | — | — | — | — | OCH₃ | OCH₃ | |
| J₁₃ | — | CH₂ | O | — | — | H | — | — | — | — | — | — | — | Cl | OCH₃ | |
| J₁₃ | — | O | O | — | — | H | — | — | — | — | — | — | — | OCH₃ | OCH₃ | |
| J₁₃ | — | O | O | — | — | H | — | — | — | — | — | — | — | Cl | OCH₃ | |
| J₁₃ | — | CH₂ | CH₂ | — | — | H | — | — | — | — | — | — | — | OCH₃ | OCH₃ | |
| J₁₃ | — | CH₂ | CH₂ | — | — | H | — | — | — | — | — | — | — | Cl | OCH₃ | |
| J₁₃ | — | O | CH₂ | — | — | H | — | — | — | — | — | — | — | OCH₃ | OCH₃ | |
| J₁₃ | — | O | CH₂ | — | — | H | — | — | — | — | — | — | — | Cl | OCH₃ | |
| J₁₄ | — | CH₂ | — | — | — | H | — | — | — | — | — | — | — | OCH₃ | OCH₃ | |
| J₁₄ | — | CH₂ | — | — | — | H | — | — | — | — | — | — | — | Cl | OCH₃ | |
| J₁₄ | — | O | — | — | — | H | — | — | — | — | — | — | — | OCH₃ | OCH₃ | |
| J₁₄ | — | O | — | — | — | H | — | — | — | — | — | — | — | Cl | OCH₃ | |
| J₁₅ | — | — | — | O | — | H | — | CH₃ | H | H | — | — | — | OCH₃ | OCH₃ | |
| J₁₅ | — | — | — | O | — | H | — | CH₃ | H | H | — | — | — | OCH₃ | CH₃ | |
| J₁₅ | — | — | — | O | — | H | — | H | H | CH₃ | — | — | — | CH₃ | CH₃ | |
| J₁₅ | — | — | — | O | — | H | — | H | H | CH₃ | — | — | — | Cl | OCH₃ | |
| J₁₅ | — | — | — | O | — | H | — | CH₃ | H | H | — | — | — | Br | OCH₃ | |
| J₁₅ | — | — | — | O | — | H | — | H | H | CH₃ | — | — | — | OCH₃ | C₂H₅ | |

TABLE 1a-continued

General Formula 1a

| J | n | L | Q | Q₁ | Q₂ | R₁ | R₂ | R₃ | R₄ | R₅ | R₆ | R₇ | R₈ | X | Y | m.p. (°C.) |
|---|---|---|---|---|---|---|---|---|---|---|---|---|---|---|---|---|
| J₁₅ | — | — | — | O | — | H | — | CH₃ | H | H | — | — | — | CH₃ | OC₂H₅ | |
| J₁₅ | — | — | — | O | — | H | — | CH₃ | H | H | — | — | — | OCH₃ | CH₂OCH₃ | |
| J₁₅ | — | — | — | O | — | H | — | H | H | C₂H₅ | — | — | — | OCH₃ | CF₃ | |
| J₁₅ | — | — | — | O | — | H | — | CH₃ | CH₃ | H | — | — | — | OCH₃ | OCH₃ | |
| J₁₅ | — | — | — | O | — | H | — | CH₃ | H | CH₃ | — | — | — | OCH₃ | OCH₃ | |
| J₁₅ | — | — | — | O | — | H | — | CH₃ | H | CH₃ | — | — | — | OCH₃ | CH₃ | |
| J₁₅ | — | — | — | O | — | H | — | CH₃ | H | CH₃ | — | — | — | CH₃ | CH₃ | |
| J₁₅ | — | — | — | O | — | H | — | CH₃ | H | CH₃ | — | — | — | Cl | OCH₃ | |
| J₁₅ | — | — | — | O | — | H | — | CH₃ | H | CH₃ | — | — | — | Br | OCH₃ | |
| J₁₅ | — | — | — | O | — | H | — | CH₃ | H | CH₃ | — | — | — | OCH₃ | C₂H₅ | |
| J₁₅ | — | — | — | O | — | H | — | CH₃ | H | CH₃ | — | — | — | CH₃ | OC₂H₅ | |
| J₁₅ | — | — | — | O | — | H | — | CH₃ | H | CH₃ | — | — | — | OCH₃ | CH₂OCH₃ | |
| J₁₅ | — | — | — | O | — | H | — | CH₃ | H | CH₃ | — | — | — | OCH₃ | CH₂F | |
| J₁₅ | — | — | — | O | — | H | — | CH₃ | H | CH₃ | — | — | — | OCH₃ | CF₃ | |
| J₁₅ | — | — | — | S | — | H | — | CH₃ | H | H | — | — | — | OCH₃ | OCH₃ | |
| J₁₅ | — | — | — | S | — | H | — | CH₃ | H | H | — | — | — | OCH₃ | CH₃ | |
| J₁₅ | — | — | — | S | — | H | — | CH₃ | H | H | — | — | — | CH₃ | CH₃ | |
| J₁₅ | — | — | — | S | — | H | — | CH₃ | H | H | — | — | — | Cl | OCH₃ | |
| J₁₅ | — | — | — | S | — | H | — | CH₃ | H | H | — | — | — | Br | OCH₃ | |
| J₁₅ | — | — | — | S | — | H | — | H | CH₃ | CH₃ | — | — | — | OCH₃ | CH₃ | |
| J₁₅ | — | — | — | SO₂ | — | H | — | CH₃ | H | H | — | — | — | OCH₃ | OCH₃ | 222–222.5 |
| J₁₅ | — | — | — | SO₂ | — | H | — | CH₃ | H | H | — | — | — | OCH₃ | CH₃ | 208–209 |
| J₁₅ | — | — | — | SO₂ | — | H | — | CH₃ | H | H | — | — | — | CH₃ | CH₃ | 192–193 |
| J₁₅ | — | — | — | SO₂ | — | H | — | CH₃ | H | H | — | — | — | Cl | OCH₃ | |
| J₁₅ | — | — | — | SO₂ | — | H | — | CH₃ | H | H | — | — | — | Br | OCH₃ | |
| J₁₅ | — | — | — | SO₂ | — | H | — | CH₃ | H | H | — | — | — | OCH₃ | C₂H₅ | |
| J₁₅ | — | — | — | SO₂ | — | H | — | CH₃ | H | H | — | — | — | CH₃ | OC₂H₅ | |
| J₁₅ | — | — | — | SO₂ | — | H | — | CH₃ | H | H | — | — | — | OCH₃ | CH₂OCH₃ | |
| J₁₅ | — | — | — | SO₂ | — | H | — | CH₃ | H | H | — | — | — | OCH₃ | CH₂F | |
| J₁₅ | — | — | — | SO₂ | — | H | — | CH₃ | H | H | — | — | — | OCH₃ | CF₃ | |
| J₁₅ | — | — | — | SO₂ | — | H | — | CH₃ | CH₃ | H | — | — | — | OCH₃ | OCH₃ | |
| J₁₅ | — | — | — | SO₂ | — | H | — | CH₃ | H | CH₃ | — | — | — | OCH₃ | OCH₃ | |
| J₁₅ | — | — | — | SO₂ | — | H | — | CH₃ | H | CH₃ | — | — | — | OCH₃ | CH₃ | |
| J₁₅ | — | — | — | SO₂ | — | H | — | CH₃ | H | CH₃ | — | — | — | CH₃ | CH₃ | |
| J₁₅ | — | — | — | SO₂ | — | H | — | CH₃ | H | CH₃ | — | — | — | Cl | OCH₃ | |
| J₁₅ | — | — | — | SO₂ | — | H | — | CH₃ | H | CH₃ | — | — | — | Br | OCH₃ | |
| J₁₅ | — | — | — | SO₂ | — | H | — | CH₃ | H | CH₃ | — | — | — | OCH₃ | C₂H₅ | |
| J₁₅ | — | — | — | SO₂ | — | H | — | CH₃ | H | CH₃ | — | — | — | CH₃ | OC₂H₅ | |
| J₁₅ | — | — | — | SO₂ | — | H | — | CH₃ | H | CH₃ | — | — | — | OCH₃ | CH₂OCH₃ | |
| J₁₅ | — | — | — | SO₂ | — | H | — | CH₃ | H | CH₃ | — | — | — | OCH₃ | CH₂F | |
| J₁₅ | — | — | — | SO₂ | — | H | — | CH₃ | H | CH₃ | — | — | — | OCH₃ | CF₃ | |
| J₁₅ | — | — | — | SO₂ | — | H | — | H | H | H | — | — | — | CH₃ | CH₃ | |
| J₁₅ | — | — | — | SO₂ | — | H | — | H | H | H | — | — | — | CH₃ | OCH₃ | |
| J₁₅ | — | — | — | SO₂ | — | H | — | H | H | H | — | — | — | OCH₃ | OCH₃ | |
| J₁₅ | — | — | — | SO₂ | — | H | — | H | H | H | — | — | — | Cl | OCH₃ | |
| J₁₅ | — | — | — | SO₂ | — | 6-Cl | CH₃ | H | H | H | — | — | — | CH₃ | CH₃ | |
| J₁₅ | — | — | — | SO₂ | — | 6-Cl | CH₃ | H | H | H | — | — | — | CH₃ | OCH₃ | |
| J₁₅ | — | — | — | SO₂ | — | 6-Cl | CH₃ | H | H | H | — | — | — | OCH₃ | OCH₃ | |
| J₁₅ | — | — | — | SO₂ | — | 6-Cl | CH₃ | H | H | H | — | — | — | Cl | OCH₃ | |
| J₁₅ | — | — | — | S | — | H | — | CH₃ | H | CH₃ | — | — | — | OCH₃ | OCH₃ | |
| J₁₅ | — | — | — | S | — | H | — | CH₃ | H | CH₃ | — | — | — | OCH₃ | CH₃ | |
| J₁₅ | — | — | — | S | — | H | — | CH₃ | H | CH₃ | — | — | — | CH₃ | CH₃ | |
| J₁₅ | — | — | — | S | — | H | — | CH₃ | H | CH₃ | — | — | — | Cl | OCH₃ | |
| J₁₅ | — | — | — | S | — | H | — | CH₃ | H | CH₃ | — | — | — | Br | OCH₃ | |
| J₁₅ | — | — | — | O | — | 6-Cl | — | CH₃ | H | H | — | — | — | OCH₃ | OCH₃ | |
| J₁₅ | — | — | — | O | — | 5-Br | — | H | H | CH₃ | — | — | — | OCH₃ | OCH₃ | |
| J₁₅ | — | — | — | O | — | 6-F | — | CH₃ | H | H | — | — | — | OCH₃ | OCH₃ | |
| J₁₅ | — | — | — | O | — | 5-CH₃ | — | CH₃ | H | H | — | — | — | OCH₃ | OCH₃ | |
| J₁₅ | — | — | — | O | — | 6-OCH₃ | — | CH₃ | H | H | — | — | — | OCH₃ | OCH₃ | |
| J₁₅ | — | — | — | S | — | 6-Cl | — | CH₃ | H | H | — | — | — | OCH₃ | OCH₃ | |
| J₁₆ | — | CH₂ | — | O | — | H | — | CH₃ | H | — | — | — | — | OCH₃ | OCH₃ | |
| J₁₆ | — | CH₂ | — | S | — | H | — | H | CH₃ | — | — | — | — | OCH₃ | OCH₃ | |
| J₁₆ | — | O | — | SO₂ | — | H | — | CH₃ | H | — | — | — | — | OCH₃ | OCH₃ | |
| J₁₆ | — | O | — | SO₂ | — | H | — | CH₃ | H | — | — | — | — | Cl | OCH₃ | |
| J₁₇ | — | — | — | — | O | H | — | CH₃ | H | — | — | — | — | OCH₃ | OCH₃ | |
| J₁₇ | — | — | — | — | S | H | — | CH₃ | H | — | — | — | — | OCH₃ | OCH₃ | |
| J₁₇ | — | — | — | — | O | H | — | CH₃ | CH₃ | — | — | — | — | OCH₃ | OCH₃ | |
| J₁₇ | — | — | — | — | O | H | — | H | H | — | — | — | — | OCH₃ | OCH₃ | |
| J₁₈ | — | CH₂ | — | — | — | H | — | H | H | — | H | H | — | OCH₃ | OCH₃ | |
| J₁₈ | — | CH₂ | — | — | — | H | — | H | H | — | CH₃ | H | — | Cl | OCH₃ | |
| J₁₈ | — | O | — | — | — | H | — | H | H | — | H | CH₃ | — | OCH₃ | OCH₃ | |
| J₁₉ | — | — | — | — | — | H | — | CH₃ | CH₃ | — | — | — | — | OCH₃ | OCH₃ | |
| J₁₉ | — | — | — | — | — | H | — | H | H | — | — | — | — | OCH₃ | OCH₃ | |
| J₁₉ | — | — | — | — | — | H | — | H | H | — | — | — | — | Cl | OCH₃ | |
| J₁₉ | — | — | — | — | — | H | — | CH₃ | CH₃ | — | — | — | — | Cl | OCH₃ | |

TABLE 1a-continued

General Formula 1a

| J | n | L | Q | Q₁ | Q₂ | R₁ | R₂ | R₃ | R₄ | R₅ | R₆ | R₇ | R₈ | X | Y | m.p. (°C.) |
|---|---|---|---|---|---|---|---|---|---|---|---|---|---|---|---|---|
| $J_{20}$ | — | $CH_2$ | — | — | — | H | — | — | — | — | — | — | — | $OCH_3$ | $OCH_3$ | |
| $J_{20}$ | — | $CH_2$ | — | — | — | H | — | — | — | — | — | — | — | $OCH_3$ | $CH_3$ | |
| $J_{20}$ | — | $CH_2$ | — | — | — | H | — | — | — | — | — | — | — | Cl | $OCH_3$ | |
| $J_{20}$ | — | $CH_2$ | — | — | — | H | — | — | — | — | — | — | — | $CH_3$ | $CH_3$ | |
| $J_{20}$ | — | $CH_2$ | — | — | — | 7-Cl | — | — | — | — | — | — | — | $OCH_3$ | $OCH_3$ | |
| $J_{20}$ | — | O | — | — | — | H | — | — | — | — | — | — | — | $OCH_3$ | $OCH_3$ | |
| $J_{20}$ | — | O | — | — | — | H | — | — | — | — | — | — | — | $OCH_3$ | $CH_3$ | |
| $J_{20}$ | — | O | — | — | — | H | — | — | — | — | — | — | — | Cl | $OCH_3$ | |
| $J_{20}$ | — | O | — | — | — | H | — | — | — | — | — | — | — | $CH_3$ | $CH_3$ | |
| $J_{21}$ | — | $CH_2$ | — | — | — | — | — | — | — | — | — | — | F | $OCH_3$ | $OCH_3$ | |
| $J_{21}$ | — | $CH_2$ | — | — | — | — | — | — | — | — | — | — | Cl | Cl | $OCH_3$ | |
| $J_{21}$ | — | $CH_2$ | — | — | — | — | — | — | — | — | — | — | Br | $OCH_3$ | $CH_3$ | |
| $J_{21}$ | — | $CH_2$ | — | — | — | — | — | — | — | — | — | — | $OCH_3$ | $OCH_3$ | $OCH_3$ | |
| $J_{21}$ | — | $CH_2$ | — | — | — | — | — | — | — | — | — | — | $SCH_3$ | $OCH_3$ | $OCH_3$ | |
| $J_{21}$ | — | $CH_2$ | — | — | — | — | — | — | — | — | — | — | $SO_2CH_3$ | $OCH_3$ | $OCH_3$ | |
| $J_{21}$ | — | $CH_2$ | — | — | — | — | — | — | — | — | — | — | $CO_2CH_3$ | $OCH_3$ | $OCH_3$ | |
| $J_{21}$ | — | $CH_2$ | — | — | — | — | — | — | — | — | — | — | $SO_2N(CH_3)_2$ | $OCH_3$ | $OCH_3$ | |
| $J_{21}$ | — | $CH_2$ | — | — | — | — | — | — | — | — | — | — | $OSO_2CH_3$ | $OCH_3$ | $OCH_3$ | |
| $J_{21}$ | — | $CH_2$ | — | — | — | — | — | — | — | — | — | — | Cl | $OCH_3$ | $OCH_3$ | |
| $J_{21}$ | — | $CH_2$ | — | — | — | — | — | — | — | — | — | — | Cl | Br | $OCH_3$ | |
| $J_{21}$ | — | $CH_2$ | — | — | — | — | — | — | — | — | — | — | Cl | $OCH_3$ | $CH_2F$ | |
| $J_{21}$ | — | $CH_2$ | — | — | — | — | — | — | — | — | — | — | Cl | $CH_3$ | $OC_2H_5$ | |
| $J_{21}$ | — | $CH_2$ | — | — | — | — | — | — | — | — | — | — | Cl | $OCH_3$ | $C_2H_5$ | |
| $J_{21}$ | — | O | — | — | — | — | — | — | — | — | — | — | F | $OCH_3$ | $OCH_3$ | |
| $J_{21}$ | — | O | — | — | — | — | — | — | — | — | — | — | Cl | $OCH_3$ | $OCH_3$ | |
| $J_{21}$ | — | O | — | — | — | — | — | — | — | — | — | — | Br | Cl | $OCH_3$ | |
| $J_{21}$ | — | O | — | — | — | — | — | — | — | — | — | — | $OCH_3$ | $OCH_3$ | $OCH_3$ | |
| $J_{21}$ | — | O | — | — | — | — | — | — | — | — | — | — | $SCH_3$ | $OCH_3$ | $OCH_3$ | |
| $J_{21}$ | — | O | — | — | — | — | — | — | — | — | — | — | $SO_2CH_3$ | $OCH_3$ | $OCH_3$ | |
| $J_{21}$ | — | O | — | — | — | — | — | — | — | — | — | — | $CO_2CH_3$ | $OCH_3$ | $OCH_3$ | |

TABLE 1a-continued

General Formula 1a

| J | n | L | Q | Q₁ | Q₂ | R₁ | R₂ | R₃ | R₄ | R₅ | R₆ | R₇ | R₈ | X | Y | m.p. (°C.) |
|---|---|---|---|---|---|---|---|---|---|---|---|---|---|---|---|---|
| J$_8$ | — | CH$_2$ | — | — | — | H | — | — | — | — | — | — | — | OCH$_3$ | cyclopropyl | |
| J$_9$ | — | O | — | — | — | H | — | — | — | — | — | — | — | OCH$_3$ | CH(OCH$_3$)$_2$ | |
| J$_9$ | — | O | — | — | — | H | — | — | — | — | — | — | — | Cl | N(CH$_3$)$_2$ | |
| J$_9$ | — | O | — | — | — | H | — | — | — | — | — | — | — | OCH$_3$ | NHCH$_3$ | |
| J$_{10}$ | — | — | — | — | — | H | CH$_3$ | — | — | — | — | — | — | Cl | NHCH$_3$ | |
| J$_{10}$ | — | — | — | — | — | H | CH$_3$ | — | — | — | — | — | — | Cl | OCH$_3$ | |
| J$_{11}$ | — | — | — | — | — | H | CH$_3$ | — | — | — | — | — | — | Cl | OCH$_3$ | |
| J$_{11}$ | — | — | — | — | — | H | — | — | — | — | — | — | — | OCH$_3$ | NHCH$_3$ | |
| J$_{12}$ | — | O | — | — | — | H | — | — | — | — | — | — | — | Cl | NHCH$_3$ | |
| J$_{12}$ | — | O | — | — | — | H | — | — | — | — | — | — | — | OCH$_3$ | N(CH$_3$)$_2$ | |
| J$_{12}$ | — | O | — | — | — | H | — | — | — | — | — | — | — | OCH$_3$ | 1,3-dioxolan-2-yl | |
| J$_{13}$ | — | CH$_2$ | CH$_2$ | — | — | H | — | — | — | — | — | — | — | OCH$_3$ | NHCH$_3$ | |
| J$_{13}$ | — | CH$_2$ | CH$_2$ | — | — | H | — | — | — | — | — | — | — | OCH$_3$ | SCH$_3$ | |
| J$_{13}$ | — | CH$_2$ | CH$_2$ | — | — | H | — | — | — | — | — | — | — | OCH$_3$ | CH(OCH$_3$)$_2$ | |
| J$_{13}$ | — | CH$_2$ | CH$_2$ | — | — | H | — | — | — | — | — | — | — | OCH$_3$ | OCH$_2$CH≡CH | |
| J$_{14}$ | — | CH$_2$ | — | — | — | H | — | — | — | — | — | — | — | OCH$_3$ | OCH$_2$CH=CH$_2$ | |
| J$_{14}$ | — | CH$_2$ | — | — | — | H | — | — | — | — | — | — | — | CH$_3$ | OCH$_2$CH$_2$F | |
| J$_{14}$ | — | CH$_2$ | — | — | — | H | — | — | — | — | — | — | — | OCH$_2$CF$_3$ | OCH$_3$ | |
| J$_{14}$ | — | CH$_2$ | — | — | — | H | — | — | — | — | — | — | — | OCHF$_2$ | OCHF$_2$ | |
| J$_{14}$ | — | CH$_2$ | — | — | — | H | — | — | — | — | — | — | — | OCH$_3$ | OCH$_2$CH$_2$OCH$_3$ | |
| J$_{15}$ | — | — | — | O | — | H | — | CH$_3$ | H | H | — | — | — | OCH$_3$ | NHCH$_3$ | |
| J$_{15}$ | — | — | — | O | — | H | — | CH$_3$ | H | H | — | — | — | OCH$_3$ | OCH$_2$CH=CH$_2$ | |
| J$_{15}$ | — | — | — | O | — | H | — | H | H | H | — | — | — | OCH$_3$ | C≡CH | |
| J$_{15}$ | — | — | — | O | — | H | — | H | H | H | — | — | — | OCH$_3$ | OCH$_2$CH$_2$F | |
| J$_{15}$ | — | — | — | O | — | H | — | CH$_3$ | H | H | — | — | — | OCH$_3$ | OCH$_2$CH=CHCl | |
| J$_{15}$ | — | — | — | O | — | H | — | H | H | H | — | — | — | Cl | NHCH$_3$ | |
| J$_{15}$ | — | — | — | O | — | H | — | H | H | CH$_3$ | — | — | — | Cl | N(CH$_3$)$_2$ | |
| J$_{15}$ | — | — | — | O | — | H | — | H | H | CH$_3$ | — | — | — | OCH$_3$ | cyclopropyl | |
| J$_{15}$ | — | — | — | O | — | H | — | H | H | CH$_3$ | — | — | — | OCH$_3$ | CH(OCH$_3$)$_2$ | |
| J$_{15}$ | — | — | — | O | — | H | — | CH$_3$ | CH$_3$ | H | — | — | — | OCH$_3$ | NHCH$_3$ | |
| J$_{15}$ | — | — | — | O | — | H | — | CH$_3$ | CH$_3$ | H | — | — | — | OCH$_3$ | CH(OCH$_3$)$_2$ | |
| J$_{15}$ | — | — | — | O | — | H | — | CH$_3$ | H | H | — | — | — | OCH$_3$ | OCH$_2$C≡CH | |
| J$_{15}$ | — | — | — | O | — | H | — | CH$_3$ | CH$_3$ | H | — | — | — | OCH$_3$ | SCH$_3$ | |
| J$_{15}$ | — | — | — | S | — | H | — | CH$_3$ | H | H | — | — | — | OCH$_3$ | NHCH$_3$ | |
| J$_{15}$ | — | — | — | S | — | H | — | CH$_3$ | H | H | — | — | — | OCH$_3$ | N(CH$_3$)$_2$ | |
| J$_{15}$ | — | — | — | S | — | H | — | CH$_3$ | H | H | — | — | — | OCH$_3$ | OCH$_2$CH=CH$_2$ | |
| J$_{15}$ | — | — | — | S | — | H | — | CH$_3$ | H | H | — | — | — | OCH$_3$ | cyclopropyl | |
| J$_{15}$ | — | — | — | S | — | H | — | CH$_3$ | H | H | — | — | — | Cl | N(CH$_3$)$_2$ | |
| J$_{15}$ | — | — | — | S | — | H | — | CH$_3$ | CH$_3$ | CH$_3$ | — | — | — | OCH$_3$ | CH(OCH$_3$)$_2$ | |
| J$_{15}$ | — | — | — | SO$_2$ | — | H | — | CH$_3$ | H | H | — | — | — | OCH$_3$ | NHCH$_3$ | |
| J$_{15}$ | — | — | — | SO$_2$ | — | H | — | CH$_3$ | H | H | — | — | — | Cl | N(CH$_3$)$_2$ | |
| J$_{15}$ | — | — | — | SO$_2$ | — | H | — | CH$_3$ | H | H | — | — | — | OCH$_3$ | OCH$_2$CH=CH$_2$ | |
| J$_{15}$ | — | — | — | SO$_2$ | — | H | — | CH$_3$ | H | H | — | — | — | OCHF$_2$ | SCH$_3$ | |
| J$_{15}$ | — | — | — | SO$_2$ | — | H | — | CH$_3$ | H | H | — | — | — | CH$_3$ | OCH$_2$CH$_2$OCH$_3$ | |
| J$_{15}$ | — | — | — | SO$_2$ | — | H | — | CH$_3$ | H | H | — | — | — | CH$_3$ | CH(OCH$_3$)$_2$ | |
| J$_{16}$ | — | CH$_2$ | — | O | — | H | — | CH$_3$ | H | — | — | — | — | OCH$_3$ | N(CH$_3$)$_2$ | |
| J$_{16}$ | — | CH$_2$ | — | S | — | H | — | H | CH$_3$ | — | — | — | — | OCH$_3$ | OCH$_2$CH=CH$_2$ | |
| J$_{16}$ | — | O | — | SO$_2$ | — | H | — | CH$_3$ | H | — | — | — | — | OCH$_3$ | OCH$_2$CH$_2$F | |
| J$_{16}$ | — | O | — | SO$_2$ | — | H | — | CH$_3$ | H | — | — | — | — | OCH$_3$ | OCH$_2$CH$_2$OCH$_3$ | |
| J$_{17}$ | — | — | — | — | O | H | — | CH$_3$ | H | — | — | — | — | Cl | N(CH$_3$)$_2$ | |
| J$_{17}$ | — | — | — | — | O | H | — | CH$_3$ | H | — | — | — | — | CH$_3$ | CH(OCH$_3$)$_2$ | |
| J$_{17}$ | — | — | — | — | S | H | — | CH$_3$ | H | — | — | — | — | OCH$_3$ | NHCH$_3$ | |
| J$_{18}$ | — | CH$_2$ | — | — | — | H | — | H | H | — | H | H | — | OCH$_3$ | NHCH$_3$ | |
| J$_{18}$ | — | CH$_2$ | — | — | — | H | — | H | H | — | CH$_3$ | H | — | Cl | N(CH$_3$)$_2$ | |
| J$_{18}$ | — | O | — | — | — | H | — | H | H | — | H | CH$_3$ | — | CH$_3$ | OCH$_2$CH$_2$OCH$_3$ | |
| J$_{19}$ | — | — | — | — | — | H | — | H | H | — | — | — | — | CH$_3$ | OCH$_2$CH$_2$F | |
| J$_{19}$ | — | — | — | — | — | H | — | CH$_3$ | CH$_3$ | — | — | — | — | OCH$_3$ | NHCH$_3$ | |
| J$_{19}$ | — | — | — | — | — | H | — | H | CH$_3$ | — | — | — | — | OCH$_3$ | C≡CH | |
| J$_{20}$ | — | CH$_2$ | — | — | — | H | — | — | — | — | — | — | — | OCH$_3$ | NHCH$_3$ | |
| J$_{20}$ | — | CH$_2$ | — | — | — | H | — | — | — | — | — | — | — | CH$_3$ | OCH$_2$CH$_2$F | |
| J$_{20}$ | — | O | — | — | — | H | — | — | — | — | — | — | — | OCH$_3$ | C≡CH | |
| J$_{20}$ | — | O | — | — | — | H | — | — | — | — | — | — | — | OCH$_3$ | CH(OCH$_3$)$_2$ | |
| J$_{21}$ | — | CH$_2$ | — | — | — | — | — | — | — | — | — | — | Cl | OCH$_3$ | NHCH$_3$ | |
| J$_{21}$ | — | CH$_2$ | — | — | — | — | — | — | — | — | — | — | Br | OCH$_3$ | N(CH$_3$)$_2$ | |
| J$_{21}$ | — | CH$_2$ | — | — | — | — | — | — | — | — | — | — | F | OCH$_3$ | NHCH$_3$ | |
| J$_{21}$ | — | CH$_2$ | — | — | — | — | — | — | — | — | — | — | OCH$_3$ | OCH$_3$ | NHCH$_3$ | |
| J$_{21}$ | — | CH$_2$ | — | — | — | — | — | — | — | — | — | — | SO$_2$N(CH$_3$)$_2$ | OCH$_3$ | C≡CH | |
| J$_{21}$ | — | CH$_2$ | — | — | — | — | — | — | — | — | — | — | Cl | OCH$_3$ | OCH$_2$CH$_2$F | |
| J$_{21}$ | — | O | — | — | — | — | — | — | — | — | — | — | Cl | Cl | NHCH$_3$ | |
| J$_{21}$ | — | O | — | — | — | — | — | — | — | — | — | — | Br | OCH$_3$ | NHCH$_3$ | |
| J$_{21}$ | — | O | — | — | — | — | — | — | — | — | — | — | OCH$_3$ | OCH$_3$ | NHCH$_3$ | |
| J$_{21}$ | — | O | — | — | — | — | — | — | — | — | — | — | SO$_2$N(CH$_3$)$_2$ | OCH$_3$ | NHCH$_3$ | |
| J$_{21}$ | — | O | — | — | — | — | — | — | — | — | — | — | SO$_2$CH$_3$ | OCH$_3$ | NHCH$_3$ | |
| J$_{21}$ | — | CH$_2$ | — | — | — | — | — | — | — | — | — | — | CO$_2$CH$_3$ | OCH$_3$ | OCH$_3$ | 148–151.5 |
| J$_{21}$ | — | CH$_2$ | — | — | — | — | — | — | — | — | — | — | CO$_2$CH$_3$ | CH$_3$ | CH$_3$ | 191–193.5 |

TABLE 1a-continued

General Formula 1a

| J | n | L | Q | Q₁ | Q₂ | R₁ | R₂ | R₃ | R₄ | R₅ | R₆ | R₇ | R₈ | X | Y | m.p. (°C.) |
|---|---|---|---|----|----|----|----|----|----|----|----|----|----|---|---|------------|
| $J_{21}$ | — | $CH_2$ | — | — | — | — | — | — | — | — | — | — | $CO_2CH_3$ | $OCH_3$ | $CH_3$ | |

TABLE 2

General Formula 2

| J | n | L | R₁ | R₉ | X | Y | m.p. (°C.) |
|---|---|---|----|----|---|---|------------|
| $J_1$ | 0 | $CH_2$ | H | $CH_3$ | $CH_3$ | $OCH_3$ | |
| $J_1$ | 0 | $CH_2$ | H | $CH_3$ | $OCH_3$ | $OCH_3$ | |
| $J_1$ | 0 | $CH_2$ | H | $CH_3$ | $CH_3$ | $CH_3$ | |
| $J_1$ | 0 | $CH_2$ | H | $CH_3$ | $OCH_3$ | $C_2H_5$ | |
| $J_1$ | 0 | $CH_2$ | H | $CH_3$ | $CH_3$ | $OC_2H_5$ | |
| $J_1$ | 0 | $CH_2$ | H | $CH_3$ | $OCH_3$ | $CH_2OCH_3$ | |
| $J_1$ | 0 | $CH_2$ | H | $CH_3$ | $OCH_3$ | $CH_2F$ | |
| $J_1$ | 0 | $CH_2$ | H | $CH_3$ | $OCH_3$ | $CF_3$ | |
| $J_1$ | 1 | $CH_2$ | H | $CH_3$ | $OCH_3$ | $CH_3$ | |
| $J_1$ | 0 | $CH_2$ | H | $C_2H_5$ | $OCH_3$ | $CH_3$ | |
| $J_1$ | 0 | $CH_2$ | H | n-$C_3H_7$ | $OCH_3$ | $CH_3$ | |
| $J_1$ | 0 | $CH_2$ | H | $CH(CH_3)_2$ | $OCH_3$ | $CH_3$ | |
| $J_1$ | 0 | $CH_2$ | H | H | $OCH_3$ | $OCH_3$ | |
| $J_1$ | 0 | $CH_2$ | H | H | $OCH_3$ | $CH_3$ | |
| $J_1$ | 0 | $CH_2$ | H | H | $CH_3$ | $CH_3$ | |
| $J_1$ | 0 | O | H | H | $CH_3$ | $CH_3$ | |
| $J_1$ | 0 | O | H | H | $CH_3$ | $OCH_3$ | |
| $J_1$ | 0 | O | H | H | $OCH_3$ | $OCH_3$ | |
| $J_1$ | 0 | O | H | $CH_3$ | $OCH_3$ | $OCH_3$ | |
| $J_1$ | 0 | O | H | $CH_3$ | $CH_3$ | $OCH_3$ | |
| $J_1$ | 0 | O | H | $CH_3$ | $CH_3$ | $CH_3$ | |
| $J_1$ | 0 | O | H | $C_2H_5$ | $OCH_3$ | $OCH_3$ | |
| $J_1$ | 0 | O | H | n-$C_3H_7$ | $OCH_3$ | $CH_3$ | |
| $J_1$ | 0 | O | H | $CH(CH_3)_2$ | $OCH_3$ | $OCH_3$ | |
| $J_1$ | 1 | O | H | $CH_3$ | $OCH_3$ | $CH_3$ | |
| $J_1$ | 0 | $CH_2$ | 5-F | $CH_3$ | $OCH_3$ | $CH_3$ | |
| $J_1$ | 0 | $CH_2$ | 6-Cl | $CH_3$ | $OCH_3$ | $CH_3$ | |
| $J_1$ | 0 | $CH_2$ | 6-Br | $CH_3$ | $OCH_3$ | $OCH_3$ | |
| $J_1$ | 0 | $CH_2$ | 6-$CH_3$ | $CH_3$ | $OCH_3$ | $OCH_3$ | |
| $J_1$ | 0 | $CH_2$ | 6-$OCH_3$ | $CH_3$ | $OCH_3$ | $OCH_3$ | |
| $J_1$ | 0 | O | H | $CH_3$ | $OCH_2CF_3$ | $CH_3$ | |
| $J_1$ | 0 | O | H | $CH_3$ | $OCH_3$ | $CH(CH_3)$ | |
| $J_1$ | 0 | O | H | $CH_3$ | $OCH_3$ | cyclopropyl | |
| $J_1$ | 0 | O | H | $CH_3$ | $OCH_3$ | $C{\equiv}CH$ | |
| $J_1$ | 0 | O | H | $CH_3$ | $OCH_3$ | $NH_2$ | |
| $J_1$ | 0 | O | H | $CH_3$ | $OCH_3$ | $N(CH_3)_2$ | |
| $J_1$ | 0 | O | H | $CH_3$ | $OCH_3$ | $OCH_2CH_2F$ | |
| $J_1$ | 0 | O | H | $CH_3$ | $OCH_3$ | $SCH_3$ | |
| $J_1$ | 0 | O | H | $CH_3$ | $OCH_3$ | $OCH_2CH{=}CH_2$ | |
| $J_1$ | 0 | O | H | $CH_3$ | $OCH_3$ | $OCH_2CH_2OCH_3$ | |
| $J_1$ | 0 | O | H | $CH_3$ | $OCH_3$ | $OCH_2C{\equiv}CH$ | |
| $J_1$ | 0 | O | H | $CH_3$ | $OCH_3$ | $CH(OCH_3)_2$ | |
| $J_1$ | 0 | O | H | $CH_3$ | $OCH_3$ | $C(CH_3)(OCH_3)_2$ | |
| $J_1$ | 0 | O | H | $CH_3$ | $OCH_3$ | 1,3-dioxolan-2-yl | |
| $J_1$ | 0 | O | H | $CH_3$ | $OCH_3$ | 2-methyl-1,3-dioxolan-2-yl | |
| $J_1$ | 0 | O | H | $CH_3$ | $OCH_3$ | $CH(OC_2H_5)_2$ | |
| $J_1$ | 0 | O | H | $CH_3$ | $OCH_3$ | $C(CH_3)(OC_2H_5)_2$ | |
| $J_1$ | 0 | O | H | $CH_3$ | $OCH_3$ | $NHCH_3$ | |
| $J_1$ | 0 | O | H | $-CH_2CN$ | $OCH_3$ | $OCH_3$ | |
| $J_1$ | 0 | O | H | $-(CH_2)_3CN$ | $CH_3$ | $OCH_3$ | |
| $J_1$ | 0 | $CH_2$ | H | OH | $CH_3$ | $OCH_3$ | |
| $J_1$ | 0 | $CH_2$ | H | $-(CH_2)_3CH(CH_3)_2$ | Cl | $OCH_3$ | |
| $J_1$ | 0 | $CH_2$ | H | $-CF_2H$ | $OCH_3$ | $OCH_3$ | |
| $J_1$ | 0 | $CH_2$ | H | $-CH_2CH_2Cl$ | Cl | $OCH_3$ | |
| $J_1$ | 0 | $CH_2$ | H | $-(CH_2)_5Cl$ | $CH_3$ | $OCH_3$ | |
| $J_1$ | 0 | $CH_2$ | H | $-CH_2OCH_3$ | Cl | $OCH_3$ | |
| $J_1$ | 0 | $CH_2$ | H | $-(CH_2)_4OCH_3$ | $CH_3$ | $OCH_3$ | |
| $J_1$ | 0 | $CH_2$ | H | $-CH_2CH{=}CH_2$ | $OCH_3$ | $OCH_3$ | |
| $J_1$ | 0 | $CH_2$ | H | $-CH_2CH{=}CHCH_3$ | $CH_3$ | $OCH_3$ | |
| $J_1$ | 0 | $CH_2$ | H | $-CH_2C{\equiv}CH$ | $OCH_3$ | $OCH_3$ | |
| $J_1$ | 0 | $CH_2$ | H | $-(CH_2)_4C{\equiv}CH$ | $CH_3$ | $OCH_3$ | |
| $J_1$ | 0 | $CH_2$ | H | $-OCH_3$ | $CH_3$ | $OCH_3$ | |
| $J_1$ | 0 | $CH_2$ | H | $-C_6H_5$ | $CH_3$ | $OCH_3$ | |
| $J_1$ | 0 | $CH_2$ | H | cyclopropyl | $OCH_3$ | $OCH_3$ | |
| $J_1$ | 0 | $CH_2$ | H | cyclohexyl | $OCH_3$ | $OCH_3$ | |
| $J_1$ | 0 | $CH_2$ | H | cyclopropylmethyl | $OCH_3$ | $OCH_3$ | |
| $J_1$ | 0 | $CH_2$ | H | cyclohexylmethyl | $CH_3$ | $OCH_3$ | |
| $J_1$ | 0 | $CH_2$ | H | $-C(O)CH_3$ | $OCH_3$ | $OCH_3$ | |

TABLE 2-continued

General Formula 2

| J | n | L | R₁ | R₉ | X | Y | m.p. (°C.) |
|---|---|---|---|---|---|---|---|
| J₁ | 0 | CH₂ | H | —C(O)(CH₂)₅H | OCH₃ | OCH₃ | |
| J₁ | 0 | CH₂ | H | —CO₂C₂H₅ | CH₃ | OCH₃ | |
| J₁ | 0 | CH₂ | H | —CO₂(CH₂)₄H | CH₃ | OCH₃ | |
| J₁ | 0 | CH₂ | H | —CH₂C₆H₅ | OCH₃ | OCH₃ | |
| J₁ | 0 | CH₂ | H | —CH₂—CH=CH—CH₂Cl | CH₃ | OCH₃ | |
| J₁ | 0 | CH₂ | H | —CH₂C≡C—CH₂Cl | CH₃ | OCH₃ | |
| J₁ | 0 | CH₂ | H | —CH₂C(O)CH₃ | OCH₃ | OCH₃ | |
| J₁ | 0 | CH₂ | H | —CH(CH₃)CO₂C₂H₅ | OCH₃ | OCH₃ | |
| J₁ | 0 | CH₂ | H | H | OCH₃ | OCH₃ | |
| J₁ | 0 | CH₂ | H | H | CH₃ | CH₃ | |
| J₁ | 0 | O | H | H | CH₃ | CH₃ | |
| J₁ | 0 | O | H | H | OCH₃ | CH₃ | |
| J₁ | 0 | O | H | H | OCH₃ | OCH₃ | |
| J₁ | 0 | CH₂ | H | n-C₄H₉ | CH₃ | CH₃ | |
| J₁ | 0 | CH₂ | H | n-C₄H₉ | CH₃ | OCH₃ | |
| J₁ | 0 | CH₂ | H | n-C₄H₉ | OCH₃ | OCH₃ | |
| J₁ | 0 | O | H | n-C₄H₉ | CH₃ | CH₃ | |
| J₁ | 0 | O | H | n-C₄H₉ | OCH₃ | CH₃ | |
| J₁ | 0 | O | H | n-C₄H₉ | OCH₃ | OCH₃ | |
| J₇ | — | CH₂ | H | n-C₃H₇ | CH₃ | OCH₃ | |
| J₇ | — | CH₂ | H | CH(CH₃)₂ | CH₃ | OCH₃ | |
| J₇ | — | O | H | CH₃ | CH₃ | OCH₃ | |
| J₇ | — | CH₂ | 7-Cl | CH₃ | CH₃ | OCH₃ | |
| J₇ | — | O | 7-Br | CH₃ | CH₃ | OCH₃ | |
| J₇ | — | CH₂ | 6-F | CH₃ | CH₃ | OCH₃ | |
| J₇ | — | O | 7-CH₃ | CH₃ | CH₃ | OCH₃ | |
| J₇ | — | O | 7-OCH₃ | CH₃ | CH₃ | OCH₃ | |
| J₇ | — | CH₂ | H | CH₃ | OCH₃ | OCH₃ | |
| J₇ | — | CH₂ | H | CH₃ | CH₃ | CH₃ | |
| J₇ | — | CH₂ | H | CH₃ | OCH₃ | C₂H₅ | |
| J₇ | — | CH₂ | H | CH₃ | CH₃ | OC₂H₅ | |
| J₇ | — | CH₂ | H | CH₃ | OCH₃ | CH₂OCH₃ | |
| J₇ | — | CH₂ | H | CH₃ | OCH₃ | CH₂F | |
| J₇ | — | CH₂ | H | CH₃ | OCH₃ | CF₃ | |
| J₇ | — | CH₂ | H | H | CH₃ | OCH₃ | |
| J₇ | — | CH₂ | H | C₂H₅ | CH₃ | OCH₃ | |
| J₇ | — | CH₂ | H | CH₃ | OCH₂CF₃ | OCH₃ | |
| J₇ | — | CH₂ | H | CH₃ | OCH₃ | cyclopropyl | |
| J₇ | — | CH₂ | H | CH₃ | OCH₃ | NHCH₃ | |
| J₇ | — | CH₂ | H | CH₃ | OCH₃ | N(CH₃)₂ | |
| J₇ | — | CH₂ | H | CH₃ | OCH₃ | OCH₂CH=CH₂ | |
| J₇ | — | CH₂ | H | CH₃ | OCH₃ | CH(OCH₃)₂ | |
| J₇ | — | CH₂ | H | CH₃ | OCH₃ | 1,3-dioxolan-2-yl | |
| J₇ | — | CH₂ | H | CH₃ | OCH₃ | CH(OC₂H₅)₂ | |
| J₇ | — | CH₂ | H | CH₃ | OCH₃ | —C≡CH | |
| J₇ | — | CH₂ | H | CH₃ | OCH₃ | C(CH₃)(OCH₃)₂ | |
| J₇ | — | CH₂ | H | OH | OCH₃ | OCH₃ | |
| J₇ | — | CH₂ | H | (CH₂)₂CH(CH₃)₂ | CH₃ | OCH₃ | |
| J₇ | — | CH₂ | H | CH₂CH₂Cl | OCH₃ | OCH₃ | |
| J₇ | — | CH₂ | H | (CH₂)₅Cl | CH₃ | OCH₃ | |
| J₇ | — | CH₂ | H | CH₂OCH₃ | OCH₃ | OCH₃ | |
| J₇ | — | CH₂ | H | (CH₂)₂OCH₃ | OCH₃ | OCH₃ | |
| J₇ | — | CH₂ | H | CH₂CH=CH₂ | OCH₃ | OCH₃ | |
| J₇ | — | CH₂ | H | CH₂CH=CHCH₂Cl | CH₃ | OCH₃ | |
| J₇ | — | CH₂ | H | CH₂CH=CHCH₃ | CH₃ | OCH₃ | |
| J₇ | — | CH₂ | H | CH₂C≡CCH₃ | OCH₃ | OCH₃ | |
| J₇ | — | CH₂ | H | OCH₃ | OCH₃ | OCH₃ | |
| J₇ | — | CH₂ | H | O(CH₂)₄CH₃ | CH₃ | OCH₃ | |
| J₇ | — | CH₂ | H | C₆H₅ | OCH₃ | OCH₃ | |
| J₇ | — | CH₂ | H | cyclopropyl | CH₃ | OCH₃ | |
| J₇ | — | CH₂ | H | cyclopentyl | OCH₃ | OCH₃ | |
| J₇ | — | CH₂ | H | COCH₃ | OCH₃ | OCH₃ | |
| J₇ | — | CH₂ | H | CO₂CH₃ | OCH₃ | OCH₃ | |
| J₇ | — | CH₂ | H | CH₂C₆H₅ | CH₃ | OCH₃ | |
| J₇ | — | CH₂ | H | CH₂CH=CHCl | CH₃ | OCH₃ | |
| J₇ | — | CH₂ | H | CH(CH₃)CO₂CH₃ | CH₃ | OCH₃ | |

TABLE 2a

General Formula 2a

| J | n | L | Q | Q₁ | Q₂ | R₁ | R₂ | R₃ | R₄ | R₅ | R₆ | R₇ | R₈ | X | Y | m.p. (°C.) |
|---|---|---|---|---|---|---|---|---|---|---|---|---|---|---|---|---|
| J₂ | 0 | CH₂ | — | — | — | H | — | H | CH₃ | — | — | — | — | OCH₃ | OCH₃ | |
| J₂ | 0 | CH₂ | — | — | — | H | CH₃ | — | — | — | — | — | — | OCH₃ | CH₃ | |
| J₂ | 0 | CH₂ | — | — | — | H | CH₃ | — | — | — | — | — | — | OCH₃ | C₂H₅ | |

TABLE 2a-continued

General Formula 2a

| J | n | L | Q | Q₁ | Q₂ | R₁ | R₂ | R₃ | R₄ | R₅ | R₆ | R₇ | R₈ | X | Y | m.p. (°C.) |
|---|---|---|---|---|---|---|---|---|---|---|---|---|---|---|---|---|
| J₂ | 0 | CH₂ | — | — | — | H | CH₃ | — | — | — | — | — | — | CH₃ | OC₂H₅ | |
| J₂ | 0 | CH₂ | — | — | — | H | CH₃ | — | — | — | — | — | — | OCH₃ | CH₂OCH₃ | |
| J₂ | 0 | CH₂ | — | — | — | H | CH₃ | — | — | — | — | — | — | OCH₃ | CH₂F | |
| J₂ | 0 | CH₂ | — | — | — | H | CH₃ | — | — | — | — | — | — | OCH₃ | CF₃ | |
| J₂ | 0 | CH₂ | — | — | — | H | H | — | — | — | — | — | — | CH₃ | OCH₃ | |
| J₂ | 0 | CH₂ | — | — | — | H | C₂H₅ | — | — | — | — | — | — | CH₃ | OCH₃ | |
| J₂ | 0 | CH₂ | — | — | — | H | n-C₃H₇ | — | — | — | — | — | — | CH₃ | OCH₃ | |
| J₂ | 0 | CH₂ | — | — | — | H | CH(CH₃)₂ | — | — | — | — | — | — | CH₃ | OCH₃ | |
| J₂ | 1 | CH₂ | — | — | — | H | CH₃ | — | — | — | — | — | — | CH₃ | OCH₃ | |
| J₂ | 0 | O | — | — | — | H | CH₃ | — | — | — | — | — | — | OCH₃ | OCH₃ | |
| J₂ | 0 | O | — | — | — | H | CH₃ | — | — | — | — | — | — | OCH₃ | CH₃ | |
| J₂ | 1 | O | — | — | — | H | CH₃ | — | — | — | — | — | — | CH₃ | OCH₃ | |
| J₂ | 0 | O | — | — | — | H | C₂H₅ | — | — | — | — | — | — | CH₃ | OCH₃ | |
| J₂ | 0 | CH₂ | — | — | — | 6-Br | CH₃ | — | — | — | — | — | — | CH₃ | OCH₃ | |
| J₂ | 0 | CH₂ | — | — | — | 6-Cl | CH₃ | — | — | — | — | — | — | CH₃ | OCH₃ | |
| J₂ | 0 | CH₂ | — | — | — | 5-F | CH₃ | — | — | — | — | — | — | CH₃ | OCH₃ | |
| J₂ | 0 | O | — | — | — | 6-CH₃ | CH₃ | — | — | — | — | — | — | CH₃ | OCH₃ | |
| J₂ | 0 | O | — | — | — | 6-OCH₃ | CH₃ | — | — | — | — | — | — | CH₃ | OCH₃ | |
| J₃ | 0 | CH₂ | — | — | — | H | — | H | H | — | — | — | — | OCH₃ | OCH₃ | |
| J₃ | 0 | CH₂ | — | — | — | H | — | H | H | — | — | — | — | CH₃ | OCH₃ | 175–183,d |
| J₃ | 0 | CH₂ | — | — | — | H | — | H | H | — | — | — | — | CH₃ | CH₃ | |
| J₃ | 0 | CH₂ | — | — | — | H | — | H | H | — | — | — | — | OCH₃ | C₂H₅ | |
| J₃ | 0 | CH₂ | — | — | — | H | — | H | H | — | — | — | — | CH₃ | OC₂H₅ | |
| J₃ | 0 | CH₂ | — | — | — | H | — | H | H | — | — | — | — | CH₃ | CH₂OCH₃ | |
| J₃ | 0 | CH₂ | — | — | — | H | — | H | H | — | — | — | — | OCH₃ | CH₂F | |
| J₃ | 0 | CH₂ | — | — | — | H | — | H | H | — | — | — | — | OCH₃ | CF₃ | |
| J₃ | 1 | CH₂ | — | — | — | H | — | H | H | — | — | — | — | CH₃ | OCH₃ | |
| J₃ | 0 | CH₂ | — | — | — | H | — | CH₃ | H | — | — | — | — | CH₃ | OCH₃ | |
| J₃ | 0 | CH₂ | — | — | — | H | — | H | CH₃ | — | — | — | — | CH₃ | OCH₃ | |
| J₃ | 0 | O | — | — | — | H | — | H | H | — | — | — | — | OCH₃ | OCH₃ | |
| J₃ | 0 | O | — | — | — | H | — | H | H | — | — | — | — | OCH₃ | CH₃ | |
| J₃ | 0 | O | — | — | — | H | — | H | H | — | — | — | — | CH₃ | CH₃ | |
| J₃ | 0 | CH₂ | — | — | — | 5-F | — | H | H | — | — | — | — | CH₃ | OCH₃ | |
| J₃ | 0 | CH₂ | — | — | — | 6-Cl | — | H | H | — | — | — | — | OCH₃ | OCH₃ | |
| J₃ | 0 | CH₂ | — | — | — | 6-Br | — | H | H | — | — | — | — | OCH₃ | CH₃ | |
| J₃ | 0 | O | — | — | — | 5-CH₃ | — | H | H | — | — | — | — | OCH₃ | CH₃ | |
| J₃ | 0 | O | — | — | — | 6-OCH₃ | — | H | H | — | — | — | — | OCH₃ | CH₃ | |
| J₃ | 1 | O | — | — | — | H | — | H | H | — | — | — | — | OCH₃ | CH₃ | |
| J₃ | 1 | CH₂ | — | — | — | H | — | CH₃ | H | — | — | — | — | CH₃ | CH₃ | |
| J₃ | 1 | CH₂ | — | — | — | H | — | CH₃ | H | — | — | — | — | CH₃ | OCH₃ | |
| J₃ | 1 | CH₂ | — | — | — | H | — | CH₃ | H | — | — | — | — | OCH₃ | OCH₃ | |
| J₃ | 1 | O | — | — | — | H | — | CH₃ | H | — | — | — | — | CH₃ | CH₃ | |
| J₃ | 1 | O | — | — | — | H | — | CH₃ | H | — | — | — | — | CH₃ | OCH₃ | |
| J₃ | 1 | O | — | — | — | H | — | CH₃ | H | — | — | — | — | OCH₃ | OCH₃ | |
| J₄ | 0 | CH₂ | — | — | — | H | — | — | — | — | — | — | — | CH₃ | OCH₃ | |
| J₄ | 1 | CH₂ | — | — | — | H | — | — | — | — | — | — | — | CH₃ | CH₃ | |
| J₄ | 0 | O | — | — | — | H | — | — | — | — | — | — | — | CH₃ | OCH₃ | |
| J₄ | 1 | O | — | — | — | H | — | — | — | — | — | — | — | CH₃ | OCH₃ | |
| J₅ | 0 | — | — | — | — | H | CH₃ | — | — | — | — | — | — | OCH₃ | OCH₃ | |
| J₅ | 0 | — | — | — | — | H | CH₃ | — | — | — | — | — | — | CH₃ | OCH₃ | |
| J₅ | 0 | — | — | — | — | H | CH₃ | — | — | — | — | — | — | CH₃ | CH₃ | |
| J₅ | 1 | — | — | — | — | H | CH₃ | — | — | — | — | — | — | CH₃ | OCH₃ | |
| J₅ | 0 | — | — | — | — | H | H | — | — | — | — | — | — | CH₃ | OCH₃ | |
| J₆ | 0 | — | — | — | — | H | CH₃ | — | — | — | — | — | — | OCH₃ | OCH₃ | |
| J₆ | 0 | — | — | — | — | H | CH₃ | — | — | — | — | — | — | CH₃ | OCH₃ | |
| J₆ | 0 | — | — | — | — | H | H | — | — | — | — | — | — | CH₃ | OCH₃ | |
| J₆ | 1 | — | — | — | — | H | CH₃ | — | — | — | — | — | — | CH₃ | OCH₃ | |
| J₈ | — | CH₂ | — | — | — | H | — | H | — | — | — | — | — | OCH₃ | OCH₃ | |
| J₈ | — | CH₂ | — | — | — | H | — | H | — | — | — | — | — | OCH₃ | CH₃ | |
| J₈ | — | CH₂ | — | — | — | H | — | CH₃ | — | — | — | — | — | OCH₃ | CH₃ | |
| J₈ | — | CH₂ | — | — | — | H | — | H | — | — | — | — | — | OCH₃ | C₂H₅ | |
| J₈ | — | CH₂ | — | — | — | H | — | H | — | — | — | — | — | CH₃ | OC₂H₅ | |
| J₈ | — | CH₂ | — | — | — | H | — | H | — | — | — | — | — | OCH₃ | CH₂OCH₃ | |
| J₈ | — | CH₂ | — | — | — | H | — | H | — | — | — | — | — | OCH₃ | CH₂F | |
| J₈ | — | CH₂ | — | — | — | H | — | H | — | — | — | — | — | OCH₃ | CF₃ | |
| J₈ | — | O | — | — | — | H | — | H | — | — | — | — | — | OCH₃ | OCH₃ | |
| J₈ | — | O | — | — | — | H | — | H | — | — | — | — | — | OCH₃ | CH₃ | |
| J₈ | — | CH₂ | — | — | — | 7-Cl | — | H | — | — | — | — | — | CH₃ | OCH₃ | |
| J₉ | — | CH₂ | — | — | — | H | — | — | — | — | — | — | — | OCH₃ | OCH₃ | |
| J₉ | — | CH₂ | — | — | — | H | — | — | — | — | — | — | — | OCH₃ | CH₃ | |
| J₉ | — | O | — | — | — | H | — | — | — | — | — | — | — | CH₃ | OCH₃ | |
| J₁₀ | — | — | — | — | — | H | CH₃ | — | — | — | — | — | — | OCH₃ | OCH₃ | |
| J₁₀ | — | — | — | — | — | H | H | — | — | — | — | — | — | OCH₃ | CH₃ | |
| J₁₀ | — | — | — | — | — | H | C₂H₅ | — | — | — | — | — | — | CH₃ | OCH₃ | |
| J₁₁ | — | — | — | — | — | H | CH₃ | — | — | — | — | — | — | CH₃ | OCH₃ | |

TABLE 2a-continued

General Formula 2a

| J | n | L | Q | Q₁ | Q₂ | R₁ | R₂ | R₃ | R₄ | R₅ | R₆ | R₇ | R₈ | X | Y | m.p. (°C.) |
|---|---|---|---|----|----|----|----|----|----|----|----|----|----|----|----|------|
| J₁₁ | — | — | — | — | — | H | C₂H₅ | — | — | — | — | — | — | CH₃ | OCH₃ | |
| J₁₂ | — | CH₂ | — | — | — | H | — | H | — | — | — | — | — | OCH₃ | OCH₃ | |
| J₁₂ | — | CH₂ | — | — | — | H | — | H | — | — | — | — | — | OCH₃ | CH₃ | |
| J₁₂ | — | CH₂ | — | — | — | H | — | CH₂ | — | — | — | — | — | OCH₃ | OCH₃ | |
| J₁₂ | — | O | — | — | — | H | — | H | — | — | — | — | — | OCH₃ | OCH₃ | |
| J₁₂ | — | O | — | — | — | H | — | H | — | — | — | — | — | OCH₃ | CH₃ | |
| J₁₂ | — | O | — | — | — | H | — | CH₃ | — | — | — | — | — | OCH₃ | CH₃ | |
| J₁₃ | — | CH₂ | O | — | — | H | — | — | — | — | — | — | — | OCH₃ | OCH₃ | |
| J₁₃ | — | CH₂ | O | — | — | H | — | — | — | — | — | — | — | OCH₃ | CH₃ | |
| J₁₃ | — | O | O | — | — | H | — | — | — | — | — | — | — | OCH₃ | OCH₃ | |
| J₁₃ | — | O | O | — | — | H | — | — | — | — | — | — | — | OCH₃ | CH₃ | |
| J₁₃ | — | CH₂ | CH₂ | — | — | H | — | — | — | — | — | — | — | OCH₃ | OCH₃ | |
| J₁₃ | — | CH₂ | CH₂ | — | — | H | — | — | — | — | — | — | — | OCH₃ | CH₃ | |
| J₁₃ | — | O | CH₂ | — | — | H | — | — | — | — | — | — | — | OCH₃ | OCH₃ | |
| J₁₃ | — | O | CH₂ | — | — | H | — | — | — | — | — | — | — | OCH₃ | CH₃ | |
| J₁₄ | — | CH₂ | — | — | — | H | — | — | — | — | — | — | — | OCH₃ | OCH₃ | |
| J₁₄ | — | CH₂ | — | — | — | H | — | — | — | — | — | — | — | OCH₃ | CH₃ | |
| J₁₄ | — | O | — | — | — | H | — | — | — | — | — | — | — | OCH₃ | OCH₃ | |
| J₁₄ | — | O | — | — | — | H | — | — | — | — | — | — | — | OCH₃ | CH₃ | |
| J₁₅ | — | — | — | O | — | H | — | CH₃ | H | H | — | — | — | OCH₃ | OCH₃ | |
| J₁₅ | — | — | — | O | — | H | — | CH₃ | H | H | — | — | — | OCH₃ | CH₃ | |
| J₁₅ | — | — | — | O | — | H | — | H | H | CH₃ | — | — | — | CH₃ | CH₃ | |
| J₁₅ | — | — | — | O | — | H | — | H | H | CH₃ | — | — | — | OCH₃ | C₂H₅ | |
| J₁₅ | — | — | — | O | — | H | — | CH₃ | H | H | — | — | — | CH₃ | OC₂H₅ | |
| J₁₅ | — | — | — | O | — | H | — | CH₃ | H | H | — | — | — | OCH₃ | CH₂OCH₃ | |
| J₁₅ | — | — | — | O | — | H | — | H | H | C₂H₅ | — | — | — | OCH₃ | CF₃ | |
| J₁₅ | — | — | — | O | — | H | — | CH₃ | CH₃ | H | — | — | — | CH₃ | OCH₃ | |
| J₁₅ | — | — | — | SO₂ | — | H | — | H | H | H | — | — | — | CH₃ | CH₃ | |
| J₁₅ | — | — | — | SO₂ | — | H | — | H | H | H | — | — | — | CH₃ | OCH₃ | |
| J₁₅ | — | — | — | SO₂ | — | H | — | H | H | H | — | — | — | OCH₃ | OCH₃ | |
| J₁₅ | — | — | — | O | — | H | — | CH₃ | H | CH₃ | — | — | — | OCH₃ | OCH₃ | |
| J₁₅ | — | — | — | O | — | H | — | CH₃ | H | CH₃ | — | — | — | OCH₃ | CH₃ | |
| J₁₅ | — | — | — | O | — | H | — | CH₃ | H | CH₃ | — | — | — | CH₃ | CH₃ | |
| J₁₅ | — | — | — | O | — | H | — | CH₃ | H | CH₃ | — | — | — | OCH₃ | C₂H₅ | |
| J₁₅ | — | — | — | O | — | H | — | CH₃ | H | CH₃ | — | — | — | CH₃ | OC₂H₅ | |
| J₁₅ | — | — | — | O | — | H | — | CH₃ | H | CH₃ | — | — | — | OCH₃ | CH₂OCH₃ | |
| J₁₅ | — | — | — | O | — | H | — | CH₃ | H | CH₃ | — | — | — | OCH₃ | CH₂F | |
| J₁₅ | — | — | — | O | — | H | — | CH₃ | H | CH₃ | — | — | — | OCH₃ | CF₃ | |
| J₁₅ | — | — | — | S | — | H | — | CH₃ | H | H | — | — | — | OCH₃ | OCH₃ | |
| J₁₅ | — | — | — | S | — | H | — | CH₃ | H | H | — | — | — | OCH₃ | CH₃ | |
| J₁₅ | — | — | — | S | — | H | — | CH₃ | H | H | — | — | — | CH₃ | CH₃ | |
| J₁₅ | — | — | — | S | — | H | — | H | CH₃ | CH₃ | — | — | — | OCH₃ | CH₃ | |
| J₁₅ | — | — | — | SO₂ | — | H | — | H | H | H | — | — | — | CH₃ | CH₃ | |
| J₁₅ | — | — | — | SO₂ | — | H | — | H | H | H | — | — | — | CH₃ | OCH₃ | |
| J₁₅ | — | — | — | SO₂ | — | H | — | H | H | H | — | — | — | OCH₃ | OCH₃ | |
| J₁₅ | — | — | — | SO₂ | — | H | — | CH₃ | H | H | — | — | — | OCH₃ | OCH₃ | 192–194 |
| J₁₅ | — | — | — | SO₂ | — | H | — | CH₃ | H | H | — | — | — | OCH₃ | CH₃ | 186–187 |
| J₁₅ | — | — | — | SO₂ | — | H | — | CH₃ | H | H | — | — | — | CH₃ | CH₃ | |
| J₁₅ | — | — | — | SO₂ | — | H | — | CH₃ | H | H | — | — | — | OCH₃ | C₂H₅ | |
| J₁₅ | — | — | — | SO₂ | — | H | — | CH₃ | H | H | — | — | — | CH₃ | OC₂H₅ | |
| J₁₅ | — | — | — | SO₂ | — | H | — | CH₃ | H | H | — | — | — | OCH₃ | CH₂OCH₃ | |
| J₁₅ | — | — | — | SO₂ | — | H | — | CH₃ | H | H | — | — | — | OCH₃ | CH₂F | |
| J₁₅ | — | — | — | SO₂ | — | H | — | CH₃ | H | H | — | — | — | OCH₃ | CF₃ | |
| J₁₅ | — | — | — | SO₂ | — | H | — | CH₃ | CH₃ | H | — | — | — | OCH₃ | OCH₃ | |
| J₁₅ | — | — | — | SO₂ | — | H | — | CH₃ | H | CH₃ | — | — | — | OCH₃ | OCH₃ | |
| J₁₅ | — | — | — | SO₂ | — | H | — | CH₃ | H | CH₃ | — | — | — | OCH₃ | CH₃ | |
| J₁₅ | — | — | — | SO₂ | — | H | — | CH₃ | H | CH₃ | — | — | — | CH₃ | CH₃ | |
| J₁₅ | — | — | — | SO₂ | — | H | — | CH₃ | H | CH₃ | — | — | — | OCH₃ | C₂H₅ | |
| J₁₅ | — | — | — | SO₂ | — | H | — | CH₃ | H | CH₃ | — | — | — | CH₃ | OC₂H₅ | |
| J₁₅ | — | — | — | SO₂ | — | H | — | CH₃ | H | CH₃ | — | — | — | OCH₃ | CH₂OCH₃ | |
| J₁₅ | — | — | — | SO₂ | — | H | — | CH₃ | H | CH₃ | — | — | — | OCH₃ | CH₂F | |
| J₁₅ | — | — | — | SO₂ | — | H | — | CH₃ | H | CH₃ | — | — | — | OCH₃ | CF₃ | |
| J₁₅ | — | — | — | S | — | H | — | CH₃ | H | CH₃ | — | — | — | OCH₃ | OCH₃ | |
| J₁₅ | — | — | — | S | — | H | — | CH₃ | H | CH₃ | — | — | — | OCH₃ | CH₃ | |
| J₁₅ | — | — | — | S | — | H | — | CH₃ | H | CH₃ | — | — | — | CH₃ | CH₃ | |
| J₁₅ | — | — | — | SO₂ | — | 6-Cl | — | CH₃ | H | H | — | — | — | CH₃ | CH₃ | |
| J₁₅ | — | — | — | SO₂ | — | 6-Cl | — | CH₃ | H | H | — | — | — | OCH₃ | OCH₃ | |
| J₁₅ | — | — | — | O | — | 6-Cl | — | CH₃ | H | H | — | — | — | CH₃ | OCH₃ | |
| J₁₅ | — | — | — | O | — | 5-Br | — | H | H | CH₃ | — | — | — | CH₃ | OCH₃ | |
| J₁₅ | — | — | — | O | — | 6-F | — | CH₃ | H | H | — | — | — | CH₃ | OCH₃ | |
| J₁₅ | — | — | — | O | — | 5-CH₃ | — | CH₃ | H | H | — | — | — | CH₃ | OCH₃ | |
| J₁₅ | — | — | — | O | — | 6-OCH₃ | — | CH₃ | H | H | — | — | — | CH₃ | OCH₃ | |
| J₁₅ | — | — | — | SO₂ | — | 6-Cl | — | CH₃ | H | H | — | — | — | CH₃ | OCH₃ | |
| J₁₅ | — | — | — | S | — | 6-Cl | — | CH₃ | H | H | — | — | — | CH₃ | OCH₃ | |
| J₁₆ | — | CH₂ | — | O | — | H | — | CH₃ | H | — | — | — | — | CH₃ | OCH₃ | |
| J₁₆ | — | CH₂ | — | S | — | H | — | H | CH₃ | — | — | — | — | CH₃ | OCH₃ | |

TABLE 2a-continued

General Formula 2a

| J | n | L | Q | $Q_1$ | $Q_2$ | $R_1$ | $R_2$ | $R_3$ | $R_4$ | $R_5$ | $R_6$ | $R_7$ | $R_8$ | X | Y | m.p. (°C.) |
|---|---|---|---|---|---|---|---|---|---|---|---|---|---|---|---|---|
| $J_{16}$ | — | O | — | $SO_2$ | — | H | — | $CH_3$ | H | — | — | — | — | $CH_3$ | $OCH_3$ | |
| $J_{16}$ | — | O | — | $SO_2$ | — | H | — | $CH_3$ | H | — | — | — | — | $CH_3$ | $CH_3$ | |
| $J_{17}$ | — | — | — | — | O | H | — | $CH_3$ | H | — | — | — | — | $CH_3$ | $OCH_3$ | |
| $J_{17}$ | — | — | — | — | S | H | — | $CH_3$ | H | — | — | — | — | $CH_3$ | $OCH_3$ | |
| $J_{17}$ | — | — | — | — | O | H | — | $CH_3$ | $CH_3$ | — | — | — | — | $CH_3$ | $OCH_3$ | |
| $J_{17}$ | — | — | — | — | O | H | — | H | H | — | — | — | — | $CH_3$ | $OCH_3$ | |
| $J_{18}$ | — | $CH_2$ | — | — | — | H | — | H | H | — | H | H | — | $CH_3$ | $OCH_3$ | |
| $J_{18}$ | — | $CH_2$ | — | — | — | H | — | H | H | — | $CH_3$ | H | — | $OCH_3$ | $CH_3$ | |
| $J_{18}$ | — | O | — | — | — | H | — | H | H | — | H | $CH_3$ | — | $OCH_3$ | $OCH_3$ | |
| $J_{19}$ | — | — | — | — | — | H | — | $CH_3$ | $CH_3$ | — | — | — | — | $CH_3$ | $OCH_3$ | |
| $J_{19}$ | — | — | — | — | — | H | — | H | H | — | — | — | — | $OCH_3$ | $OCH_3$ | |
| $J_{19}$ | — | — | — | — | — | H | — | H | H | — | — | — | — | $OCH_3$ | $CH_3$ | |
| $J_{19}$ | — | — | — | — | — | H | — | $CH_3$ | $CH_3$ | — | — | — | — | $OCH_3$ | $CH_3$ | |
| $J_{20}$ | — | $CH_2$ | — | — | — | H | — | — | — | — | — | — | — | $OCH_3$ | $OCH_3$ | |
| $J_{20}$ | — | $CH_2$ | — | — | — | H | — | — | — | — | — | — | — | $OCH_3$ | $CH_3$ | |
| $J_{20}$ | — | $CH_2$ | — | — | — | H | — | — | — | — | — | — | — | $CH_3$ | $CH_3$ | |
| $J_{20}$ | — | $CH_2$ | — | — | — | 7-Cl | — | — | — | — | — | — | — | $OCH_3$ | $OCH_3$ | |
| $J_{20}$ | — | O | — | — | — | H | — | — | — | — | — | — | — | $OCH_3$ | $OCH_3$ | |
| $J_{20}$ | — | O | — | — | — | H | — | — | — | — | — | — | — | $OCH_3$ | $CH_3$ | |
| $J_{20}$ | — | O | — | — | — | H | — | — | — | — | — | — | — | $CH_3$ | $CH_3$ | |
| $J_{21}$ | — | $CH_2$ | — | — | — | — | — | — | — | — | — | — | F | $OCH_3$ | $CH_3$ | |
| $J_{21}$ | — | $CH_2$ | — | — | — | — | — | — | — | — | — | — | Cl | $OCH_3$ | $CH_3$ | |
| $J_{21}$ | — | $CH_2$ | — | — | — | — | — | — | — | — | — | — | Br | $OCH_3$ | $CH_3$ | |
| $J_{21}$ | — | $CH_2$ | — | — | — | — | — | — | — | — | — | — | $OCH_3$ | $OCH_3$ | $OCH_3$ | |
| $J_{21}$ | — | $CH_2$ | — | — | — | — | — | — | — | — | — | — | $SCH_3$ | $OCH_3$ | $CH_3$ | |
| $J_{21}$ | — | $CH_2$ | — | — | — | — | — | — | — | — | — | — | $SO_2CH_3$ | $OCH_3$ | $CH_3$ | |
| $J_{21}$ | — | $CH_2$ | — | — | — | — | — | — | — | — | — | — | $CO_2CH_3$ | $OCH_3$ | $OCH_3$ | 122–122.5 |
| $J_{21}$ | — | $CH_2$ | — | — | — | — | — | — | — | — | — | — | $SO_2N(CH_3)_2$ | $OCH_3$ | $CH_3$ | |
| $J_{21}$ | — | $CH_2$ | — | — | — | — | — | — | — | — | — | — | $OSO_2CH_3$ | $OCH_3$ | $CH_3$ | |
| $J_{21}$ | — | $CH_2$ | — | — | — | — | — | — | — | — | — | — | Cl | $OCH_3$ | $CF_3$ | |
| $J_{21}$ | — | $CH_2$ | — | — | — | — | — | — | — | — | — | — | Cl | $CH_3$ | $OC_2H_5$ | |
| $J_{21}$ | — | $CH_2$ | — | — | — | — | — | — | — | — | — | — | Cl | $OCH_3$ | $C_2H_5$ | |
| $J_{21}$ | — | O | — | — | — | — | — | — | — | — | — | — | F | $OCH_3$ | $CH_3$ | |
| $J_{21}$ | — | O | — | — | — | — | — | — | — | — | — | — | Cl | $OCH_3$ | $CH_3$ | |
| $J_{21}$ | — | O | — | — | — | — | — | — | — | — | — | — | Br | $OCH_3$ | $CH_3$ | |
| $J_{21}$ | — | O | — | — | — | — | — | — | — | — | — | — | $OCH_3$ | $OCH_3$ | $CH_3$ | |
| $J_{21}$ | — | O | — | — | — | — | — | — | — | — | — | — | $SCH_3$ | $OCH_3$ | $CH_3$ | |
| $J_{21}$ | — | O | — | — | — | — | — | — | — | — | — | — | $SO_2CH_3$ | $OCH_3$ | $CH_3$ | |
| $J_{21}$ | — | O | — | — | — | — | — | — | — | — | — | — | $CO_2CH_3$ | $OCH_3$ | $CH_3$ | |
| $J_{21}$ | — | O | — | — | — | — | — | — | — | — | — | — | $SO_2N(CH_3)_2$ | $OCH_3$ | $CH_3$ | |
| $J_{21}$ | — | O | — | — | — | — | — | — | — | — | — | — | $OSO_2CH_3$ | $OCH_3$ | $CH_3$ | |
| $J_{21}$ | — | $CH_2$ | — | — | — | — | — | — | — | — | — | — | $CO_2CH_3$ | $OCH_3$ | $CH_3$ | 187–190 |
| $J_{21}$ | — | $CH_2$ | — | — | — | — | — | — | — | — | — | — | $CO_2CH_3$ | $CH_3$ | $OC_2H_5$ | |
| $J_{21}$ | — | $CH_2$ | — | — | — | — | — | — | — | — | — | — | $CO_2CH_3$ | $OCH_3$ | $CF_3$ | |
| $J_{21}$ | — | $CH_2$ | — | — | — | — | — | — | — | — | — | — | $CO_2CH_3$ | $OCH_3$ | $C_2H_5$ | |
| $J_2$ | 0 | $CH_2$ | — | — | — | H | $CH_3$ | — | — | — | — | — | — | $OCH_3$ | $CH(CH_3)_2$ | |
| $J_2$ | 0 | $CH_2$ | — | — | — | H | $CH_3$ | — | — | — | — | — | — | $OCH_2CF_3$ | $OCH_3$ | |
| $J_2$ | 0 | $CH_2$ | — | — | — | H | $CH_3$ | — | — | — | — | — | — | $OCH_3$ | cyclopropyl | |
| $J_2$ | 0 | $CH_2$ | — | — | — | H | $CH_3$ | — | — | — | — | — | — | $OCH_3$ | $NHCH_3$ | |
| $J_2$ | 0 | $CH_2$ | — | — | — | H | $CH_3$ | — | — | — | — | — | — | $OCH_3$ | $N(CH_3)_2$ | |
| $J_2$ | 0 | $CH_2$ | — | — | — | H | $CH_3$ | — | — | — | — | — | — | $OCH_3$ | $OCH_2CH=CH_2$ | |
| $J_2$ | 0 | $CH_2$ | — | — | — | H | $CH_3$ | — | — | — | — | — | — | $OCH_3$ | $CH(OCH_3)_2$ | |
| $J_2$ | 0 | $CH_2$ | — | — | — | H | $CH_3$ | — | — | — | — | — | — | $OCH_3$ | 1,3-dioxolan-2-yl |  |
| $J_2$ | 0 | $CH_2$ | — | — | — | H | $CH_3$ | — | — | — | — | — | — | $OCH_3$ | $CH(OC_2H_5)_2$ | |
| $J_2$ | 0 | $CH_2$ | — | — | — | H | $CH_3$ | — | — | — | — | — | — | $OCH_3$ | $C\equiv CH$ | |
| $J_2$ | 0 | $CH_2$ | — | — | — | H | $CH_3$ | — | — | — | — | — | — | $OCH_3$ | $OCH_2CH_2OCH_3$ | |
| $J_2$ | 0 | $CH_2$ | — | — | — | H | $CH_3$ | — | — | — | — | — | — | $OCH_3$ | $SCH_3$ | |
| $J_3$ | 0 | $CH_2$ | — | — | — | H | $CH_3$ | — | — | — | — | — | — | $OCH_3$ | $NHCH_3$ | |
| $J_3$ | 0 | $CH_2$ | — | — | — | H | $CH_3$ | — | — | — | — | — | — | $OCF_2H$ | $OCH_3$ | |
| $J_3$ | 0 | $CH_2$ | — | — | — | H | $CH_3$ | — | — | — | — | — | — | $OCH_3$ | cyclopropyl | |
| $J_3$ | 0 | $CH_2$ | — | — | — | H | $CH_3$ | — | — | — | — | — | — | $OCH_3$ | $CH(OCH_3)_2$ | |
| $J_3$ | 0 | $CH_2$ | — | — | — | H | $CH_3$ | — | — | — | — | — | — | $OCH_3$ | $C\equiv CH$ | |
| $J_3$ | 0 | $CH_2$ | — | — | — | H | $CH_3$ | — | — | — | — | — | — | $OCH_3$ | $OCH_2CH_2OCH_3$ | |
| $J_3$ | 0 | $CH_2$ | — | — | — | H | $CH_3$ | — | — | — | — | — | — | $CH_3$ | 1,3-dioxolan-2-yl | |
| $J_3$ | 0 | $CH_2$ | — | — | — | H | $CH_3$ | — | — | — | — | — | — | $CH_3$ | $OCH_2C\equiv CH$ | |
| $J_4$ | 0 | $CH_2$ | — | — | — | H | — | H | H | — | — | — | — | $OCH_3$ | $CH_2CH_2CH_3$ | |
| $J_4$ | 0 | $CH_2$ | — | — | — | H | — | H | H | — | — | — | — | $OCH_3$ | cyclopropyl | |
| $J_4$ | 0 | $CH_2$ | — | — | — | H | — | H | H | — | — | — | — | $OCH_3$ | $C\equiv CH$ | |
| $J_4$ | 0 | $CH_2$ | — | — | — | H | — | H | H | — | — | — | — | $OCH_3$ | $OCH_2CH=CH_2$ | |
| $J_4$ | 0 | $CH_2$ | — | — | — | H | — | H | H | — | — | — | — | $OCH_3$ | $OCH_2CH_2F$ | |
| $J_5$ | 0 | — | — | — | — | H | $CH_3$ | — | — | — | — | — | — | $OCH_3$ | $CH(CH_3)_2$ | |
| $J_5$ | 0 | — | — | — | — | H | $CH_3$ | — | — | — | — | — | — | $OCH_3$ | cyclopropyl | |
| $J_5$ | 0 | — | — | — | — | H | $CH_3$ | — | — | — | — | — | — | $OCH_3$ | $C\equiv CH$ | |
| $J_5$ | 0 | — | — | — | — | H | $CH_3$ | — | — | — | — | — | — | $OCH_3$ | $OCH_2C\equiv CH$ | |
| $J_5$ | 0 | — | — | — | — | H | $CH_3$ | — | — | — | — | — | — | $OCH_3$ | $OCH_2CH_2F$ | |

TABLE 2a-continued

General Formula 2a

| J | n | L | Q | $Q_1$ | $Q_2$ | $R_1$ | $R_2$ | $R_3$ | $R_4$ | $R_5$ | $R_6$ | $R_7$ | $R_8$ | X | Y | m.p. (°C.) |
|---|---|---|---|---|---|---|---|---|---|---|---|---|---|---|---|---|
| $J_5$ | 0 | — | — | — | — | H | $CH_3$ | — | — | — | — | — | — | $OCH_3$ | $SCH_3$ | |
| $J_5$ | 0 | — | — | — | — | H | $CH_3$ | — | — | — | — | — | — | $OCH_3$ | $CH(OCH_3)_2$ | |
| $J_5$ | 0 | — | — | — | — | H | $CH_3$ | — | — | — | — | — | — | $OCH_3$ | 1,3-dioxolan-2-yl | |
| $J_6$ | 0 | $CH_2$ | — | — | — | H | $CH_3$ | — | — | — | — | — | — | $OCH_3$ | $CH(CH_3)_2$ | |
| $J_6$ | 0 | $CH_2$ | — | — | — | H | $CH_3$ | — | — | — | — | — | — | $OCH_3$ | cyclopropyl | |
| $J_6$ | 0 | $CH_2$ | — | — | — | H | $CH_3$ | — | — | — | — | — | — | $OCH_3$ | C≡CH | |
| $J_6$ | 0 | $CH_2$ | — | — | — | H | $CH_3$ | — | — | — | — | — | — | $OCH_3$ | $OCH_2CH_2F$ | |
| $J_6$ | 0 | $CH_2$ | — | — | — | H | $CH_3$ | — | — | — | — | — | — | $OCH_3$ | $SCH_3$ | |
| $J_6$ | 0 | $CH_2$ | — | — | — | H | $CH_3$ | — | — | — | — | — | — | $OCH_3$ | $CH(OCH_3)_2$ | |
| $J_8$ | — | $CH_2$ | — | — | — | H | — | — | — | — | — | — | — | $OCH_3$ | $NHCH_3$ | |
| $J_8$ | — | $CH_2$ | — | — | — | H | — | — | — | — | — | — | — | $OCH_3$ | C≡CH | |
| $J_8$ | — | $CH_2$ | — | — | — | H | — | — | — | — | — | — | — | $OCH_3$ | $NHCH_3$ | |
| $J_8$ | — | $CH_2$ | — | — | — | H | — | — | — | — | — | — | — | $OCH_3$ | $CH(OCH_3)_2$ | |
| $J_8$ | — | $CH_2$ | — | — | — | H | — | — | — | — | — | — | — | $OCH_3$ | $OCH_2C≡CH$ | |
| $J_8$ | — | $CH_2$ | — | — | — | H | — | — | — | — | — | — | — | $OCH_3$ | $OCH_2CH_2F$ | |
| $J_8$ | — | $CH_2$ | — | — | — | H | — | — | — | — | — | — | — | $OCH_3$ | $SCH_3$ | |
| $J_8$ | — | $CH_2$ | — | — | — | H | — | — | — | — | — | — | — | $OCH_3$ | 1,3-dioxolan-2-yl | |
| $J_8$ | — | $CH_2$ | — | — | — | H | — | — | — | — | — | — | — | $OCH_3$ | cyclopropyl | |
| $J_9$ | — | O | — | — | — | H | — | — | — | — | — | — | — | $OCH_3$ | $CH(OCH_3)_2$ | |
| $J_9$ | — | O | — | — | — | H | — | — | — | — | — | — | — | $OCH_3$ | $N(CH_3)_2$ | |
| $J_9$ | — | O | — | — | — | H | — | — | — | — | — | — | — | $OCH_3$ | $NHCH_3$ | |
| $J_{10}$ | — | — | — | — | — | H | $CH_3$ | — | — | — | — | — | — | $OCH_3$ | $NHCH_3$ | |
| $J_{10}$ | — | — | — | — | — | H | $CH_3$ | — | — | — | — | — | — | $CH_3$ | $CH(OCH_3)_2$ | |
| $J_{11}$ | — | — | — | — | — | H | $CH_3$ | — | — | — | — | — | — | $OCH_3$ | $CH(OCH_3)_2$ | |
| $J_{11}$ | — | — | — | — | — | H | — | — | — | — | — | — | — | $OCH_3$ | $NHCH_3$ | |
| $J_{12}$ | — | O | — | — | — | H | — | — | — | — | — | — | — | $CH_3$ | $NHCH_3$ | |
| $J_{12}$ | — | O | — | — | — | H | — | — | — | — | — | — | — | $OCH_3$ | $N(CH_3)_2$ | |
| $J_{12}$ | — | O | — | — | — | H | — | — | — | — | — | — | — | $OCH_3$ | 1,3-dioxolan-2-yl | |
| $J_{13}$ | — | $CH_2$ | $CH_2$ | — | — | H | — | — | — | — | — | — | — | $OCH_3$ | $NHCH_3$ | |
| $J_{13}$ | — | $CH_2$ | $CH_2$ | — | — | H | — | — | — | — | — | — | — | $OCH_3$ | $SCH_3$ | |
| $J_{13}$ | — | $CH_2$ | $CH_2$ | — | — | H | — | — | — | — | — | — | — | $OCH_3$ | $CH(OCH_3)_2$ | |
| $J_{13}$ | — | $CH_2$ | $CH_2$ | — | — | H | — | — | — | — | — | — | — | $OCH_3$ | $OCH_2CH=CH$ | |
| $J_{14}$ | — | $CH_2$ | — | — | — | H | — | — | — | — | — | — | — | $OCH_3$ | $OCH_2CH=CH_2$ | |
| $J_{14}$ | — | $CH_2$ | — | — | — | H | — | — | — | — | — | — | — | $CH_3$ | $OCH_2CH_2F$ | |
| $J_{14}$ | — | $CH_2$ | — | — | — | H | — | — | — | — | — | — | — | $OCH_2CF_3$ | $OCH_3$ | |
| $J_{14}$ | — | $CH_2$ | — | — | — | H | — | — | — | — | — | — | — | $OCH_3$ | $OCH_2CH_2OCH_3$ | |
| $J_{15}$ | — | — | — | O | — | H | — | $CH_3$ | H | H | — | — | — | $OCH_3$ | $NHCH_3$ | |
| $J_{15}$ | — | — | — | O | — | H | — | $CH_3$ | H | H | — | — | — | $OCH_3$ | $OCH_2CH=CH_2$ | |
| $J_{15}$ | — | — | — | O | — | H | — | H | H | H | — | — | — | $OCH_3$ | C≡CH | |
| $J_{15}$ | — | — | — | O | — | H | — | H | H | H | — | — | — | $OCH_3$ | $OCH_2CH_2F$ | |
| $J_{15}$ | — | — | — | O | — | H | — | $CH_3$ | H | H | — | — | — | $OCH_3$ | $OCH_2CH=CHCl$ | |
| $J_{15}$ | — | — | — | O | — | H | — | H | H | H | — | — | — | $CH_3$ | $NHCH_3$ | |
| $J_{15}$ | — | — | — | O | — | H | — | H | H | $CH_3$ | — | — | — | $OCH_3$ | $N(CH_3)_2$ | |
| $J_{15}$ | — | — | — | O | — | H | — | H | H | $CH_3$ | — | — | — | $OCH_3$ | cyclopropyl | |
| $J_{15}$ | — | — | — | O | — | H | — | H | H | $CH_3$ | — | — | — | $OCH_3$ | $CH(OCH_3)_2$ | |
| $J_{15}$ | — | — | — | O | — | H | — | $CH_3$ | $CH_3$ | H | — | — | — | $OCH_3$ | $NHCH_3$ | |
| $J_{15}$ | — | — | — | O | — | H | — | $CH_3$ | $CH_3$ | H | — | — | — | $OCH_3$ | $CH(OCH_3)_2$ | |
| $J_{15}$ | — | — | — | O | — | H | — | $CH_3$ | H | H | — | — | — | $OCH_3$ | $OCH_2C≡CH$ | |
| $J_{15}$ | — | — | — | O | — | H | — | $CH_3$ | $CH_3$ | H | — | — | — | $OCH_3$ | $SCH_3$ | |
| $J_{15}$ | — | — | — | S | — | H | — | $CH_3$ | H | H | — | — | — | $OCH_3$ | $NHCH_3$ | |
| $J_{15}$ | — | — | — | S | — | H | — | $CH_3$ | H | H | — | — | — | $OCH_3$ | $N(CH_3)_2$ | |
| $J_{15}$ | — | — | — | S | — | H | — | $CH_3$ | H | H | — | — | — | $OCH_3$ | $OCH_2CH=CH_2$ | |
| $J_{15}$ | — | — | — | S | — | H | — | $CH_3$ | H | H | — | — | — | $OCH_3$ | cyclopropyl | |
| $J_{15}$ | — | — | — | S | — | H | — | $CH_3$ | H | H | — | — | — | $OCH_3$ | $N(CH_3)_2$ | |
| $J_{15}$ | — | — | — | S | — | H | — | $CH_3$ | $CH_3$ | $CH_3$ | — | — | — | $OCH_3$ | $CH(OCH_3)_2$ | |
| $J_{15}$ | — | — | — | $SO_2$ | — | H | — | $CH_3$ | H | H | — | — | — | $OCH_3$ | $NHCH_3$ | |
| $J_{15}$ | — | — | — | $SO_2$ | — | H | — | $CH_3$ | H | H | — | — | — | $OCH_3$ | $N(CH_3)_2$ | |
| $J_{15}$ | — | — | — | $SO_2$ | — | H | — | $CH_3$ | H | H | — | — | — | $OCH_3$ | $OCH_2CH=CH_2$ | |
| $J_{15}$ | — | — | — | $SO_2$ | — | H | — | $CH_3$ | H | H | — | — | — | $CH_3$ | $OCH_2CH_2OCH_3$ | |
| $J_{15}$ | — | — | — | $SO_2$ | — | H | — | $CH_3$ | H | H | — | — | — | $CH_3$ | $CH(OCH_3)_2$ | |
| $J_{16}$ | — | $CH_2$ | — | O | — | H | — | $CH_3$ | H | — | — | — | — | $OCH_3$ | $N(CH_3)_2$ | |
| $J_{16}$ | — | $CH_2$ | — | S | — | H | — | H | $CH_3$ | — | — | — | — | $OCH_3$ | $OCH_2CH=CH_2$ | |
| $J_{16}$ | — | O | — | $SO_2$ | — | H | — | $CH_3$ | H | — | — | — | — | $OCH_3$ | $OCH_2CH_2F$ | |
| $J_{16}$ | — | O | — | $SO_2$ | — | H | — | $CH_3$ | H | — | — | — | — | $OCH_3$ | $OCH_2CH_2OCH_3$ | |
| $J_{17}$ | — | — | — | — | O | H | — | $CH_3$ | H | — | — | — | — | $OCH_3$ | $N(CH_3)_2$ | |
| $J_{17}$ | — | — | — | — | O | H | — | $CH_3$ | H | — | — | — | — | $CH_3$ | $CH(OCH_3)_2$ | |
| $J_{17}$ | — | — | — | — | S | H | — | $CH_3$ | H | — | — | — | — | $OCH_3$ | $NHCH_3$ | |
| $J_{18}$ | — | $CH_2$ | — | — | — | H | — | H | H | — | H | H | — | $OCH_3$ | $NHCH_3$ | |
| $J_{18}$ | — | $CH_2$ | — | — | — | H | — | H | H | — | $CH_3$ | H | — | $OCH_3$ | $N(CH_3)_2$ | |
| $J_{18}$ | — | O | — | — | — | H | — | H | H | — | H | $CH_3$ | — | $CH_3$ | $OCH_2CH_2OCH_3$ | |
| $J_{19}$ | — | — | — | — | — | H | — | H | H | — | — | — | — | $CH_3$ | $OCH_2CH_2F$ | |
| $J_{19}$ | — | — | — | — | — | H | — | $CH_3$ | $CH_3$ | — | — | — | — | $OCH_3$ | $NHCH_3$ | |
| $J_{19}$ | — | — | — | — | — | H | — | H | $CH_3$ | — | — | — | — | $OCH_3$ | C≡CH | |
| $J_{20}$ | — | $CH_2$ | — | — | — | H | — | — | — | — | — | — | — | $OCH_3$ | $NHCH_3$ | |
| $J_{20}$ | — | $CH_2$ | — | — | — | H | — | — | — | — | — | — | — | $CH_3$ | $OCH_2CH_2F$ | |
| $J_{20}$ | — | O | — | — | — | H | — | — | — | — | — | — | — | $OCH_3$ | C≡CH | |

TABLE 2a-continued

General Formula 2a

| J | n | L | Q | $Q_1$ | $Q_2$ | $R_1$ | $R_2$ | $R_3$ | $R_4$ | $R_5$ | $R_6$ | $R_7$ | $R_8$ | X | Y | m.p. (°C.) |
|---|---|---|---|---|---|---|---|---|---|---|---|---|---|---|---|---|
| $J_{20}$ | — | O | — | — | — | H | — | — | — | — | — | — | — | $OCH_3$ | $CH(OCH_3)_2$ | |
| $J_{21}$ | — | $CH_2$ | — | — | — | — | — | — | — | — | — | — | Cl | $OCH_3$ | $NHCH_3$ | |
| $J_{21}$ | — | $CH_2$ | — | — | — | — | — | — | — | — | — | — | Br | $OCH_3$ | $N(CH_3)_2$ | |
| $J_{21}$ | — | $CH_2$ | — | — | — | — | — | — | — | — | — | — | F | $OCH_3$ | $NHCH_3$ | |
| $J_{21}$ | — | $CH_2$ | — | — | — | — | — | — | — | — | — | — | $OCH_3$ | $OCH_3$ | $NHCH_3$ | |
| $J_{21}$ | — | $CH_2$ | — | — | — | — | — | — | — | — | — | — | $SO_2N(CH_3)_2$ | $OCH_3$ | $C{\equiv}CH$ | |
| $J_{21}$ | — | $CH_2$ | — | — | — | — | — | — | — | — | — | — | Cl | $OCH_3$ | $OCH_2CH_2F$ | |
| $J_{21}$ | — | O | — | — | — | — | — | — | — | — | — | — | Cl | $OCH_3$ | $NHCH_3$ | |
| $J_{21}$ | — | O | — | — | — | — | — | — | — | — | — | — | Br | $OCH_3$ | $NHCH_3$ | |
| $J_{21}$ | — | O | — | — | — | — | — | — | — | — | — | — | $OCH_3$ | $OCH_3$ | $NHCH_3$ | |
| $J_{21}$ | — | O | — | — | — | — | — | — | — | — | — | — | $SO_2N(CH_3)_2$ | $OCH_3$ | $NHCH_3$ | |
| $J_{21}$ | — | O | — | — | — | — | — | — | — | — | — | — | $SO_2CH_3$ | $OCH_3$ | $NHCH_3$ | |

TABLE 3

General Formula 3

| J | n | L | Q | $Q_1$ | $Q_2$ | $R_1$ | $R_2$ | $R_3$ | $R_4$ | $R_5$ | $R_6$ | $R_7$ | $R_8$ | $R_9$ | $X_1$ | $Y_1$ | m.p. (°C.) |
|---|---|---|---|---|---|---|---|---|---|---|---|---|---|---|---|---|---|
| $J_1$ | 0 | $CH_2$ | — | — | — | H | — | — | — | — | — | — | — | $CH_3$ | $OCH_3$ | O | |
| $J_1$ | 0 | $CH_2$ | — | — | — | H | — | — | — | — | — | — | — | $CH_3$ | $CH_3$ | O | |
| $J_1$ | 0 | $CH_2$ | — | — | — | H | — | — | — | — | — | — | — | $CH_3$ | $OCH_3$ | $CH_2$ | |
| $J_1$ | 0 | $CH_2$ | — | — | — | H | — | — | — | — | — | — | — | $CH_3$ | $OC_2H_5$ | O | |
| $J_1$ | 0 | $CH_2$ | — | — | — | H | — | — | — | — | — | — | — | $CH_3$ | $OCF_2H$ | O | |
| $J_1$ | 0 | O | — | — | — | H | — | — | — | — | — | — | — | $CH_3$ | $OCH_3$ | $CH_2$ | |
| $J_1$ | 0 | O | — | — | — | H | — | — | — | — | — | — | — | $CH_3$ | $CH_3$ | O | |
| $J_1$ | 0 | O | — | — | — | H | — | — | — | — | — | — | — | $CH_3$ | $OCF_2H$ | O | |
| $J_2$ | 0 | $CH_2$ | — | — | — | H | $CH_3$ | — | — | — | — | — | — | — | $OCH_3$ | O | |
| $J_2$ | 0 | $CH_2$ | — | — | — | H | $CH_3$ | — | — | — | — | — | — | — | $CH_3$ | O | |
| $J_2$ | 0 | $CH_2$ | — | — | — | H | $CH_3$ | — | — | — | — | — | — | — | $OCH_3$ | $CH_2$ | |
| $J_2$ | 0 | O | — | — | — | H | $CH_3$ | — | — | — | — | — | — | — | $OCF_2H$ | O | |
| $J_2$ | 1 | $CH_2$ | — | — | — | H | $CH_3$ | — | — | — | — | — | — | — | $OCH_3$ | $CH_2$ | |
| $J_2$ | 1 | $CH_2$ | — | — | — | H | $CH_3$ | — | — | — | — | — | — | — | $CH_3$ | O | |
| $J_2$ | 1 | O | — | — | — | H | $CH_3$ | — | — | — | — | — | — | — | $OCH_3$ | O | |
| $J_3$ | 0 | $CH_2$ | — | — | — | H | — | H | H | — | — | — | — | — | $OCH_3$ | O | |
| $J_3$ | 0 | $CH_2$ | — | — | — | H | — | H | H | — | — | — | — | — | $CH_3$ | O | |
| $J_3$ | 0 | $CH_2$ | — | — | — | H | — | H | H | — | — | — | — | — | $OCH_3$ | $CH_2$ | |
| $J_3$ | 0 | $CH_2$ | — | — | — | H | — | H | H | — | — | — | — | — | $OCF_2H$ | O | |
| $J_3$ | 1 | $CH_2$ | — | — | — | H | — | H | H | — | — | — | — | — | $OCH_3$ | O | |
| $J_3$ | 1 | $CH_2$ | — | — | — | H | — | H | H | — | — | — | — | — | $OCH_3$ | $CH_2$ | |
| $J_3$ | 1 | $CH_2$ | — | — | — | H | — | H | H | — | — | — | — | — | $OC_2H_5$ | O | |
| $J_3$ | 1 | O | — | — | — | H | — | H | H | — | — | — | — | — | $OCH_3$ | O | |
| $J_4$ | 0 | $CH_2$ | — | — | — | H | — | — | — | — | — | — | — | — | $OCH_3$ | $CH_2$ | |
| $J_4$ | 0 | O | — | — | — | H | — | — | — | — | — | — | — | — | $OCH_3$ | O | |
| $J_4$ | 1 | $CH_2$ | — | — | — | H | — | — | — | — | — | — | — | — | $CH_3$ | O | |
| $J_5$ | 0 | — | — | — | — | H | $CH_3$ | — | — | — | — | — | — | — | $OCH_3$ | $CH_2$ | |
| $J_5$ | 0 | — | — | — | — | H | $CH_3$ | — | — | — | — | — | — | — | $OCH_3$ | O | |
| $J_5$ | 0 | — | — | — | — | H | $CH_3$ | — | — | — | — | — | — | — | $CH_3$ | O | |
| $J_6$ | 0 | — | — | — | — | H | $CH_3$ | — | — | — | — | — | — | — | $OCH_3$ | $CH_2$ | |
| $J_7$ | — | $CH_2$ | — | — | — | H | $CH_3$ | — | — | — | — | — | — | $CH_3$ | $OCH_3$ | $CH_2$ | |
| $J_7$ | — | $CH_2$ | — | — | — | H | $CH_3$ | — | — | — | — | — | — | $CH_3$ | $CH_3$ | O | |
| $J_8$ | — | $CH_2$ | — | — | — | H | — | H | — | — | — | — | — | — | $OCH_3$ | O | |
| $J_8$ | — | O | — | — | — | H | — | H | — | — | — | — | — | — | $CH_3$ | O | |
| $J_9$ | — | $CH_2$ | — | — | — | H | — | — | — | — | — | — | — | — | $OCH_3$ | $CH_2$ | |
| $J_{10}$ | — | — | — | — | — | H | $CH_3$ | — | — | — | — | — | — | $OCH_3$ | $CH_2$ | | |
| $J_{10}$ | — | — | — | — | — | H | $CH_3$ | — | — | — | — | — | — | — | $OCH_3$ | O | |
| $J_{11}$ | — | — | — | — | — | H | $CH_3$ | — | — | — | — | — | — | — | $OCH_3$ | O | |
| $J_{12}$ | — | $CH_2$ | — | — | — | H | — | H | — | — | — | — | — | — | $OCH_3$ | $CH_2$ | |
| $J_{12}$ | — | $CH_2$ | — | — | — | H | — | H | — | — | — | — | — | — | $OCH_3$ | O | |
| $J_{12}$ | — | O | — | — | — | H | — | H | — | — | — | — | — | — | $CH_3$ | O | |
| $J_{12}$ | — | O | — | — | — | H | — | H | — | — | — | — | — | — | $OCH_3$ | $CH_2$ | |
| $J_{13}$ | — | $CH_2$ | O | — | — | H | — | — | — | — | — | — | — | — | $OCH_3$ | $CH_2$ | |
| $J_{13}$ | — | O | O | — | — | H | — | — | — | — | — | — | — | — | $CH_3$ | O | |
| $J_{13}$ | — | $CH_2$ | $CH_2$ | — | — | H | — | — | — | — | — | — | — | — | $OCH_3$ | O | |
| $J_{14}$ | — | $CH_2$ | — | — | — | H | — | — | — | — | — | — | — | — | $OCH_3$ | O | |
| $J_{14}$ | — | $CH_2$ | — | — | — | H | — | — | — | — | — | — | — | — | $CH_3$ | O | |
| $J_{14}$ | — | O | — | — | — | H | — | — | — | — | — | — | — | — | $OCH_3$ | $CH_2$ | |
| $J_{15}$ | — | — | — | O | — | H | $CH_3$ | H | H | — | — | — | — | — | $OCH_3$ | O | |
| $J_{15}$ | — | — | — | O | — | H | $CH_3$ | H | H | — | — | — | — | — | $OCH_3$ | $CH_2$ | |
| $J_{15}$ | — | — | — | O | — | H | $CH_3$ | H | H | — | — | — | — | — | $CH_3$ | O | |
| $J_{15}$ | — | — | — | S | — | H | $CH_3$ | H | H | — | — | — | — | — | $OCH_3$ | O | |
| $J_{15}$ | — | — | — | S | — | H | $CH_3$ | H | H | — | — | — | — | — | $CH_3$ | O | |
| $J_{15}$ | — | — | — | $SO_2$ | — | H | $CH_3$ | H | H | — | — | — | — | — | $OCH_3$ | O | |
| $J_{15}$ | — | — | — | $SO_2$ | — | H | $CH_3$ | H | H | — | — | — | — | — | $OCH_3$ | $CH_2$ | |
| $J_{16}$ | — | $CH_2$ | — | O | — | H | — | $CH_3$ | H | — | — | — | — | — | $OCH_3$ | $CH_2$ | |
| $J_{16}$ | — | $CH_2$ | — | S | — | H | — | $CH_3$ | H | — | — | — | — | — | $OCH_3$ | O | |
| $J_{16}$ | — | $CH_2$ | — | $SO_2$ | — | H | — | $CH_3$ | H | — | — | — | — | — | $OCH_3$ | O | |
| $J_{16}$ | — | O | — | $SO_2$ | — | H | — | $CH_3$ | H | — | — | — | — | — | $CH_3$ | O | |

TABLE 3-continued

General Formula 3

| J | n | L | Q | $Q_1$ | $Q_2$ | $R_1$ | $R_2$ | $R_3$ | $R_4$ | $R_5$ | $R_6$ | $R_7$ | $R_8$ | $R_9$ | $X_1$ | $Y_1$ | m.p. (°C.) |
|---|---|---|---|---|---|---|---|---|---|---|---|---|---|---|---|---|---|
| $J_{17}$ | — | — | — | — | O | H | — | H | H | — | — | — | — | — | $OCH_3$ | O | |
| $J_{17}$ | — | — | — | — | S | H | — | H | H | — | — | — | — | — | $OCH_3$ | O | |
| $J_{18}$ | — | $CH_2$ | — | — | — | H | — | H | H | — | H | H | — | — | $OCH_3$ | O | |
| $J_{18}$ | — | $CH_2$ | — | — | — | H | — | H | H | — | $CH_3$ | H | — | — | $CH_3$ | O | |
| $J_{19}$ | — | — | — | — | — | H | — | H | H | — | — | — | — | — | $OCH_3$ | O | |
| $J_{19}$ | — | — | — | — | — | H | — | H | H | — | — | — | — | — | $CH_3$ | O | |
| $J_{20}$ | — | $CH_2$ | — | — | — | H | — | — | — | — | — | — | — | — | $CH_3$ | O | |
| $J_{20}$ | — | $CH_2$ | — | — | — | H | — | — | — | — | — | — | — | — | $OCH_3$ | O | |
| $J_{20}$ | — | O | — | — | — | H | — | — | — | — | — | — | — | — | $OCH_3$ | $CH_2$ | |
| $J_{20}$ | — | O | — | — | — | H | — | — | — | — | — | — | — | — | $OCH_3$ | O | |
| $J_{21}$ | — | $CH_2$ | — | — | — | — | — | — | — | — | — | — | Cl | — | $OCH_3$ | O | |
| $J_{21}$ | — | $CH_2$ | — | — | — | — | — | — | — | — | — | — | F | — | $OCH_3$ | O | |
| $J_{21}$ | — | $CH_2$ | — | — | — | — | — | — | — | — | — | — | Br | — | $OCH_3$ | O | |
| $J_{21}$ | — | $CH_2$ | — | — | — | — | — | — | — | — | — | — | $SO_2CH_3$ | — | $OCH_3$ | O | |
| $J_{21}$ | — | $CH_2$ | — | — | — | — | — | — | — | — | — | — | $OSO_2CH_3$ | — | $OCH_3$ | $CH_2$ | |
| $J_{21}$ | — | $CH_2$ | — | — | — | — | — | — | — | — | — | — | $SO_2N(CH_3)_2$ | — | $OCH_3$ | $CH_2$ | |
| $J_{21}$ | — | $CH_2$ | — | — | — | — | — | — | — | — | — | — | $CO_2CH_3$ | — | $OCH_3$ | $CH_2$ | |
| $J_{21}$ | — | O | — | — | — | — | — | — | — | — | — | — | Cl | — | $OCH_3$ | O | |
| $J_{21}$ | — | O | — | — | — | — | — | — | — | — | — | — | F | — | $OCH_3$ | O | |
| $J_{21}$ | — | O | — | — | — | — | — | — | — | — | — | — | Br | — | $OCH_3$ | O | |
| $J_{21}$ | — | O | — | — | — | — | — | — | — | — | — | — | $SO_2CH_3$ | — | $OCH_3$ | O | |
| $J_{21}$ | — | O | — | — | — | — | — | — | — | — | — | — | $OSO_2CH_3$ | — | $OCH_3$ | O | |
| $J_{21}$ | — | O | — | — | — | — | — | — | — | — | — | — | $SO_2N(CH_3)_2$ | — | $OCH_3$ | O | |
| $J_{21}$ | — | O | — | — | — | — | — | — | — | — | — | — | $CO_2CH_3$ | — | $OCH_3$ | O | |

TABLE 4

General Formula 4

| J | n | L | Q | $Q_1$ | $Q_2$ | $R_1$ | $R_2$ | $R_3$ | $R_4$ | $R_5$ | $R_6$ | $R_7$ | $R_8$ | $R_9$ | $X_1$ | m.p. (°C.) |
|---|---|---|---|---|---|---|---|---|---|---|---|---|---|---|---|---|
| $J_1$ | 0 | $CH_2$ | — | — | — | H | — | — | — | — | — | — | — | $CH_3$ | $CH_3$ | |
| $J_1$ | 0 | $CH_2$ | — | — | — | H | — | — | — | — | — | — | — | $CH_3$ | $OCH_3$ | |
| $J_1$ | 0 | CH | — | — | — | H | — | — | — | — | — | — | — | $CH_3$ | $OC_2H_5$ | |
| $J_1$ | 0 | $CH_2$ | — | — | — | H | — | — | — | — | — | — | — | $CH_3$ | $OCF_2H$ | |
| $J_1$ | 0 | O | — | — | — | H | — | — | — | — | — | — | — | $CH_3$ | $CH_3$ | |
| $J_1$ | 0 | O | — | — | — | H | — | — | — | — | — | — | — | $CH_3$ | $OCH_3$ | |
| $J_1$ | 0 | O | — | — | — | H | — | — | — | — | — | — | — | $CH_3$ | $OCF_2H$ | |
| $J_2$ | 0 | $CH_2$ | — | — | — | H | $CH_3$ | — | — | — | — | — | — | — | $CH_3$ | |
| $J_2$ | 0 | $CH_2$ | — | — | — | H | $CH_3$ | — | — | — | — | — | — | — | $OCH_3$ | |
| $J_2$ | 0 | O | — | — | — | H | $CH_3$ | — | — | — | — | — | — | — | $CH_3$ | |
| $J_2$ | 1 | $CH_2$ | — | — | — | H | $CH_3$ | — | — | — | — | — | — | — | $OCH_3$ | |
| $J_2$ | 1 | $CH_2$ | — | — | — | H | $CH_3$ | — | — | — | — | — | — | — | $OC_2H_5$ | |
| $J_2$ | 1 | O | — | — | — | H | $CH_3$ | — | — | — | — | — | — | — | $OCH_3$ | |
| $J_3$ | 0 | $CH_2$ | — | — | — | H | — | H | H | — | — | — | — | — | $OCH_3$ | |
| $J_3$ | 0 | $CH_2$ | — | — | — | H | — | H | H | — | — | — | — | — | $CH_3$ | |
| $J_3$ | 0 | $CH_2$ | — | — | — | H | — | H | H | — | — | — | — | — | $OC_2H_5$ | |
| $J_3$ | 1 | $CH_2$ | — | — | — | H | — | H | H | — | — | — | — | — | $OCH_3$ | |
| $J_3$ | 1 | $CH_2$ | — | — | — | H | — | H | H | — | — | — | — | — | $CH_3$ | |
| $J_3$ | 1 | O | — | — | — | H | — | H | H | — | — | — | — | — | $OCH_3$ | |
| $J_4$ | 0 | $CH_2$ | — | — | — | H | — | — | — | — | — | — | — | — | $OCH_3$ | |
| $J_4$ | 0 | O | — | — | — | H | — | — | — | — | — | — | — | — | $OCH_3$ | |
| $J_4$ | 1 | $CH_2$ | — | — | — | H | — | — | — | — | — | — | — | — | $OCH_3$ | |
| $J_5$ | 0 | — | — | — | — | H | $CH_3$ | — | — | — | — | — | — | — | $CH_3$ | |
| $J_5$ | 0 | — | — | — | — | H | $CH_3$ | — | — | — | — | — | — | — | $OCH_3$ | |
| $J_5$ | 0 | — | — | — | — | H | $CH_3$ | — | — | — | — | — | — | — | $OC_2H_5$ | |
| $J_6$ | 0 | — | — | — | — | H | $CH_3$ | — | — | — | — | — | — | — | $OCF_2H$ | |
| $J_7$ | — | $CH_2$ | — | — | — | H | $CH_3$ | — | — | — | — | — | — | $CH_3$ | $OCH_3$ | |
| $J_7$ | — | $CH_2$ | — | — | — | H | $CH_3$ | — | — | — | — | — | — | $CH_3$ | $CH_3$ | |
| $J_8$ | — | $CH_2$ | — | — | — | H | — | H | — | — | — | — | — | — | $OCH_3$ | |
| $J_8$ | — | O | — | — | — | H | — | H | — | — | — | — | — | — | $OCH_3$ | |
| $J_9$ | — | $CH_2$ | — | — | — | H | — | — | — | — | — | — | — | — | $OCH_3$ | |
| $J_{10}$ | — | — | — | — | — | H | $CH_3$ | — | — | — | — | — | — | — | $OCH_3$ | |
| $J_{10}$ | — | — | — | — | — | H | $CH_3$ | — | — | — | — | — | — | — | $CH_3$ | |
| $J_{11}$ | — | — | — | — | — | H | $CH_3$ | — | — | — | — | — | — | — | $OC_2H_5$ | |
| $J_{12}$ | — | $CH_2$ | — | — | — | H | — | H | — | — | — | — | — | — | $CH_3$ | |
| $J_{12}$ | — | $CH_2$ | — | — | — | H | — | H | — | — | — | — | — | — | $OCH_3$ | |
| $J_{12}$ | — | O | — | — | — | H | — | H | — | — | — | — | — | — | $OCH_3$ | |
| $J_{12}$ | — | O | — | — | — | H | — | H | — | — | — | — | — | — | $OCF_2H$ | |
| $J_{12}$ | — | O | — | — | — | H | — | H | — | — | — | — | — | — | $CH_3$ | |
| $J_{13}$ | — | $CH_2$ | O | — | — | H | — | — | — | — | — | — | — | — | $OCH_3$ | |
| $J_{13}$ | — | O | O | — | — | H | — | — | — | — | — | — | — | — | $OC_2H_5$ | |
| $J_{13}$ | — | $CH_2$ | $CH_2$ | — | — | H | — | — | — | — | — | — | — | — | $CH_3$ | |
| $J_{14}$ | — | $CH_2$ | — | — | — | H | — | — | — | — | — | — | — | — | $OCH_3$ | |
| $J_{14}$ | — | $CH_2$ | — | — | — | H | — | — | — | — | — | — | — | — | $CH_3$ | |
| $J_{14}$ | — | O | — | — | — | H | — | — | — | — | — | — | — | — | $OCH_3$ | |
| $J_{15}$ | — | — | — | O | — | H | — | $CH_3$ | H | H | — | — | — | — | $OCH_3$ | |
| $J_{15}$ | — | — | — | O | — | H | — | $CH_3$ | H | H | — | — | — | — | $CH_3$ | |

TABLE 4-continued

General Formula 4

| J | n | L | Q | $Q_1$ | $Q_2$ | $R_1$ | $R_2$ | $R_3$ | $R_4$ | $R_5$ | $R_6$ | $R_7$ | $R_8$ | $R_9$ | $X_1$ | m.p. (°C.) |
|---|---|---|---|---|---|---|---|---|---|---|---|---|---|---|---|---|
| $J_{15}$ | — | — | — | O | — | H | — | $CH_3$ | H | H | — | — | — | — | $OCHF_2$ | |
| $J_{15}$ | — | — | — | S | — | H | — | $CH_3$ | H | H | — | — | — | — | $CH_3$ | |
| $J_{15}$ | — | — | — | S | — | H | — | $CH_3$ | H | H | — | — | — | — | $OCH_3$ | |
| $J_{15}$ | — | — | — | $SO_2$ | — | H | — | $CH_3$ | H | H | — | — | — | — | $CH_3$ | |
| $J_{15}$ | — | — | — | $SO_2$ | — | H | — | $CH_3$ | H | H | — | — | — | — | $OCH_3$ | |
| $J_{16}$ | — | $CH_2$ | — | O | — | H | — | $CH_3$ | H | — | — | — | — | — | $OCH_3$ | |
| $J_{16}$ | — | $CH_2$ | — | S | — | H | — | $CH_3$ | H | — | — | — | — | — | $OCH_3$ | |
| $J_{16}$ | — | $CH_2$ | — | $SO_2$ | — | H | — | $CH_3$ | H | — | — | — | — | — | $OCH_3$ | |
| $J_{16}$ | — | O | — | $SO_2$ | — | H | — | $CH_3$ | H | — | — | — | — | — | $OCH_3$ | |
| $J_{17}$ | — | — | — | — | O | H | — | H | H | — | — | — | — | — | $OCH_3$ | |
| $J_{17}$ | — | — | — | — | S | H | — | H | H | — | — | — | — | — | $OCH_3$ | |
| $J_{18}$ | — | $CH_2$ | — | — | — | H | — | H | H | — | $CH_3$ | H | — | — | $CH_3$ | |
| $J_{18}$ | — | $CH_2$ | — | — | — | H | — | H | H | — | H | H | — | — | $OCH_3$ | |
| $J_{19}$ | — | — | — | — | — | H | — | H | H | — | — | — | — | — | $OCH_3$ | |
| $J_{19}$ | — | — | — | — | — | H | — | H | H | — | — | — | — | — | $OC_2H_5$ | |
| $J_{20}$ | — | $CH_2$ | — | — | — | H | — | — | — | — | — | — | — | — | $OCH_3$ | |
| $J_{20}$ | — | $CH_2$ | — | — | — | H | — | — | — | — | — | — | — | — | $OC_2H_5$ | |
| $J_{20}$ | — | O | — | — | — | H | — | — | — | — | — | — | — | — | $OCH_3$ | |
| $J_{20}$ | — | O | — | — | — | H | — | — | — | — | — | — | — | — | $OC_2H_5$ | |
| $J_{21}$ | — | $CH_2$ | — | — | — | — | — | — | — | — | — | — | Cl | — | $OCH_3$ | |
| $J_{21}$ | — | $CH_2$ | — | — | — | — | — | — | — | — | — | — | F | — | $OCH_3$ | |
| $J_{21}$ | — | $CH_2$ | — | — | — | — | — | — | — | — | — | — | Br | — | $OCH_3$ | |
| $J_{21}$ | — | $CH_2$ | — | — | — | — | — | — | — | — | — | — | $SO_2CH_3$ | — | $OCH_3$ | |
| $J_{21}$ | — | $CH_2$ | — | — | — | — | — | — | — | — | — | — | $OSO_2CH_3$ | — | $OCH_3$ | |
| $J_{21}$ | — | $CH_2$ | — | — | — | — | — | — | — | — | — | — | $SO_2N(CH_3)_2$ | — | $OCH_3$ | |
| $J_{21}$ | — | $CH_2$ | — | — | — | — | — | — | — | — | — | — | $CO_2CH_3$ | — | $OCH_3$ | |
| $J_{21}$ | — | O | — | — | — | — | — | — | — | — | — | — | Cl | — | $OCH_3$ | |
| $J_{21}$ | — | O | — | — | — | — | — | — | — | — | — | — | F | — | $OCH_3$ | |
| $J_{21}$ | — | O | — | — | — | — | — | — | — | — | — | — | Br | — | $OCH_3$ | |
| $J_{21}$ | — | O | — | — | — | — | — | — | — | — | — | — | $SO_2CH_3$ | — | $OCH_3$ | |
| $J_{21}$ | — | O | — | — | — | — | — | — | — | — | — | — | $OSO_2CH_3$ | — | $OCH_3$ | |
| $J_{21}$ | — | O | — | — | — | — | — | — | — | — | — | — | $SO_2N(CH_3)_2$ | — | $OCH_3$ | |
| $J_{21}$ | — | O | — | — | — | — | — | — | — | — | — | — | $CO_2CH_3$ | — | $OCH_3$ | |

TABLE 5

General Formula 5

| J | n | L | Q | $Q_1$ | $Q_2$ | $R_1$ | $R_2$ | $R_3$ | $R_4$ | $R_5$ | $R_6$ | $R_7$ | $R_8$ | $R_9$ | $X_1$ | $Y_3$ | m.p. (°C.) |
|---|---|---|---|---|---|---|---|---|---|---|---|---|---|---|---|---|---|
| $J_1$ | 0 | $CH_2$ | — | — | — | H | — | — | — | — | — | — | — | $CH_3$ | $OCH_3$ | $CH_3$ | |
| $J_1$ | 0 | $CH_2$ | — | — | — | H | — | — | — | — | — | — | — | $CH_3$ | $OCH_3$ | H | |
| $J_1$ | 0 | $CH_2$ | — | — | — | H | — | — | — | — | — | — | — | $CH_3$ | $CH_3$ | $CH_3$ | |
| $J_1$ | 0 | O | — | — | — | H | — | — | — | — | — | — | — | $CH_3$ | $OCH_3$ | $CH_3$ | |
| $J_1$ | 0 | O | — | — | — | H | — | — | — | — | — | — | — | $CH_3$ | $OCH_3$ | H | |
| $J_1$ | 0 | O | — | — | — | H | — | — | — | — | — | — | — | $CH_3$ | $CH_3$ | $CH_3$ | |
| $J_2$ | 0 | $CH_2$ | — | — | — | H | $CH_3$ | — | — | — | — | — | — | — | $OCH_3$ | H | |
| $J_2$ | 0 | $CH_2$ | — | — | — | H | $CH_3$ | — | — | — | — | — | — | — | $OC_2H_5$ | H | |
| $J_2$ | 0 | $CH_2$ | — | — | — | H | $CH_3$ | — | — | — | — | — | — | — | $CH_3$ | $CH_3$ | |
| $J_2$ | 0 | $CH_2$ | — | — | — | H | $CH_3$ | — | — | — | — | — | — | — | $CH_3$ | H | |
| $J_2$ | 0 | O | — | — | — | H | $CH_3$ | — | — | — | — | — | — | — | $OCH_3$ | H | |
| $J_2$ | 1 | $CH_2$ | — | — | — | H | $CH_3$ | — | — | — | — | — | — | — | $OCH_3$ | H | |
| $J_2$ | 1 | $CH_2$ | — | — | — | H | $CH_3$ | — | — | — | — | — | — | — | $CH_3$ | $CH_3$ | |
| $J_2$ | 1 | O | — | — | — | H | $CH_3$ | — | — | — | — | — | — | — | $OCH_3$ | $CH_3$ | |
| $J_3$ | 0 | $CH_2$ | — | — | — | H | — | H | H | — | — | — | — | — | $OCH_3$ | H | |
| $J_3$ | 0 | $CH_2$ | — | — | — | H | — | H | H | — | — | — | — | — | $CH_3$ | H | |
| $J_3$ | 0 | $CH_2$ | — | — | — | H | — | H | H | — | — | — | — | — | $CH_3$ | $CH_3$ | |
| $J_3$ | 1 | $CH_2$ | — | — | — | H | — | H | H | — | — | — | — | — | $CH_3$ | H | |
| $J_3$ | 1 | $CH_2$ | — | — | — | H | — | H | H | — | — | — | — | — | $OCH_3$ | H | |
| $J_3$ | 1 | O | — | — | — | H | — | H | H | — | — | — | — | — | $CH_3$ | H | |
| $J_4$ | 0 | $CH_2$ | — | — | — | H | — | — | — | — | — | — | — | — | $OCH_3$ | H | |
| $J_4$ | 0 | O | — | — | — | H | — | — | — | — | — | — | — | — | $OCH_3$ | $CH_3$ | |
| $J_4$ | 1 | $CH_2$ | — | — | — | H | — | — | — | — | — | — | — | — | $OCH_3$ | H | |
| $J_5$ | 0 | — | — | — | — | H | $CH_3$ | — | — | — | — | — | — | — | $OCH_3$ | H | |
| $J_5$ | 0 | — | — | — | — | H | $CH_3$ | — | — | — | — | — | — | — | $OC_2H_5$ | $CH_3$ | |
| $J_6$ | 0 | — | — | — | — | H | $CH_3$ | — | — | — | — | — | — | — | $OCH_3$ | H | |
| $J_7$ | — | $CH_2$ | — | — | — | H | $CH_3$ | — | — | — | — | — | — | $CH_3$ | $OCH_3$ | $CH_3$ | |
| $J_7$ | — | $CH_2$ | — | — | — | H | $CH_3$ | — | — | — | — | — | — | $CH_3$ | $OCH_3$ | H | |
| $J_8$ | — | $CH_2$ | — | — | — | H | — | H | — | — | — | — | — | — | $OCH_3$ | H | |
| $J_8$ | — | O | — | — | — | H | — | H | — | — | — | — | — | — | $OCH_3$ | $CH_3$ | |
| $J_9$ | — | $CH_2$ | — | — | — | H | — | — | — | — | — | — | — | — | $OCH_3$ | $CH_3$ | |
| $J_{10}$ | — | — | — | — | — | H | $CH_3$ | — | — | — | — | — | — | — | $OCH_3$ | H | |
| $J_{10}$ | — | — | — | — | — | H | $CH_3$ | — | — | — | — | — | — | — | $CH_3$ | H | |
| $J_{11}$ | — | — | — | — | — | H | $CH_3$ | — | — | — | — | — | — | — | $OCH_3$ | H | |
| $J_{12}$ | — | $CH_2$ | — | — | — | H | — | H | — | — | — | — | — | — | $OCH_3$ | H | |
| $J_{12}$ | — | $CH_2$ | — | — | — | H | — | H | — | — | — | — | — | — | $CH_3$ | H | |
| $J_{12}$ | — | O | — | — | — | H | — | H | — | — | — | — | — | — | $OCH_3$ | H | |
| $J_{12}$ | — | O | — | — | — | H | — | H | — | — | — | — | — | — | $CH_3$ | H | |

TABLE 5-continued

General Formula 5

| J | n | L | Q | $Q_1$ | $Q_2$ | $R_1$ | $R_2$ | $R_3$ | $R_4$ | $R_5$ | $R_6$ | $R_7$ | $R_8$ | $R_9$ | $X_1$ | $Y_3$ | m.p. (°C.) |
|---|---|---|---|---|---|---|---|---|---|---|---|---|---|---|---|---|---|
| $J_{13}$ | — | $CH_2$ | O | — | — | H | — | — | — | — | — | — | — | — | $OCH_3$ | H | |
| $J_{13}$ | — | O | O | — | — | H | — | — | — | — | — | — | — | — | $OCH_3$ | H | |
| $J_{13}$ | — | $CH_2$ | $CH_2$ | — | — | H | — | — | — | — | — | — | — | — | $OCH_3$ | H | |
| $J_{14}$ | — | $CH_2$ | — | — | — | H | — | — | — | — | — | — | — | — | $OCH_3$ | H | |
| $J_{14}$ | — | $CH_2$ | — | — | — | H | — | — | — | — | — | — | — | — | $CH_3$ | H | |
| $J_{14}$ | — | O | — | — | — | H | — | — | — | — | — | — | — | — | $CH_3$ | $CH_3$ | |
| $J_{15}$ | — | — | — | O | — | H | — | $CH_3$ | H | H | — | — | — | — | $OCH_3$ | $CH_3$ | |
| $J_{15}$ | — | — | — | O | — | H | — | $CH_3$ | H | H | — | — | — | — | $OCH_3$ | H | |
| $J_{15}$ | — | — | — | S | — | H | — | $CH_3$ | H | H | — | — | — | — | $OCH_3$ | H | |
| $J_{15}$ | — | — | — | S | — | H | — | $CH_3$ | H | H | — | — | — | — | $OCH_3$ | $CH_3$ | |
| $J_{15}$ | — | — | — | $SO_2$ | — | H | — | $CH_3$ | H | H | — | — | — | — | $OCH_3$ | H | |
| $J_{15}$ | — | — | — | $SO_2$ | — | H | — | $CH_3$ | H | H | — | — | — | — | $OCH_3$ | $CH_3$ | |
| $J_{16}$ | — | $CH_2$ | — | O | — | H | — | $CH_3$ | H | — | — | — | — | — | $OCH_3$ | H | |
| $J_{16}$ | — | $CH_2$ | — | S | — | H | — | $CH_3$ | H | — | — | — | — | — | $OCH_3$ | H | |
| $J_{16}$ | — | $CH_2$ | — | $SO_2$ | — | H | — | $CH_3$ | H | — | — | — | — | — | $OCH_3$ | H | |
| $J_{16}$ | — | O | — | $SO_2$ | — | H | — | $CH_3$ | H | — | — | — | — | — | $OCH_3$ | H | |
| $J_{17}$ | — | — | — | — | O | H | — | H | H | — | — | — | — | — | $OCH_3$ | $CH_3$ | |
| $J_{17}$ | — | — | — | — | S | H | — | H | H | — | — | — | — | — | $CH_3$ | H | |
| $J_{18}$ | — | $CH_2$ | — | — | — | H | — | H | H | — | H | H | — | — | $OCH_3$ | H | |
| $J_{18}$ | — | $CH_2$ | — | — | — | H | — | H | H | — | $CH_3$ | H | — | — | $OCH_3$ | H | |
| $J_{19}$ | — | — | — | — | — | H | — | H | H | — | — | — | — | — | $OCH_3$ | H | |
| $J_{19}$ | — | — | — | — | — | H | — | H | H | — | — | — | — | — | $OCH_3$ | H | |
| $J_{20}$ | — | $CH_2$ | — | — | — | H | — | — | — | — | — | — | — | — | $OCH_3$ | H | |
| $J_{20}$ | — | $CH_2$ | — | — | — | H | — | — | — | — | — | — | — | — | $OCH_3$ | $CH_3$ | |
| $J_{20}$ | — | O | — | — | — | H | — | — | — | — | — | — | — | — | $OCH_3$ | H | |
| $J_{20}$ | — | O | — | — | — | H | — | — | — | — | — | — | — | — | $OCH_3$ | $CH_3$ | |
| $J_{21}$ | — | $CH_2$ | — | — | — | — | — | — | — | — | — | — | Cl | — | $CH_3$ | H | |
| $J_{21}$ | — | $CH_2$ | — | — | — | — | — | — | — | — | — | — | F | — | $OCH_3$ | H | |
| $J_{21}$ | — | $CH_2$ | — | — | — | — | — | — | — | — | — | — | Br | — | $OCH_3$ | H | |
| $J_{21}$ | — | $CH_2$ | — | — | — | — | — | — | — | — | — | — | $SO_2CH_3$ | — | $OCH_3$ | H | |
| $J_{21}$ | — | $CH_2$ | — | — | — | — | — | — | — | — | — | — | $OSO_2CH_3$ | — | $OCH_3$ | H | |
| $J_{21}$ | — | $CH_2$ | — | — | — | — | — | — | — | — | — | — | $SO_2N(CH_3)_2$ | — | $OCH_3$ | H | |
| $J_{21}$ | — | $CH_2$ | — | — | — | — | — | — | — | — | — | — | $CO_2CH_3$ | — | $OCH_3$ | H | |
| $J_{21}$ | — | O | — | — | — | — | — | — | — | — | — | — | Cl | — | $OCH_3$ | H | |
| $J_{21}$ | — | O | — | — | — | — | — | — | — | — | — | — | F | — | $OCH_3$ | H | |
| $J_{21}$ | — | O | — | — | — | — | — | — | — | — | — | — | Br | — | $OCH_3$ | H | |
| $J_{21}$ | — | O | — | — | — | — | — | — | — | — | — | — | $SO_2CH_3$ | — | $OCH_3$ | H | |
| $J_{21}$ | — | O | — | — | — | — | — | — | — | — | — | — | $OSO_2CH_3$ | — | $OCH_3$ | H | |
| $J_{21}$ | — | O | — | — | — | — | — | — | — | — | — | — | $SO_2N(CH_3)_2$ | — | $OCH_3$ | H | |
| $J_{21}$ | — | O | — | — | — | — | — | — | — | — | — | — | $CO_2CH_3$ | — | $OCH_3$ | H | |

TABLE 6

General Formula 6

| J | n | L | Q | $Q_1$ | $Q_2$ | $R_1$ | $R_2$ | $R_3$ | $R_4$ | $R_5$ | $R_6$ | $R_7$ | $R_8$ | $R_9$ | $X_2$ | $Y_2$ | m.p. (°C.) |
|---|---|---|---|---|---|---|---|---|---|---|---|---|---|---|---|---|---|
| $J_1$ | 0 | $CH_2$ | — | — | — | H | — | — | — | — | — | — | — | $CH_3$ | $CH_3$ | $OCH_3$ | |
| $J_1$ | 0 | $CH_2$ | — | — | — | H | — | — | — | — | — | — | — | $CH_3$ | $C_2H_5$ | $OC_2H_5$ | |
| $J_1$ | 0 | $CH_2$ | — | — | — | H | — | — | — | — | — | — | — | $CH_3$ | $CH_2CF_3$ | $SCH_3$ | |
| $J_1$ | 0 | $CH_2$ | — | — | — | H | — | — | — | — | — | — | — | $CH_3$ | $CH_3$ | $SC_2H_5$ | |
| $J_1$ | 0 | $CH_2$ | — | — | — | H | — | — | — | — | — | — | — | $CH_3$ | $C_2H_5$ | $OCF_2H$ | |
| $J_1$ | 0 | $CH_2$ | — | — | — | H | — | — | — | — | — | — | — | $CH_3$ | $C_2H_5$ | $SCF_2H$ | |
| $J_1$ | 0 | O | — | — | — | H | — | — | — | — | — | — | — | $CH_3$ | $C_2H_5$ | $OCH_3$ | |
| $J_1$ | 0 | O | — | — | — | H | — | — | — | — | — | — | — | $CH_3$ | $C_2H_5$ | $SCH_3$ | |
| $J_1$ | 0 | O | — | — | — | H | — | — | — | — | — | — | — | $CH_3$ | $C_2H_5$ | $SCF_2H$ | |
| $J_2$ | 0 | $CH_2$ | — | — | — | H | $CH_3$ | — | — | — | — | — | — | — | $CH_2CF_3$ | $SCH_3$ | |
| $J_2$ | 0 | $CH_2$ | — | — | — | H | $CH_3$ | — | — | — | — | — | — | — | $CH_2CH_3$ | $SC_2H_5$ | |
| $J_2$ | 0 | O | — | — | — | H | $CH_3$ | — | — | — | — | — | — | — | $CH_2CH_3$ | $SCH_3$ | |
| $J_2$ | 1 | $CH_2$ | — | — | — | H | $CH_3$ | — | — | — | — | — | — | — | $CH_2CH_3$ | $SCH_3$ | |
| $J_2$ | 1 | $CH_2$ | — | — | — | H | $CH_3$ | — | — | — | — | — | — | — | $CH_2CF_3$ | $SC_2H_5$ | |
| $J_2$ | 1 | O | — | — | — | H | $CH_3$ | — | — | — | — | — | — | — | $C_2H_5$ | $SCH_3$ | |
| $J_3$ | 0 | $CH_2$ | — | — | — | H | — | H | H | — | — | — | — | — | $CH_3$ | $SC_2H_5$ | |
| $J_3$ | 0 | $CH_2$ | — | — | — | H | — | H | H | — | — | — | — | — | $CH_3$ | $SCH_3$ | |
| $J_3$ | 1 | $CH_2$ | — | — | — | H | — | H | H | — | — | — | — | — | $CH_3$ | $SCH_3$ | |
| $J_3$ | 1 | $CH_2$ | — | — | — | H | — | H | H | — | — | — | — | — | $CH_3$ | $SC_2H_5$ | |
| $J_3$ | 1 | O | — | — | — | H | — | H | H | — | — | — | — | — | $CH_3$ | $SC_2H_5$ | |
| $J_4$ | 0 | $CH_2$ | — | — | — | H | — | — | — | — | — | — | — | — | $CH_3$ | $SCH_3$ | |
| $J_4$ | 0 | O | — | — | — | H | — | — | — | — | — | — | — | — | $C_2H_5$ | $SCH_3$ | |
| $J_4$ | 1 | $CH_2$ | — | — | — | H | — | — | — | — | — | — | — | — | $CH_3$ | $SCH_3$ | |
| $J_5$ | 0 | — | — | — | — | H | $CH_3$ | — | — | — | — | — | — | — | $CH_3$ | $SCH_3$ | |
| $J_5$ | 0 | — | — | — | — | H | $CH_3$ | — | — | — | — | — | — | — | $C_2H_5$ | $SCH_3$ | |
| $J_5$ | 0 | — | — | — | — | H | $CH_3$ | — | — | — | — | — | — | — | $CH_2CF_3$ | $SCH_3$ | |
| $J_6$ | 0 | — | — | — | — | H | $CH_3$ | — | — | — | — | — | — | — | $CH_3$ | $SCH_3$ | |
| $J_7$ | — | $CH_2$ | — | — | — | H | $CH_3$ | — | — | — | — | — | — | $CH_3$ | $CH_2CH_3$ | $SC_2H_5$ | |
| $J_7$ | — | $CH_2$ | — | — | — | H | $CH_3$ | — | — | — | — | — | — | $CH_3$ | $CH_3$ | $SC_2H_5$ | |
| $J_8$ | — | $CH_2$ | — | — | — | H | — | H | — | — | — | — | — | — | $CH_3$ | $SCH_3$ | |
| $J_8$ | — | O | — | — | — | H | — | H | — | — | — | — | — | — | $CH_3$ | $SCH_3$ | |

TABLE 6-continued

General Formula 6

| J | n | L | Q | $Q_1$ | $Q_2$ | $R_1$ | $R_2$ | $R_3$ | $R_4$ | $R_5$ | $R_6$ | $R_7$ | $R_8$ | $R_9$ | $X_2$ | $Y_2$ | m.p. (°C.) |
|---|---|---|---|---|---|---|---|---|---|---|---|---|---|---|---|---|---|
| $J_9$ | — | $CH_2$ | — | — | — | H | — | — | — | — | — | — | — | — | $CH_3$ | $SCH_3$ | |
| $J_{10}$ | — | — | — | — | — | H | $CH_3$ | — | — | — | — | — | — | — | $CH_3$ | $SCH_3$ | |
| $J_{10}$ | — | — | — | — | — | H | $CH_3$ | — | — | — | — | — | — | — | $C_2H_5$ | $SC_2H_5$ | |
| $J_{11}$ | — | — | — | — | — | H | $CH_3$ | — | — | — | — | — | — | — | $CH_3$ | $SCH_3$ | |
| $J_{12}$ | — | $CH_2$ | — | — | — | H | — | H | — | — | — | — | — | — | $C_2H_5$ | $SCH_3$ | |
| $J_{12}$ | — | $CH_2$ | — | — | — | H | — | H | — | — | — | — | — | — | $CH_3$ | $SCH_3$ | |
| $J_{12}$ | — | O | — | — | — | H | — | H | — | — | — | — | — | — | $CH_3$ | $SC_2H_5$ | |
| $J_{12}$ | — | O | — | — | — | H | — | H | — | — | — | — | — | — | $C_2H_5$ | $SCH_3$ | |
| $J_{13}$ | — | $CH_2$ | O | — | — | H | — | — | — | — | — | — | — | — | $CH_3$ | $SCH_3$ | |
| $J_{13}$ | — | O | O | — | — | H | — | — | — | — | — | — | — | — | $CH_3$ | $SCH_3$ | |
| $J_{13}$ | — | $CH_2$ | $CH_2$ | — | — | H | — | — | — | — | — | — | — | — | $CH_3$ | $SC_2H_5$ | |
| $J_{14}$ | — | $CH_2$ | — | — | — | H | — | — | — | — | — | — | — | — | $CH_3$ | $SCH_3$ | |
| $J_{14}$ | — | $CH_2$ | — | — | — | H | — | — | — | — | — | — | — | — | $CH_3$ | $SC_2H_5$ | |
| $J_{14}$ | — | O | — | — | — | H | — | — | — | — | — | — | — | — | $CH_3$ | $SCH_3$ | |
| $J_{15}$ | — | — | — | O | — | H | — | $CH_3$ | H | H | — | — | — | — | $CH_3$ | $SCH_3$ | |
| $J_{15}$ | — | — | — | O | — | H | — | $CH_3$ | H | H | — | — | — | — | $CH_3$ | $SC_2H_5$ | |
| $J_{15}$ | — | — | — | O | — | H | — | $CH_3$ | H | H | — | — | — | — | $C_2H_5$ | $SCH_3$ | |
| $J_{15}$ | — | — | — | S | — | H | — | $CH_3$ | H | H | — | — | — | — | $CH_3$ | $SCH_3$ | |
| $J_{15}$ | — | — | — | S | — | H | — | $CH_3$ | H | H | — | — | — | — | $CH_3$ | $SC_2H_5$ | |
| $J_{15}$ | — | — | — | $SO_2$ | — | H | — | $CH_3$ | H | H | — | — | — | — | $CH_3$ | $SCH_3$ | |
| $J_{15}$ | — | — | — | $SO_2$ | — | H | — | $CH_3$ | H | H | — | — | — | — | $CH_3$ | $SC_2H_5$ | |
| $J_{16}$ | — | $CH_2$ | — | O | — | H | — | $CH_3$ | H | — | — | — | — | — | $C_2H_5$ | $SCH_3$ | |
| $J_{16}$ | — | $CH_2$ | — | S | — | H | — | $CH_3$ | H | — | — | — | — | — | $CH_3$ | $SCH_3$ | |
| $J_{16}$ | — | $CH_2$ | — | $SO_2$ | — | H | — | $CH_3$ | H | — | — | — | — | — | $CH_3$ | $SCH_3$ | |
| $J_{16}$ | — | O | — | $SO_2$ | — | H | — | $CH_3$ | H | — | — | — | — | — | $CH_3$ | $SCH_3$ | |
| $J_{17}$ | — | — | — | — | O | H | — | H | H | — | — | — | — | — | $CH_3$ | $SCH_3$ | |
| $J_{17}$ | — | — | — | — | S | H | — | H | H | — | — | — | — | — | $CH_3$ | $SCH_3$ | |
| $J_{18}$ | — | $CH_2$ | — | — | — | H | — | H | H | — | H | H | — | — | $CH_3$ | $SCH_3$ | |
| $J_{18}$ | — | $CH_2$ | — | — | — | H | — | H | H | — | $CH_3$ | H | — | — | $CH_3$ | $SCH_3$ | |
| $J_{19}$ | — | — | — | — | — | H | — | H | H | — | — | — | — | — | $CH_3$ | $SCH_3$ | |
| $J_{19}$ | — | — | — | — | — | H | H | — | H | — | — | — | — | — | $CH_3$ | $SC_2H_5$ | |
| $J_{20}$ | — | $CH_2$ | — | — | — | H | — | — | — | — | — | — | — | — | $CH_3$ | $SCH_3$ | |
| $J_{20}$ | — | $CH_2$ | — | — | — | H | — | — | — | — | — | — | — | — | $CH_3$ | $SC_2H_5$ | |
| $J_{20}$ | — | O | — | — | — | H | — | — | — | — | — | — | — | — | $CH_3$ | $SCH_3$ | |
| $J_{20}$ | — | O | — | — | — | H | — | — | — | — | — | — | — | — | $C_2H_5$ | $SCH_3$ | |
| $J_{21}$ | — | $CH_2$ | — | — | — | — | — | — | — | — | — | — | Cl | — | $CH_3$ | $SCH_3$ | |
| $J_{21}$ | — | $CH_2$ | — | — | — | — | — | — | — | — | — | — | F | — | $CH_3$ | $SCH_3$ | |
| $J_{21}$ | — | $CH_2$ | — | — | — | — | — | — | — | — | — | — | Br | — | $CH_3$ | $SCH_3$ | |
| $J_{21}$ | — | $CH_2$ | — | — | — | — | — | — | — | — | — | — | $SO_2CH_3$ | — | $CH_3$ | $SCH_3$ | |
| $J_{21}$ | — | $CH_2$ | — | — | — | — | — | — | — | — | — | — | $OSO_2CH_3$ | — | $CH_3$ | $SCH_3$ | |
| $J_{21}$ | — | $CH_2$ | — | — | — | — | — | — | — | — | — | — | $SO_2N(CH_3)_2$ | — | $CH_3$ | $SCH_3$ | |
| $J_{21}$ | — | $CH_2$ | — | — | — | — | — | — | — | — | — | — | $CO_2CH_3$ | — | $CH_3$ | $SCH_3$ | |
| $J_{21}$ | — | O | — | — | — | — | — | — | — | — | — | — | Cl | — | $CH_3$ | $SCH_3$ | |
| $J_{21}$ | — | O | — | — | — | — | — | — | — | — | — | — | F | — | $CH_3$ | $SCH_3$ | |
| $J_{21}$ | — | O | — | — | — | — | — | — | — | — | — | — | Br | — | $CH_3$ | $SCH_3$ | |
| $J_{21}$ | — | O | — | — | — | — | — | — | — | — | — | — | $SO_2CH_3$ | — | $CH_3$ | $SCH_3$ | |
| $J_{21}$ | — | O | — | — | — | — | — | — | — | — | — | — | $OSO_2CH_3$ | — | $CH_3$ | $SCH_3$ | |
| $J_{21}$ | — | O | — | — | — | — | — | — | — | — | — | — | $SO_2N(CH_3)_2$ | — | $CH_3$ | $SCH_3$ | |
| $J_{21}$ | — | O | — | — | — | — | — | — | — | — | — | — | $CO_2CH_3$ | — | $CH_3$ | $SCH_3$ | |

TABLE 7

General Formula 7

| J | n | L | Q | $Q_1$ | $Q_2$ | $R_1$ | $R_2$ | $R_3$ | $R_4$ | $R_5$ | $R_6$ | $R_7$ | $R_8$ | $R_9$ | $X_3$ | m.p. (°C.) |
|---|---|---|---|---|---|---|---|---|---|---|---|---|---|---|---|---|
| $J_1$ | 0 | $CH_2$ | — | — | — | H | — | — | — | — | — | — | — | $CH_3$ | $OCH_3$ | |
| $J_1$ | 0 | $CH_2$ | — | — | — | H | — | — | — | — | — | — | — | $CH_3$ | $CH_3$ | |
| $J_1$ | 0 | O | — | — | — | H | — | — | — | — | — | — | — | $CH_3$ | $CH_3$ | |
| $J_1$ | 0 | O | — | — | — | H | — | — | — | — | — | — | — | $CH_3$ | $OCH_3$ | |
| $J_2$ | 0 | $CH_2$ | — | — | — | H | $CH_3$ | — | — | — | — | — | — | — | $OCH_3$ | |
| $J_2$ | 0 | $CH_2$ | — | — | — | H | $CH_3$ | — | — | — | — | — | — | — | $CH_3$ | |
| $J_2$ | 0 | O | — | — | — | H | $CH_3$ | — | — | — | — | — | — | — | $CH_3$ | |
| $J_2$ | 1 | $CH_2$ | — | — | — | H | $CH_3$ | — | — | — | — | — | — | — | $OCH_3$ | |
| $J_2$ | 1 | $CH_2$ | — | — | — | H | $CH_3$ | — | — | — | — | — | — | — | $CH_3$ | |
| $J_2$ | 1 | O | — | — | — | H | $CH_3$ | — | — | — | — | — | — | — | $OCH_3$ | |
| $J_3$ | 0 | $CH_2$ | — | — | — | H | — | H | H | — | — | — | — | — | $CH_3$ | |
| $J_3$ | 0 | $CH_2$ | — | — | — | H | — | H | H | — | — | — | — | — | $OCH_3$ | |
| $J_3$ | 1 | $CH_2$ | — | — | — | H | — | H | H | — | — | — | — | — | $OCH_3$ | |
| $J_3$ | 1 | O | — | — | — | H | — | H | H | — | — | — | — | — | $OCH_3$ | |
| $J_4$ | 0 | $CH_2$ | — | — | — | H | — | — | — | — | — | — | — | — | $CH_3$ | |
| $J_4$ | 0 | O | — | — | — | H | — | — | — | — | — | — | — | — | $OCH_3$ | |
| $J_4$ | 1 | $CH_2$ | — | — | — | H | — | — | — | — | — | — | — | — | $OCH_3$ | |
| $J_5$ | 0 | — | — | — | — | H | $CH_3$ | — | — | — | — | — | — | — | $CH_3$ | |
| $J_5$ | 0 | — | — | — | — | H | $CH_3$ | — | — | — | — | — | — | — | $OCH_3$ | |
| $J_6$ | 0 | — | — | — | — | H | $CH_3$ | — | — | — | — | — | — | — | $OCH_3$ | |
| $J_7$ | — | $CH_2$ | — | — | — | H | $CH_3$ | — | — | — | — | — | — | $CH_3$ | $CH_3$ | |
| $J_7$ | — | $CH_2$ | — | — | — | H | $CH_3$ | — | — | — | — | — | — | $CH_3$ | $OCH_3$ | |

TABLE 7-continued

General Formula 7

| J | n | L | Q | $Q_1$ | $Q_2$ | $R_1$ | $R_2$ | $R_3$ | $R_4$ | $R_5$ | $R_6$ | $R_7$ | $R_8$ | $R_9$ | $X_3$ | m.p. (°C.) |
|---|---|---|---|---|---|---|---|---|---|---|---|---|---|---|---|---|
| $J_8$ | — | $CH_2$ | — | — | — | H | — | H | — | — | — | — | — | — | $CH_3$ | |
| $J_8$ | — | O | — | — | — | H | — | H | — | — | — | — | — | — | $OCH_3$ | |
| $J_9$ | — | $CH_2$ | — | — | — | H | — | — | — | — | — | — | — | — | $CH_3$ | |
| $J_{10}$ | — | — | — | — | — | H | $CH_3$ | — | — | — | — | — | — | — | $CH_3$ | |
| $J_{10}$ | — | — | — | — | — | H | $CH_3$ | — | — | — | — | — | — | — | $OCH_3$ | |
| $J_{11}$ | — | — | — | — | — | H | $CH_3$ | — | — | — | — | — | — | — | $CH_3$ | |
| $J_{12}$ | — | $CH_2$ | — | — | — | H | — | H | — | — | — | — | — | — | $OCH_3$ | |
| $J_{12}$ | — | $CH_2$ | — | — | — | H | — | H | — | — | — | — | — | — | $CH_3$ | |
| $J_{12}$ | — | O | — | — | — | H | — | H | — | — | — | — | — | — | $OCH_3$ | |
| $J_{12}$ | — | O | — | — | — | H | — | H | — | — | — | — | — | — | $CH_3$ | |
| $J_{13}$ | — | $CH_2$ | O | — | — | H | — | — | — | — | — | — | — | — | $CH_3$ | |
| $J_{13}$ | — | O | O | — | — | H | — | — | — | — | — | — | — | — | $OCH_3$ | |
| $J_{13}$ | — | $CH_2$ | $CH_2$ | — | — | H | — | — | — | — | — | — | — | — | $OCH_3$ | |
| $J_{14}$ | — | $CH_2$ | — | — | — | H | — | — | — | — | — | — | — | — | $CH_3$ | |
| $J_{14}$ | — | $CH_2$ | — | — | — | H | — | — | — | — | — | — | — | — | $OCH_3$ | |
| $J_{14}$ | — | O | — | — | — | H | — | — | — | — | — | — | — | — | $OCH_3$ | |
| $J_{15}$ | — | — | — | O | — | H | — | $CH_3$ | H | H | — | — | — | — | $OCH_3$ | |
| $J_{15}$ | — | — | — | O | — | H | — | $CH_3$ | H | H | — | — | — | — | $CH_3$ | |
| $J_{15}$ | — | — | — | S | — | H | — | $CH_3$ | H | H | — | — | — | — | $CH_3$ | |
| $J_{15}$ | — | — | — | S | — | H | — | $CH_3$ | H | H | — | — | — | — | $OCH_3$ | |
| $J_{15}$ | — | — | — | $SO_2$ | — | H | — | $CH_3$ | H | H | — | — | — | — | $CH_3$ | |
| $J_{15}$ | — | — | — | $SO_2$ | — | H | — | $CH_3$ | H | H | — | — | — | — | $OCH_3$ | |
| $J_{16}$ | — | $CH_2$ | — | O | — | H | — | $CH_3$ | H | — | — | — | — | — | $CH_3$ | |
| $J_{16}$ | — | $CH_2$ | — | S | — | H | — | $CH_3$ | H | — | — | — | — | — | $OCH_3$ | |
| $J_{16}$ | — | $CH_2$ | — | $SO_2$ | — | H | — | $CH_3$ | H | — | — | — | — | — | $CH_3$ | |
| $J_{16}$ | — | O | — | $SO_2$ | — | H | — | $CH_3$ | H | — | — | — | — | — | $OCH_3$ | |
| $J_{17}$ | — | — | — | — | O | H | — | H | H | — | — | — | — | — | $CH_3$ | |
| $J_{17}$ | — | — | — | — | S | H | — | H | H | — | — | — | — | — | $CH_3$ | |
| $J_{18}$ | — | $CH_2$ | — | — | — | H | — | H | H | — | H | H | — | — | $OCH_3$ | |
| $J_{18}$ | — | $CH_2$ | — | — | — | H | — | H | H | — | $CH_3$ | H | — | — | $CH_3$ | |
| $J_{19}$ | — | — | — | — | — | H | — | H | H | — | — | — | — | — | $OCH_3$ | |
| $J_{19}$ | — | — | — | — | — | H | — | H | H | — | — | — | — | — | $CH_3$ | |
| $J_{20}$ | — | $CH_2$ | — | — | — | H | — | — | — | — | — | — | — | — | $OCH_3$ | |
| $J_{20}$ | — | $CH_2$ | — | — | — | H | — | — | — | — | — | — | — | — | $CH_3$ | |
| $J_{20}$ | — | O | — | — | — | H | — | — | — | — | — | — | — | — | $OCH_3$ | |
| $J_{20}$ | — | O | — | — | — | H | — | — | — | — | — | — | — | — | $CH_3$ | |
| $J_{21}$ | — | $CH_2$ | — | — | — | — | — | — | — | — | — | — | Cl | — | $OCH_3$ | |
| $J_{21}$ | — | $CH_2$ | — | — | — | — | — | — | — | — | — | — | F | — | $OCH_3$ | |
| $J_{21}$ | — | $CH_2$ | — | — | — | — | — | — | — | — | — | — | Br | — | $OCH_3$ | |
| $J_{21}$ | — | $CH_2$ | — | — | — | — | — | — | — | — | — | — | $SO_2CH_3$ | — | $OCH_3$ | |
| $J_{21}$ | — | $CH_2$ | — | — | — | — | — | — | — | — | — | — | $OSO_2CH_3$ | — | $OCH_3$ | |
| $J_{21}$ | — | $CH_2$ | — | — | — | — | — | — | — | — | — | — | $SO_2N(CH_3)_2$ | — | $OCH_3$ | |
| $J_{21}$ | — | $CH_2$ | — | — | — | — | — | — | — | — | — | — | $CO_2CH_3$ | — | $OCH_3$ | |
| $J_{21}$ | — | O | — | — | — | — | — | — | — | — | — | — | Cl | — | $OCH_3$ | |
| $J_{21}$ | — | O | — | — | — | — | — | — | — | — | — | — | F | — | $OCH_3$ | |
| $J_{21}$ | — | O | — | — | — | — | — | — | — | — | — | — | Br | — | $OCH_3$ | |
| $J_{21}$ | — | O | — | — | — | — | — | — | — | — | — | — | $SO_2CH_3$ | — | $OCH_3$ | |
| $J_{21}$ | — | O | — | — | — | — | — | — | — | — | — | — | $OSO_2CH_3$ | — | $OCH_3$ | |
| $J_{21}$ | — | O | — | — | — | — | — | — | — | — | — | — | $SO_2N(CH_3)_2$ | — | $OCH_3$ | |
| $J_{21}$ | — | O | — | — | — | — | — | — | — | — | — | — | $CO_2CH_3$ | — | $OCH_3$ | |

Formulations

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few liters to several hundred liters per hectare. High strength compositions are primarily used as intermediates for further formulation. The formulation, broadly, contain about 0.1% to 99% by weight of active ingredient(s) and at least one of (a) about 0.1% to 20% surfactant(s) and (b) about 1% to 99.9% solid or liquid inert diluent(s). More specifically, they will contain these ingredients in the following approximate proportions:

TABLE 8

| | Weight Percent* | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions, (including Emulsifiable Concentrates) | 3–50 | 40–95 | 0–15 |
| Aqueous Suspension | 10–50 | 40–84 | 1–20 |
| Dusts | 1–25 | 70–99 | 0–5 |
| Granules and Pellets | 0.1–95 | 5–99.9 | 0–15 |
| High Strength Compositions | 90–99 | 0–10 | 0–2 |

*Active ingredient plus at least one of a Surfactant or a Diluent equals 100 weight percent.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, New Jersey, but other solids, either mined or manufactured, may be used. The more absorptive diluents are preferred for wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual". MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foaming, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering,* Dec. 4, 1967, pp. 147ff. and "Perry's Chemical Engineer's Handbook", 5th Ed., McGraw-Hill, New York, 1973, pp. 8–57ff.

For further information regarding the art of formulation, see for example:

- H. M. Loux, U.S. Pat. No. 3,235,361, Feb. 15, 1966, Col. 6, line 16 through Col. 7, line 19 and Examples 10 through 41;
- R. W. Luckenbaugh, U.S. Pat. No. 3,309,192, Mar. 14, 1967, Col. 5, line 43 through Col. 7, line 62 and Examples 8, 12, 15, 39, 41, 52, 53, 58, 132, 138–140, 162–164, 166, 167 and 169–182;
- H. Gysin and E. Knusli, U.S. Pat. No. 2,891,855, June 23, 1959, Col. 3, line 66 through Col. 5, line 17 and Examples 1–4;
- G. C. Klingman, "Weed Control as a Science", John Wiley and Sons, Inc., New York, 1961, pp. 81–96; and
- J. D. Fryer and S. A. Evans, "Weed Control Handbook", 5th Ed., Blackwell Scientific Publications, Oxford, 1968, pp. 101–103.

In the following examples, all parts are by weight unless otherwise indicated.

EXAMPLE 9

| Wettable Powder | |
|---|---|
| N—[(4-methoxy-6-methyl-1,3,5-triazin-2-yl)aminocarbonyl]-2-methyl-benzo[B]thiophene-7-methanesulfonamide-1,1-dioxide | 80% |
| sodium alkylnaphthalenesulfonate | 2% |
| sodium ligninsulfonate | 2% |
| synthetic amorphous silica | 3% |
| kaolinite | 13% |

The ingredients are blended, hammer-milled until all the solids are essentially under 50 microns, reblended, and packaged.

EXAMPLE 10

| Wettable Powder | |
|---|---|
| N—[(4,6-dimethoxypyrimidin-2-yl)aminocarbonyl]-2,3-dihydro-2-methyl-benzo[B]thiophene-7-methanesulfonamide-1,1-dioxide | 50% |
| sodium alkylnaphthalenesulfonate | 2% |
| low viscosity methyl cellulose | 2% |
| diatomaceous earth | 46% |

The ingredients are blended, coarsely hammer-milled and then air-milled to produce particles essentially all below 10 microns in diameter. The product is reblended before packaging.

EXAMPLE 11

| Granule | |
|---|---|
| Wettable Powder of Example 10 | 5% |
| attapulgite granules (U.S.S. 20–40 mesh; 0.84–0.42 mm) | 95% |

A slurry of wettable powder containing 25% solids is sprayed on the surface of attapulgite granules in a double-cone blender. The granules are dried and packaged.

EXAMPLE 12

| Extruded Pellet | |
|---|---|
| 1,3-dihydro-N—[(4-methoxy-6-methyl-1,3,5-triazin-2-yl)aminocarbonyl]-1-oxo-benzo[c]furan-7-methanesulfonamide | 25% |
| anhydrous sodium sulfate | 10% |
| crude calcium ligninsulfonate | 5% |
| sodium alkylnaphthalenesulfonate | 1% |
| calcium/magnesium bentonite | 59% |

The ingredients are blended, hammer-milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 13

| Low Strength Granule | |
|---|---|
| 1,3-dihydro-N—[(4,6-dimethoxypyrimidin-2-yl)aminocarbonyl]-1-oxo-benzo[c]furan-7-methanesulfonamide | 0.1% |
| attapulgite granules (U.S.S. 20–40 mesh) | 99.9% |

The active ingredient is dissolved in a solvent and the solution is sprayed upon dedusted granules in a double-cone blender. After spraying of the solution has been completed, the material is warmed to evaporate the solvent. The material is allowed to cool and then packaged.

EXAMPLE 14

| Granule | |
|---|---|
| 1,3-dihydro-N—[(4-methoxy-6-methyl-1,3,5-triazin-2-yl)-aminocarbonyl]-1-oxo-benzo[c]furan-7-methanesulfonamide | 80% |
| wetting agent | 1% |
| crude ligninsulfonate salt (containing 5–20% of the natural sugars) | 10% |
| attapulgite clay | 9% |

The ingredients are blended and milled to pass through a 100 mesh screen. This material is then added to a fluid bed granulator, the air flow is adjusted to gently fluidize the material, and a fine spray of water is sprayed onto the fluidized material. The fluidization and spraying are continued until granules of the desired size range are made. The spraying is stopped, but fluidization is continued, optionally with heat, until the water content is reduced to the desired level, generally less than 1%. The material is then discharged, screened to the desired size range, generally 14–100 mesh (1410–149 microns), and packaged for use.

EXAMPLE 15

| Low Strength Granule | |
|---|---|
| 1,3-dihydro-N—[(4,6-dimethoxypyrimidin-2-yl)aminocarbonyl]-1-oxo-benzo[c]furan-7-methanesulfonamide | 1% |
| N,N—dimethylformamide | 9% |
| attapulgite granules (U.S.S. 20–40 sieve) | 90% |

The active ingredient is dissolved in the solvent and the solution is sprayed upon dedusted granules in a double cone blender. After spraying of the solution has been completed, the blender is allowed to run for a short period and then the granules are packaged.

EXAMPLE 16

| Aqueous Suspension | |
|---|---|
| N—[(4-methoxy-6-methyl-1,3,5-triazin-2-yl)aminocarbonyl]-2-methyl-benzo[B]thiophene-7-methanesulfonamide-1,1-dioxide | 40% |
| polyacrylic acid thickener | 0.3% |
| dodecylphenol polyethylene glycol ether | 0.5% |
| disodium phosphate | 1% |
| monosodium phosphate | 0.5% |
| polyvinyl alcohol | 1.0% |
| water | 56.7% |

The ingredients are blended and ground together in a sand mill to produce particles essentially all under 5 microns in size.

EXAMPLE 17

| Solution | |
|---|---|
| N—[(4,6-dimethoxypyrimidin-2-yl)aminocarbonyl]-2,3-dihydro-2-methyl-benzo[B]thiophene-7-methanesulfonamide-1,1-dioxide, sodium salt | 5% |
| water | 95% |

The salt is added directly to the water with stirring to produce the solution, which may then be packaged for use.

EXAMPLE 18

| High Strength Concentrate | |
|---|---|
| 1,3-dihydro-N—[(4,6-dimethoxypyrimidin-2-yl)aminocarbonyl]-1-oxo-benzo[c]furan-7-methanesulfonamide | 99% |
| silica aerogel | 0.5% |
| synthetic amorphous silica | 0.5% |

The ingredients are blended and ground in a hammer-mill to produce a material essentially all passing a U.S.S. No. 50 screen (0.3 mm opening). The concentrate may be formulated further if necessary.

EXAMPLE 19

| Wettable Powder | |
|---|---|
| N—[(4,6-dimethoxypyrimidin-2-yl)aminocarbonyl]-2,3-dihydro-2-methyl-benzo[B]thiophene-7-methanesulfonamide-1,1-dioxide | 90% |
| dioctyl sodium sulfosuccinate | 0.1% |
| synthetic fine silica | 9.9% |

The ingredients are blended and ground in a hammer-mill to produce particles essentially all below 100 microns. The material is sifted through a U.S.S. No. 50 screen and then packaged.

EXAMPLE 20

| Wettable Powder | |
|---|---|
| 1,3-dihydro-N—[(4-methoxy-6-methyl-1,3,5-triazin-2-yl)-aminocarbonyl]-1-oxo-benzo[c]furan-7-methanesulfonamide | 40% |
| sodium ligninsulfonate | 20% |
| montmorillonite clay | 40% |

The ingredients are thoroughly blended, coarsely hammer-milled and then air-milled to produce particles essentially all below 10 microns in size. The material is reblended and then packaged.

EXAMPLE 21

| Oil Suspension | |
|---|---|
| N—[(4-methoxy-6-methyl-1,3,5-triazin-2-yl)aminocarbonyl]-2-methyl-benzo[B]thiophene-7-methanesulfonamide-1,1-dioxide | 35% |
| blend of polyalcohol carboxylic esters and oil soluble petroleum sulfonates | 6% |
| xylene | 59% |

The ingredients are combined and ground together in a sand mill to produce particles essentially all below 5 microns. The product can be used directly, extended with oils, or emulsified in water.

EXAMPLE 22

| Dust | |
|---|---|
| N—[(4-methoxy-6-methyl-1,3,5-triazin-2-yl)aminocarbonyl]-2-methyl-benzo[B]thiophene-7-methanesulfonamide-1,1-dioxide | 10% |
| attapulgite | 10% |
| Pyrophyllite | 80% |

The active ingredient is blended with attapulgite and then passed through a hammer-mill to produce particles substantially all below 200 microns. The ground concentrate is then blended with powdered pyrophyllite until homogeneous.

EXAMPLE 23

| Oil Suspension | |
|---|---|
| N—[(4,6-dimethoxypyrimidin-2-yl)aminocarbonyl]-2,3-dihydro-2-methyl-benzo[B]thiophene-7-methanesulfonamide-1,1-dioxide | 25% |
| polyoxyethylene sorbitol hexaoleate | 5% |
| highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

EXAMPLE 24

| Wettable Powder | |
|---|---|
| 1,3-dihydro-N—[(4-methoxy-6-methyl-1,3,5-triazin-2-yl)-aminocarbonyl]-1-oxo-benzo[c]furan-7-methanesulfonamide | 20% |
| sodium alkylnaphthalenesulfonate | 4% |
| sodium ligninsulfonate | 4% |
| low viscosity methyl cellulose | 3% |
| attapulgite | 69% |

The ingredients are thoroughly blended. After grinding in a hammer-mill to produce particles essentially all below 100 microns, the material is reblended and sifted through a U.S.S. No. 50 sieve (0.3 mm opening) and packaged.

Utility

The compounds of the present invention are active herbicides, having utility for broad-spectrum pre- and-/or post-emergence weed control in areas where complete control of all vegetation is desired, such as around fuel storage tanks, ammunition depots, industrial storage areas, parking lots, drive-in theaters, billboards, and highway and railroad structures.

The rates of application for the compounds of the invention are determined by a number of factors, including the types of weeds to be controlled, weather and climate, formulations selected, mode of application, amount of foliage present, etc. In general terms, the subject compounds should be applied at levels of around 0.05 to 5 kg/ha, the lower rates being suggested for use on lighter soils and/or those having a low organic matter content, or for situations where only short-term persistence is required.

The compounds of the invention may be used in combination with any other commercial herbicide; examples of which are those of the triazine, triazole, uracil, urea, amide, diphenylether, carbamate and bipyridylium types. The compounds may also be used in combination with mefluidide.

The herbicidal properties of the subject compounds were discovered in a number of greenhouse tests. The test procedure and results follow.

Test A

Seeds of crabgrass (Digitaria sp.), barnyardgrass (Echinochloa crusgalli), wild oats (Avena fatua), sicklepod (Cassia obtusifolia), morningglory (Ipomoea sp.), cocklebur (Xanthium sp.), sorghum, corn, soybean, cotton rice, sugar beet, rice, wheat and purple nutsedge (Cyperus rotundus) tubers were planted in a growth medium and treated pre-emergence with the test compounds dissolved in a non-phytotoxic solvent. At the same time, these crop and weed species were treated with a soil/foliage application. At the time of treatment, the plants ranged in height from 2 to 18 cm. Treated plants and controls were maintained in a greenhouse for sixteen days, after which all species were compared to controls and visually rated for response to treatment. The ratings, summarized in Table A, are based on a numerical scale extending from 0=no injury, to 10=complete kill. The accompanying descriptive symbols have the following meanings:

C=chlorosis or necrosis;

G=growth retardation; and

H=formative effects.

The test compounds are referenced in the table of results as follows:

Compounds

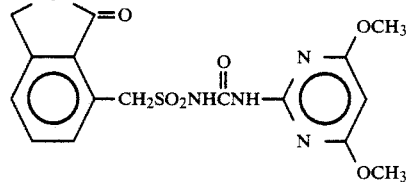

Compound 1

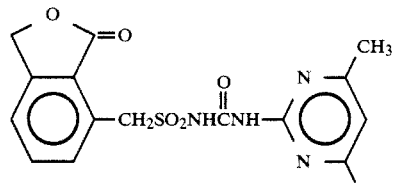

Compound 2

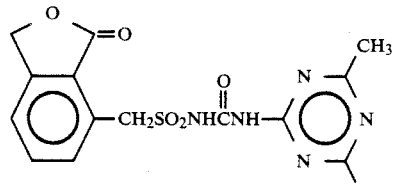

Compound 3

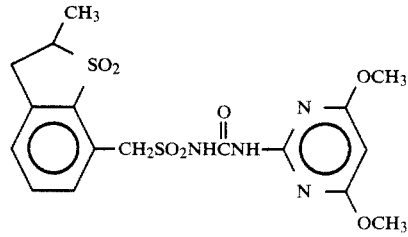

Compound 4

-continued
Compounds

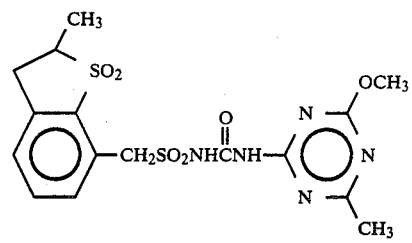

Compound 5

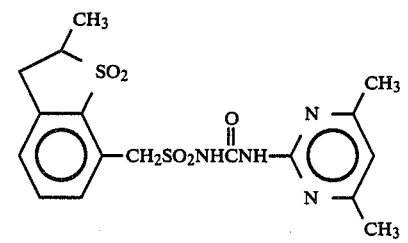

Compound 6

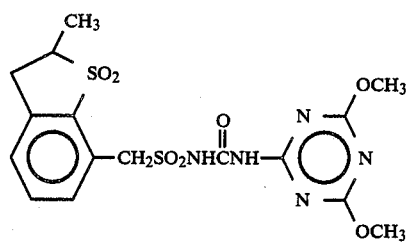

Compound 7

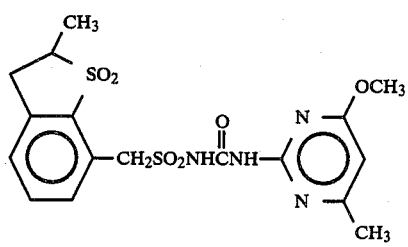

Compound 8

-continued
Compounds

Compound 9

Compound 10

Compound 11

Compound 12

TABLE A

| Rate kg/ha | Cmpd. 1 0.05 | Cmpd. 2 0.05 | Cmpd. 3 0.05 | Cmpd. 4 0.05 | Cmpd. 5 0.05 | Cmpd. 6 0.05 | Cmpd. 7 0.05 | Cmpd. 8 0.05 | Cmpd. 9 0.05 | Cmpd. 10 0.05 | Cmpd. 11 0.05 | Cmpd. 12 0.05 |
|---|---|---|---|---|---|---|---|---|---|---|---|---|
| POST-EMERGENCE ||||||||||||||
| Morningglory | 6C,9G | 3C,9G | 3C,6H | 10C | 8G | 10C | 2C,6G | 10C | 3C,9G | 3G | 9C | 10C |
| Cocklebur | 5C,8G | 5C,9G | 3C,5G | 10C | 5G | 3C,9G | 3G | 10C | 2G | 3G | 2C | 5C,9G |
| Sicklepod | 4C,8G | 3C,3H | 2C,3G | 9C | 3C,3H | 4C,7H | 2C,5G | 9C | 2C,3G | 1C | 3C,8G | 4C,6G |
| Nutsedge | 3C,8G | 2G | 2C,3G | 5G | 2C,3G | 3G | 0 | 3G | 5G | 0 | 2C,7G | 2C,6G |
| Crabgrass | 0 | 0 | 2C,5G | 3C,8G | 3C,7G | 3G | 0 | 5G | 0 | 0 | 2G | 2C |
| Barnyardgrass | 0 | 0 | 3C,6H | 4C,9H | 9C | 3C,6H | 3C,8H | 3C,8H | 0 | 0 | 0 | 0 |
| Wild Oats | 0 | 0 | 3C,6G | 3C,8G | 9C | 2C,4G | 4C,8G | 2C | 0 | 0 | 0 | 0 |
| Wheat | 0 | 0 | 3C,8G | 6G | 10C | 3G | 9C | 9G | 0 | 0 | 0 | 0 |
| Corn | 3C,9H | 1H | 3C,9G | 2U,9G | 9C | 4C,9H | 4C,9G | 3C,9H | 0 | 0 | 1H | 3C,8H |
| Soybean | 3C,9G | 2C,8G | 3H | 9C | 5C,9H | 5C,9G | 3C,8H | 9C | 5C,9G | 3C,8G | 5C,9G | 5C,9G |
| Rice | 2C,6G | 2G | 5C,9G | 6C,9G | 9C | 9C | 9C | 9C | 0 | 0 | 0 | 0 |
| Sorghum | 3C,9H | 2C,9H | 4C,9H | 6C,9H | 9C | 5C,9H | 5C,9H | 5C,9H | 0 | 0 | 3G | 3C,8H |
| Sugar beet | 9C | 4C,9H | 5C,9G | 3C,4H | 10C | 3C,7H | 9C | 3C,7G | 3C,6G | 0 | 5C,9G | 5C,9G |
| Cotton | 3C,8H | 3C,5G | 0 | 9C | 3C,7H | 5C,9G | 3C,5G | 5C,9G | 9C | 2G | 4C,9G | 4C,9G |
| PRE-EMERGENCE ||||||||||||||
| Morningglory | 8G | 2C,3H | 0 | 9G | 3C,5H | 9G | 8G | 9G | 8G | 3G | 9G | 9G |
| Cocklebur | 2C,5H | 2C,2H | — | 8H | 0 | 5H | 2H | 8H | 2H | 3G | — | 8H |
| Sicklepod | 1C,2G | 0 | 0 | 2C,7G | 2C | 2C,2H | 1C | 2C,4G | 5G | 4G | 2C,7G | 2C |
| Nutsedge | 2G | 0 | 0 | 4G | 0 | 0 | 2C | 3G | 3G | 0 | 5G | 0 |
| Crabgrass | 1C | 0 | 2G | 2C,5G | 0 | 0 | 0 | 2C,5G | 4G | 3G | 0 | 0 |
| Barnyardgrass | 0 | 0 | 1H | 4C,9H | 3C,5G | 0 | 1H | 2C,6G | 0 | 0 | 3G | 3G |
| Wild Oats | 0 | 0 | 2C,7G | 2C,8H | 8G | 2C,3G | 5G | 2C,5G | 0 | 0 | 3G | 5G |
| Wheat | 4G | 3G | 2C,8G | 3C,9H | 2C,8H | 2G | 2C,9H | 2C,7G | 0 | 0 | 4G | 8G |
| Corn | 2C,8H | 0 | 3C,7H | 2U,9G | 3C,8H | 3C,3G | 2C,8H | 4C,9H | 0 | 3G | 2C,7G | 9G |
| Soybean | 2C,8H | 0 | 0 | 3C,8H | 1C | 3C,5H | 2C,2H | 4C,6H | 1H | 0 | 2H | 3C,7G |

TABLE A-continued

|  | Cmpd. 1 | Cmpd. 2 | Cmpd. 3 | Cmpd. 4 | Cmpd. 5 | Cmpd. 6 | Cmpd. 7 | Cmpd. 8 | Cmpd. 9 | Cmpd. 10 | Cmpd. 11 | Cmpd. 12 |
|---|---|---|---|---|---|---|---|---|---|---|---|---|
| Rate kg/ha | 0.05 | 0.05 | 0.05 | 0.05 | 0.05 | 0.05 | 0.05 | 0.05 | 0.05 | 0.05 | 0.05 | 0.05 |
| Rice | 2C,7G | 2G | 3C,8H | 5C,9H | 5C,9H | 7H | 5C,9H | 5C,9H | 0 | 0 | 2G | 2G |
| Sorghum | 3C,8H | 3C,8H | 3C,9G | 5C,9H | 4C,9H | 3C,7H | 5C,9H | 4C,9G | 0 | 2G | 5G | 9G |
| Sugar beet | 9C | 3C,8G | 0 | 9C | 8G | 9C | 5G | 9C | 5G | 2G | 5C,9G | 5C,9G |
| Cotton | 8H | 1C | 0 | 9G | 2G | 5G | 5G | 3C,7G | 2G | 0 | 8G | 8G |

Test B

Postemergence

Two round pans (25 cm diameter by 12.5 cm deep) were filled with Woodstown sandy loam soil. One pan was planted with blackgrass (*Alpercurus myosuroides*), sugar beets, nutsedge (*Cyperus rotundus*) tubers, crabgrass (*Digitaria sanguinalis*), sicklepod (*Cassia obtusifolia*), teaweed (*Sida spinosa*), jimsonweed (*Datura stramonium*), velvet leaf (*Abutilon theophrasti*), oil seed rape (*Brassica napus*), and giant foxtail (*Setaria faberii*). The other pan was planted with wheat, cotton, rice, corn, soybean, wild oats (*Avena fatua*), cocklebur (*Xantium pensylvanicum*), morninglory (*Ipomoea heteracea*), johnsongrass (*Sorghum halepense*) and barnyardgrass (*Echinochloa crusgalli*). The plants were grown for approximately fourteen days, then sprayed post-emergence with the chemicals dissolved in a non-phytotoxic solvent.

Preemergence

Two round pans (25 cm diameter by 12.5 cm deep) were filled with Woodstown sandly loam soil. One pan was planted with blackgrass, sugar beets, nutsedge, crabgrass, sicklepod, teaweed, jimsonweed, velvetleaf, oil seed rape, and giant foxtail. The other pan was planted with wheat, cotton, rice, corn, soybeans, wild oats, cocklebur, morningglory, johnsongrass, and barnyardgrass. The two pans were sprayed pre-emergence with the chemicals dissolved in a non-phytotoxic solvent.

Treated plants and controls were maintained in the greenhouse for 28 days, then all treated plants were compared to controls and visually rated for plant response utilizing the rating system as described for Test A.

Response ratings are contained in Table B. The data show the potential utility of several of the compounds tested for selective weed control in crops such as wheat, soybeans and cotton.

TABLE B

PRE-EMERGENCE ON WOODSTOWN SANDY LOAM

| | Compound 1 | | | Compound 2 | | | Compound 4[1] | | | | Compound 5 | | | Compound 6 | | Compound 8 | | |
|---|---|---|---|---|---|---|---|---|---|---|---|---|---|---|---|---|---|---|
| POST-EMERGENCE ||||||||||||||||||
| Rate g/ha | 62 | 16 | 4 | 62 | 16 | 4 | 62 | 16 | 4 | 1 | 62 | 16 | 4 | 62 | 16 | 62 | 16 | 4 |
| Corn | 3G | 0 | 0 | 0 | 0 | 0 | 100,70 | 100,60 | 90,30 | 80 | 80 | 50 | 0 | 70 | 40 | 100 | 90 | 60 |
| Wheat | 0 | 0 | 0 | 0 | 0 | 0 | 0,0 | 0,0 | 0,0 | 0,0 | 0 | 0 | 0 | 50 | 0 | 70 | 0 | 0 |
| Rice | 5G | 3G | 0 | 6G | 4G | 0 | 80,0 | 70,0 | 30,0 | 0,0 | 0 | 0 | 0 | 70 | 30 | 90 | 30 | 0 |
| Soybean | 9G | 6G | 3G | 9G | 8G | 5G | 100,90 | 100,90 | 100,80 | 70,20 | 90 | 80 | 60 | 90 | 90 | 100 | 90 | 90 |
| Cotton | 7G | 3G | 0 | 5G | 3G | 0 | 100,50 | 100,20 | 40,0 | 0,0 | 60 | 0 | 0 | 0 | 0 | 90 | 20 | 0 |
| Sugar beet | 7G | 3G | 0 | 9G | 5G | 0 | 100,90 | 40,90 | 0,40 | 0,0 | 70 | 60 | 30 | 80 | 70 | 70 | 20 | 0 |
| Rape | — | — | — | — | — | — | 100,100 | 100,90 | 100,90 | 50,40 | 100 | 90 | 60 | 90 | 70 | 100 | 90 | 70 |
| Crabgrass | 0 | 0 | 0 | 3G | 0 | 0 | 20,0 | 0,0 | 0,0 | 0,0 | 0 | 0 | 0 | 20 | 0 | 60 | 0 | 0 |
| Johnsonqrass | 9G | 4G | 0 | 5G | 2G | 0 | 100,90 | 100,0 | 60,0 | 20 | 0 | 0 | 0 | 20 | 0 | 90 | 90 | 70 |
| Blackgrass | 0 | 0 | 0 | 0 | 0 | 0 | 100,70 | 70,0 | 30,0 | 0,0 | 80 | 0 | 0 | 70 | 0 | 90 | 80 | 20 |
| Barnyardgrass | 3G | 0 | 0 | 3G | 0 | 0 | 70,50 | 40,0 | 0,0 | 0,0 | 0 | 0 | 0 | 0 | 0 | 60 | 20 | 0 |
| Nutsedge | 5G | 2G | 0 | 7G | 3G | 0 | 40,— | 30,0 | 0,0 | 0,0 | 0 | 0 | 0 | 0 | 0 | 0 | 0 | 0 |
| Giant Foxtail | 6G | 0 | 0 | 7G | 4G | 0 | 50,0 | 0,0 | 0,0 | 0,0 | 0 | 0 | 0 | 0 | 0 | 40 | 0 | 0 |
| Wild Oats | 0 | 0 | 0 | 0 | 0 | 0 | 30,0 | 0,0 | 0,0 | 0,0 | 0 | 0 | 0 | 50 | 0 | 40 | 0 | 0 |
| Cocklebur | 8G | 3G | 0 | 9G | 5G | 2G | 100,90 | 60,70 | 30,0 | 0,0 | 100 | 90 | 70 | 0 | 0 | 80 | 90 | 30 |
| Morningglory | 9G | 8G | 3G | 9G | 6G | 3G | 100,90 | 40,90 | 0,90 | 0,50 | 100 | 90 | 80 | 90 | 60 | 100 | 100 | 90 |
| Teaweed | 0 | 0 | 0 | 4G | 0 | 0 | 80,80 | 50,80 | 30,0 | 0,0 | 50 | 20 | 0 | 30 | 0 | 90 | 80 | 20 |
| Sicklepod | 3G | 0 | 0 | 6G | 3G | 0 | 100,100 | 90,90 | 30,70 | 0,0 | 0 | 0 | 0 | 50 | 0 | 90 | 60 | 20 |
| Jimsonweed | 8G | 6G | 2G | 8G | 4G | 2G | 100,90 | 90,90 | 60,70 | 30,30 | 90 | 80 | 0 | 30 | 0 | 80 | 50 | 0 |
| Velvetleaf | 9G | 7G | 3G | 9G | 5G | 0 | 100,100 | 100,90 | 100,90 | 30,50 | 80 | 0 | 0 | 70 | 0 | 100 | 90 | 40 |
| PRE-EMERGENCE ||||||||||||||||||
| Rate g/ha | 250 | 62 | | 250 | 62 | 16 | 250 | 62 | 16 | | 250 | 62 | | 250 | 62 | 250 | 62 | 16 |
| Corn | 2G | 0 | | 0 | 0 | 0 | 90,100 | 40,30 | 0,0 | | 80 | 0 | | 40 | 0 | 50 | 0 | 0 |
| Wheat | 0 | 0 | | 2G | 0 | 0 | 30,30 | 0,0 | 0,0 | | 0 | 0 | | 0 | 0 | 40 | 0 | 0 |
| Rice | 7G | 4G | | 7G | 6G | 6G | 100 | 90,100 | 40,60 | | 80 | 30 | | 90 | 70 | 100 | 90 | 50 |
| Soybean | 3G | 0 | | 2C | 0 | 0 | 80,100 | 60,50 | 20,0 | | 70 | 20 | | 40 | 0 | 70 | 0 | 0 |
| Cotton | 7G | 2G | | 0 | 0 | 0 | 40,60 | 0,50 | 0,0 | | 20 | 0 | | 20 | 0 | 30 | 0 | 0 |
| Sugar beet | 9G | 3G | | 10G | 8G | 0 | 90,100 | 30,100 | 0,50 | | 80 | 20 | | 80 | 30 | 60 | 0 | 0 |
| Rape | — | — | | — | — | — | 100 | 80,50 | 30,0 | | 90 | 30 | | 60 | 20 | 90 | 20 | 0 |
| Crabgrass | 9G | 5G | | 9G | 8G | 6G | 90,60 | 0,30 | 0,0 | | 0 | 0 | | 20 | 0 | 60 | 30 | 0 |
| Johnsongrass | 8G | 4G | | 8G | 5G | 0 | 90,100 | 90,90 | 80,60 | | 90 | 80 | | 70 | 30 | 90 | 90 | 30 |
| Blackgrass | 8G | 3G | | 8G | 4G | 0 | 90,100 | 70,80 | 0,40 | | 90 | 80 | | 90 | 60 | 90 | 80 | 30 |
| Barnyardgrass | 4G | 2G | | 3G | 0 | 0 | 90,100 | 70,60 | 20,20 | | 70 | 0 | | 0 | 0 | 90 | 50 | 0 |
| Nutsedge | 8G | 5G | | 8G | 5G | 2G | 0,0 | 0,0 | 0,0 | | 70 | 20 | | 30 | 0 | 20 | 0 | 0 |
| Giant Foxtail | 6G | 2G | | 4G | 2G | 0 | 100 | 70,70 | 0,0 | | 70 | 0 | | 20 | 0 | 90 | 50 | 0 |
| Wild Oats | 0 | 0 | | 0 | 0 | 0 | 60,40 | 30,0 | 0,0 | | 0 | 0 | | 0 | 0 | 80 | 20 | 0 |
| Cocklebur | 8G | 0 | | 3G | 0 | 0 | 80,90 | 70,60 | 0,40 | | 90 | 0 | | 0 | 0 | 60 | 0 | 0 |
| Morningglory | 0 | 0 | | 3G | 0 | 0 | 90,80 | 20,30 | 0,0 | | 90 | 0 | | 0 | 0 | 0 | 0 | 0 |

TABLE B-continued
PRE-EMERGENCE ON WOODSTOWN SANDY LOAM
| | Compound 1 | | Compound 2 | | | Compound 4[1] | | | Compound 5 | | Compound 6 | | Compound 8 | |
|---|---|---|---|---|---|---|---|---|---|---|---|---|---|---|
| Teaweed | 9G | 5G | 9G | 5G | 0 | 90,90 | 50,50 | 0,0 | 60 | 20 | 60 | 0 | 90 | 50 | 20 |
| Sicklepod | 10G | 6G | 8G | 8G | 5G | 70,50 | 30,20 | 0,0 | 0 | 0 | 50 | 0 | 70 | 20 | 0 |
| Jimsonweed | 8G | 6G | 9G | 6G | 0 | 90,100 | 70,90 | 20,30 | 90 | 50 | 50 | 30 | 90 | 40 | 0 |
| Velvetleaf | 8G | 4G | 8G | 3G | 0 | 90,100 | 70,60 | 20,30 | 50 | 0 | 50 | 30 | 80 | 30 | 0 |
Note: there are two sets of data for each rate tested.
What is claimed is:
1. A compound of the formula
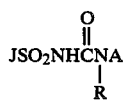
and agriculturally suitable salts thereof, wherein J is
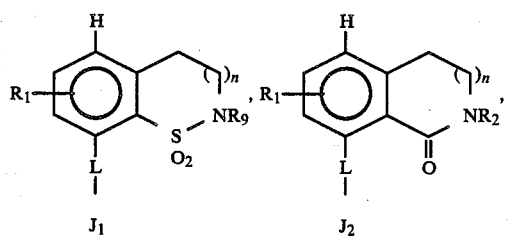
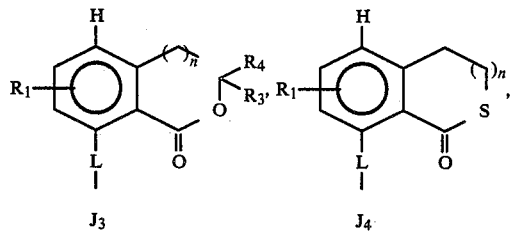
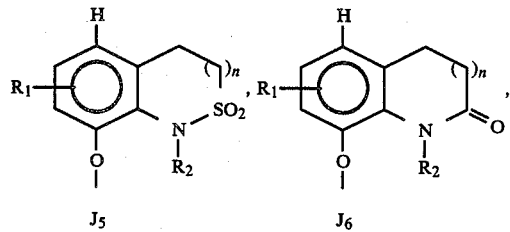
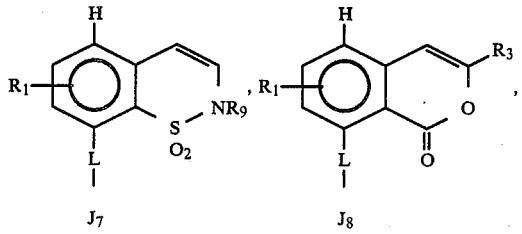
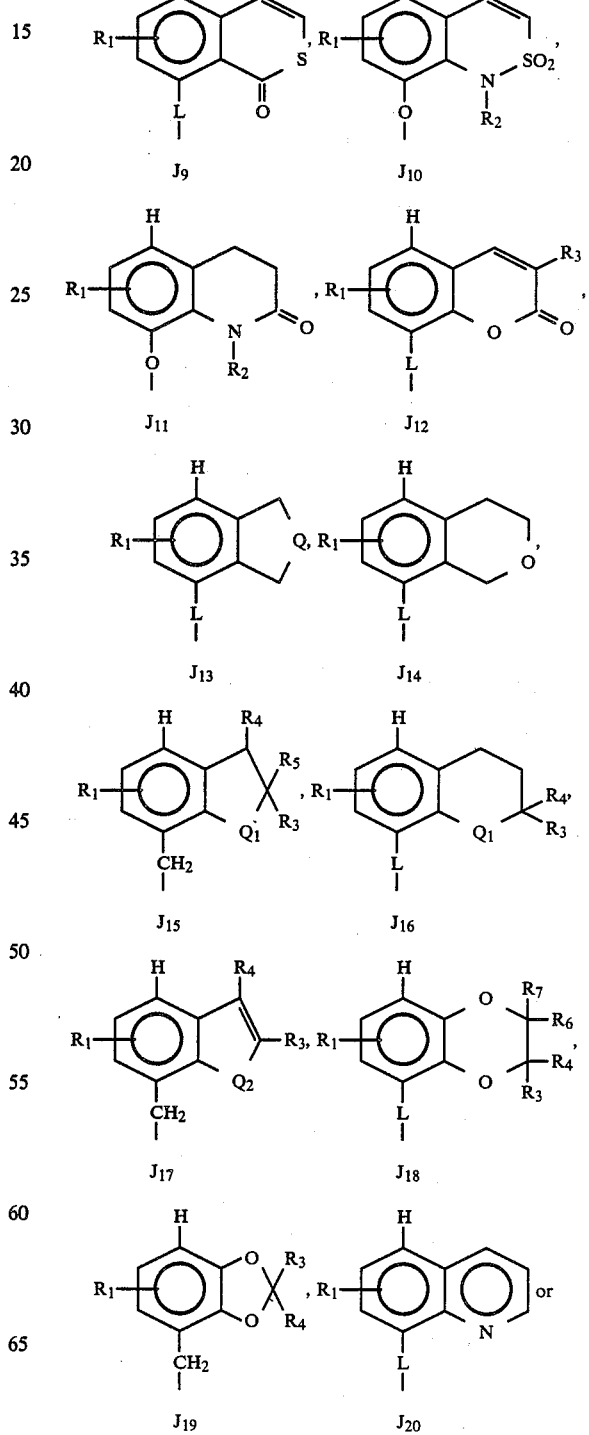

-continued

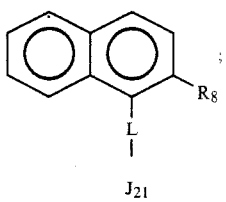

n is 0 or 1;
L is $CH_2$ or O;
Q is $CH_2$ or O;
$Q_1$ is O, S or $SO_2$;
$Q_2$ is O or S;
R is H or $CH_3$;
$R_1$ is H, F, Cl, Br, $CH_3$ or $OCH_3$;
$R_2$ is H or $C_1-C_3$ alkyl;
$R_3$ is H or $CH_3$;
$R_4$ is H or $CH_3$;
$R_5$ is H, $CH_3$ or $C_2H_5$;
$R_6$ is H or $CH_3$;
$R_7$ is H or $CH_3$;
$R_8$ is F, Cl, Br, $OCH_3$, $SCH_3$, $SO_2CH_3$, $CO_2CH_3$, $SO_2N(CH_3)_2$ or $OSO_2CH_3$;
$R_9$ is H, OH, $C_1-C_6$ alkyl, $C_1-C_6$ haloalkyl, $C_1-C_6$ alkoxyalkyl, $C_3-C_6$ alkenyl, $C_3-C_6$ alkynyl, $C_1-C_6$ alkoxy, phenyl $C_3-C_6$ cycloalkyl, $C_4-C_7$ cycloalkylalkyl, $C_1-C_6$ alkylcarbonyl, $C_1-C_6$ alkoxycarbonyl, benzyl, $C_3-C_4$ haloalkenyl, $C_3-C_6$ haloalkynyl, $C_3-C_6$ alkylcarbonylalkyl, $C_3-C_6$ alkoxycarbonylalkyl or $C_1-C_4$ cyanoalkyl;
A is

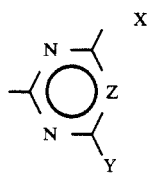 A-1

X is $CH_3$, $OCH_3$, $OCH_2CF_3$ or $OCF_2H$;
Y is $C_1-C_3$ alkyl, $CH_2F$, cyclopropyl, $C\equiv CH$, $OCH_3$, $OC_2H_5$, $CH_2OCH_3$, $NH_2$, $NHCH_3$, $N(CH_3)_2$, $OCH_2CH_2F$, $CF_3$, $SCH_3$, $OCH_2CH=CH_2$, $OCH_2C\equiv CH$, $OCH_2CH_2OCH_3$, $CR(OCH_3)_2$,

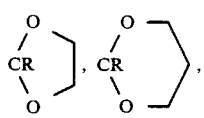

$CR(OCH_2CH_3)_2$ or $OCF_2H$; and
Z is N; provided that
X and Y are other than $OCF_2H$.

2. A compound of claim 1 where A is A-1.
3. A compound of claim 2 where Y is $CH_3$, $C_2H_5$, $OCH_3$, $OC_2H_5$, $CH_2OCH_3$, $CH_2F$ or $CF_3$; and L is $CH_2$.
4. A compound of claim 3 where J is $J_1$, $J_3$, $J_7$, $J_8$, $J_{15}$ or $J_{16}$.

5. A compound of claim 4 where R is H; $R_1$ is H; and X is $CH_3$ or $OCH_3$.
6. A compound of claim 2 where R is H; $R_9$ is H or $C_1-C_3$ alkyl; X is $CH_3$ or $OCH_3$; Y is $CH_3$, $C_2H_5$, $OCH_3$, $OC_2H_5$, $CH_2OCH_3$, $CH_2F$, or $CF_3$.
7. The compound of claim 1 which is 1,3-dihydro-N-[(4-methoxy-6-methyl-1,3,5-triazin-2-yl)aminocarbonyl]-1-oxo-benzo[c]furan-7-methanesulfonamide.
8. The compound of claim 1 which is N-[(4-methoxy-6-methyl-1,3,5-triazin-2-yl)aminocarbonyl]-2-methyl-benzo[B]thiophene-7-methanesulfonamide-1,1-dioxide.
9. A composition for the control of undesirable vegetation consisting essentially of a compound of claim 1 and at least one of (a) a surface active agent, and (b) a solid or liquid diluent.
10. A composition for the control of undesirable vegetation consisting essentially of a compound of claim 3 and at least one of (a) a surface active agent, and (b) a solid or liquid diluent.
11. A composition for the control of undesirable vegetation consisting essentially of a compound of claim 4 and at least one of (a) a surface active agent, and (b) a solid or liquid diluent.
12. A composition for the control of undesirable vegetation consisting essentially of a compound of claim 5 and at least one of (a) a surface active agent, and (b) a solid or liquid diluent.
13. A composition for the control of undesirable vegetation consisting essentially of a compound of claim 6 and at least one of (a) a surface active agent, and (b) a solid or liquid diluent.
14. A composition for the control of undesirable vegetation consisting essentially of a compound of claim 7 and at least one of (a) a surface active agent, and (b) a solid or liquid diluent.
15. A composition for the control of undesirable vegetation consisting essentially of a compound of claim 8 and at least one of (a) a surface active agent, and (b) a solid or liquid diluent.
16. A method for the control of undesirable vegetation comprising applying to the locus of such vegetation an herbicidally effective amount of a compound of claim 1.
17. A method for the control of undesirable vegetation comprising applying to the locus of such vegetation an herbicidally effective amount of a compound of claim 3.
18. A method for the control of undesirable vegetation comprising applying to the locus of such vegetation an herbicidally effective amount of a compound of claim 4.
19. A method for the control of undesirable vegetation comprising applying to the locus of such vegetation an herbicidally effective amount of a compound of claim 5.
20. A method for the control of undesirable vegetation comprising applying to the locus of such vegetation an herbicidally effective amount of a compound of claim 6.
21. A method for the control of undesirable vegetation comprising applying to the locus of such vegetation an herbicidally effective amount of a compound of claim 7.
22. A method for the control of undesirable vegetation comprising applying to the locus of such vegetation an herbicidally effective amount of a compound of claim 8.

* * * * *